United States Patent
Walter et al.

(10) Patent No.: US 12,116,406 B2
(45) Date of Patent: Oct. 15, 2024

(54) ANTI-CD33 ANTIBODIES AND USES THEREOF

(71) Applicant: Fred Hutchinson Cancer Center, Seattle, WA (US)

(72) Inventors: Roland B. Walter, Seattle, WA (US); Christopher Mehlin, Seattle, WA (US); George S. Laszlo, Seattle, WA (US); Colin E. Correnti, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 773 days.

(21) Appl. No.: 16/617,445

(22) PCT Filed: May 25, 2018

(86) PCT No.: PCT/US2018/034743
§ 371 (c)(1),
(2) Date: Nov. 26, 2019

(87) PCT Pub. No.: WO2018/218207
PCT Pub. Date: Nov. 29, 2018

(65) Prior Publication Data
US 2020/0148767 A1    May 14, 2020

Related U.S. Application Data

(60) Provisional application No. 62/511,792, filed on May 26, 2017, provisional application No. 62/532,772, filed on Jul. 14, 2017.

(51) Int. Cl.
| | |
|---|---|
| C07K 16/30 | (2006.01) |
| A61P 35/02 | (2006.01) |
| C07K 16/28 | (2006.01) |
| C07K 16/46 | (2006.01) |

(52) U.S. Cl.
CPC .......... *C07K 16/2803* (2013.01); *A61P 35/02* (2018.01); *C07K 2317/31* (2013.01); *C07K 2317/73* (2013.01); *C07K 2317/92* (2013.01)

(58) Field of Classification Search
CPC .. C07K 16/30; C07K 16/00; A61K 39/39558; A61K 39/39541
See application file for complete search history.

(56) References Cited

U.S. PATENT DOCUMENTS

| | | | |
|---|---|---|---|
| 5,929,212 A | 7/1999 | Jolliffe et al. | |
| 8,673,593 B2 | 3/2014 | Chilcote et al. | |
| 9,415,104 B2 | 8/2016 | Farag | |
| 2002/0114809 A1* | 8/2002 | Rubinfeld | A61K 31/57 424/155.1 |
| 2008/0145362 A1 | 6/2008 | Kipriyanov et al. | |
| 2013/0309223 A1* | 11/2013 | Sutherland | C07K 16/2803 424/139.1 |
| 2016/0096892 A1 | 4/2016 | Brogdon et al. | |

FOREIGN PATENT DOCUMENTS

| | | |
|---|---|---|
| WO | WO2005003172 A2 | 1/2005 |
| WO | WO2013173496 A2 | 11/2013 |
| WO | WO2015089344 | 6/2015 |
| WO | WO2016116626 A1 | 7/2016 |
| WO | WO2016201388 | 12/2016 |
| WO | WO2018014001 | 1/2018 |

OTHER PUBLICATIONS

Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Portolano (The Journal of Immunology, vol. 150, No. 3, p. 880-887, 1993) (Year: 1993).*
Beiboer (J. Mol. Biol. (2000) 296:833-849) (Year: 2000).*
Paul (Fundamental Immunology, 3rd Edition, 1993, pp. 292-295) (Year: 1993).*
Invitation to Pay Additional Fees Dated Aug. 9, 2018 for International Application No. PCT/US2018/034743, 3 pages.
Search Report and Written Opinion Dated Oct. 1, 2018, for International Application No. PCT/US2018/034743, 15 pages.
Perez-Oliva, et. al., "Epitope mapping, expression and post-translational modifications of two isoforms of CD33 (CD33M and CD33m) on lymphoid and myeloid human cells," Glycobiology, vol. 21, No. 6, 2011, pp. 757-770.
Sutherland, et al, "SGN-CD33A a novel CD33-targeting antibody-drug conjugate using a pyrrolobenzodiazepine dimer is active in models of drug-resistant AML," Blood, vol. 122, No. 8, 2013, pp. 1455-1463.
Walter, et al, "Acute myeloid leukemia stem cells and CD33-targeted immunotherapy," Blood, vol. 119, No. 26, 2012, pp. 6198-6208.

(Continued)

*Primary Examiner* — Michael Allen
(74) *Attorney, Agent, or Firm* — C. Rachal Winger; Lee & Hayes PC

(57) ABSTRACT

Anti-CD33 antibodies are described. The anti-CD33 antibodies can bind within the V-set Ig-like domain or the C2-set Ig-like domain of CD33. Epitopes FIG. 1A on the C2-set Ig-like domain can provide a "pan-binding" site, to which the cognate antibody will bind regardless of whether the CD33 molecule also contains the V-set domain (as in, for example, $CD33^{FL}$) or not (as in, for example, $CD33^{\Delta E2}$). Alternative epitopes on the C2-set Ig-like domain are accessible for binding if the V-set domain is absent (e.g., as in $CD33^{\Delta E2}$). Antibodies that bind an epitope on the C2-set Ig-like domain (whether they exhibit pan or V-set absent binding) are directed at novel therapeutic targets can increase therapeutic efficacy against CD-33-related disorders. Also described are molecules comprising a binding-competent domain from at least one described anti-CD33 antibody, including scFvs, bi-specific antibody molecules, chimeric antigen receptors, and immunoconjugates. Methods of use are also provided.

11 Claims, 15 Drawing Sheets

Specification includes a Sequence Listing.

(56) References Cited

OTHER PUBLICATIONS

Bluemel, et al., "Epitope Distance to the Target Cell Membrane and Antigen Size Determine the Potency of T Cell-Mediated Lysis by BiTE Antibodies Specific for a Large Melanoma Surface Antigen," Cancer Immunol Immunother, vol. 59, No. 8, 2010, pp. 1197-1209.

Chen, et al., "Fusion Protein Linkers: Property, Design and Functionality," Adv. Drug Deliv. Rev., vol. 65, No. 10, 2013, pp. 1357-1369.

Cleary, et al., "Antibody distance from the cell membrane regulates antibody effector mechanisms," J. Immunol., vol. 198, No. 10, 2017, pp. 3999-4011.

Cowan, et al., "Antibody-based therapy of acute myeloid leukemia with gemtuzumab ozogamicin," Front. Biosci., vol. 18, 2013, pp. 311-1334.

Godwin, et al., "Gemtuzumab ozogamicin in acute myeloid leukemia," Leukemia, vol. 31, No. 9, 2017, pp. 1855-1868.

Harrington, et al., "The Broad Anti-AML Activity of the CD33/CD3 BiTE Antibody Construct, AMG 330, Is Impacted by Disease Stage and Risk," PLoS One., vol. 10, No. 8, 2015, 13 pages.

Haso, et la., "Anti-CD22-chimeric antigen receptors targeting B-cell precursor acute lymphoblastic leukemia," Blood, vol. 121, No. 7, 2013, pp. 1165-1174.

Haworth, et al., "In Vivo Murine-Matured Human CD3+ Cells as a Preclinical Model for T Cell-Based Immunotherapies," Mol. Ther. Methods Clin. Dev., vol. 6, 2017, pp. 17-30.

June, et al., "The B7 and CD28 receptor families," Immunol. Today, vol. 15, No. 321, 1994, pp. 321-331.

Laszlo, et al., "Cellular determinants for preclinical activity of a novel CD33/CD3 bispecific T-cell engager (BiTE) antibody, AMG 330, against human AML," Blood, vol. 123, No. 4, 2014, pp. 554-561.

Laszlo, et al., "Expression and functional characterization of CD33 transcript variants in human acute myeloid leukemia," Oncotarget, vol. 7, No. 28, 2016, pp. 43281-43294.

Laszlo, et al., "The Past and Future of CD33 as Therapeutic Target in Acute Myeloid Leukemia," Blood Rev., vol. 28, No. 4, 2014, pp. 143-153.

Lin, "Ofatumumab: a novel monoclonal anti-CD20 antibody," Pharmgenomics Pers. Med., vol. 2010, No. 3, 2010, pp. 51-59.

Linsley, et al., "The role of the CD28 receptor during T cell responses to antigen," Ann. Rev. Immunol., vol. 11, No. 191, 1993, pp. 191-212.

* cited by examiner

FIG. 2

```
                             10        20        30        40        50
MfCD33_G7PYH0   MP-LLLLLPLLWAGALAMDPRVRLEVQESVTVQEGLCVLPCTFFHPVPYH
                [Signal Peptide  >[    V-set Ig-like Domain         ]
HsCD33_P20138   MPLLLLLPLLWAGALAMDPNFWLQVQESVTVQEGLCVLVPCTFFHPIPYY
                [Signal Peptide  >[    V-set Ig-like Domain         ]
MmCD33_Q63994   MLWPLPLFLLCAGSLAQDLEFQLVAPESVTVEEGLCVHVPCSVFYPSIKL
                [Signal Peptide  >[    V-set Ig-like Domain         ]

60        70        80        90        100
MfCD33_G7PYH0   TRNSPVHGYWFREGAIVSLDSPVATNKLDQEVQEETQGRFRLLGDPSRNN
                [                V-set Ig-like Domain                *]
HsCD33_P20138   DKNSPVHGYWFREGAIISRDSPVATNKLDQEVQEETQGRFRLLGDPSRNN
                [                V-set Ig-like Domain                *]
MmCD33_Q63994   TLG-PVTGSWLRKGVSLHEDSPVATSDPRQLVQKATQGRFQLLGDPQKHD
                [                V-set Ig-like Domain                 ]

110       120       130       140       150
MfCD33_G7PYH0   CSLSIVDARRRDNGSYFFRMEKG-STKYSYKSTQLSVHVTDLTHRPQILI
                [    V-set Ig-like Domain              >              [ ]
HsCD33_P20138   CSLSIVDARRRDNGSYFFRMERG-STKYSYKSPQLSVHVTDLTHRPKILI
                [    V-set Ig-like Domain              >              [ ]
MmCD33_Q63994   CSLFIRDAQKNDTGMYFFRVVREPFVRYSYKKSQLSLHVTSLSRTPDIII
                [    V-set Ig-like Domain              >              [ ]

160       170       180       190       200
MfCD33_G7PYH0   PGALDPDHSKNLTCSVPWACEQGTPPIFSWMSAAPTSLGLRTTHSSVLII
                      [*    C2-set Ig-like Domain                      ]
HsCD33_P20138   PGTLEPGHSKNLTCSVSWACEQGTPPIFSWLSAAPTSLGPRTTHSSVLII
                      [*    C2-set Ig-like Domain                      ]
MmCD33_Q63994   PGTLEAGYPSNLTCSVPWACEQGTPPTFSWMSTALTSLSSRTTDSSVLTF
                      [*    C2-set Ig-like Domain                      ]

210       220       230       240       250
MfCD33_G7PYH0   TPRPQDHGTNLTCQVKFPGAGVTTERTIQLNVSYASQNPRTDIFLGDGSG
                     [* C2-set Ig-like Domain        *>
HsCD33_P20138   TPRPQDHGTNLTCQVKFAGAGVTTERTIQLNVTYVPQNPTTGIFPGDGSG
                     [* C2-set Ig-like Domain        *>
MmCD33_Q63994   TPQPQDHGTKLTCLVTFSGAGVTVERTIQLNVTRK-------------SG
                     [* C2-set Ig-like Domain        *>

260       270       280
MfCD33_G7PYH0   RKARKQGVVQGAIGGAGVTVLLALCLCLIFFTVQ   (SEQ ID NO: 35)
                              [        TM               >
HsCD33_P20138   KQETRAGVVHGAIGGAGVTALLALCLCLIFFIVQ   (SEQ ID NO: 36)
                              [        TM               >
MmCD33_Q63994   Q---MRELVLVAVG-EATVKLLILGLCLVFLIVMF   (SEQ ID NO: 37)
                    [         TM                       >
```

Amino terminal peptides confirmed by MS

MPLLLLLPLLWADLTHRPK (E-value: 2E-3) (SEQ ID NO: 28)

M$^{oxy}$PLLLLLPLLWADLTHRPK (E-value: 2E-3) (SEQ ID NO: 29)

LLLLLPLLWADLTHRPK (E-value: 4.9E-4) (SEQ ID NO: 30)

PLLLLLPLLWADLTHRPK (E-value: 1.2E-4) (SEQ ID NO: 31)

FIG. 4A
FIG. 4B
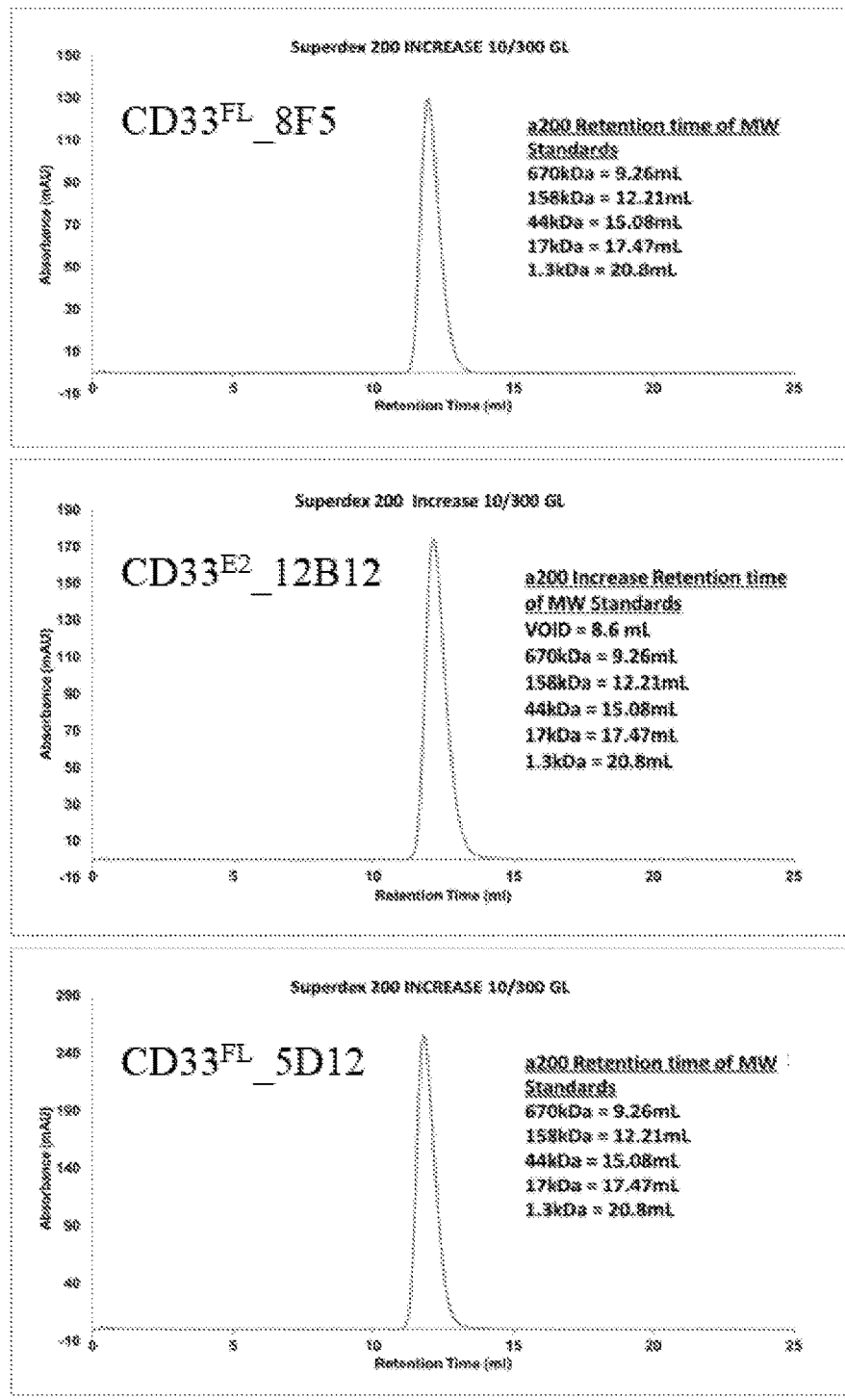
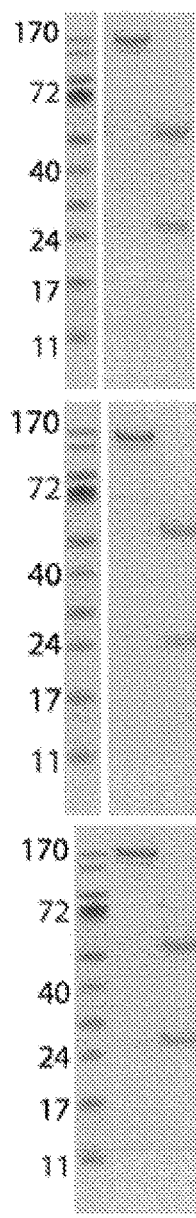

FIG. 4C
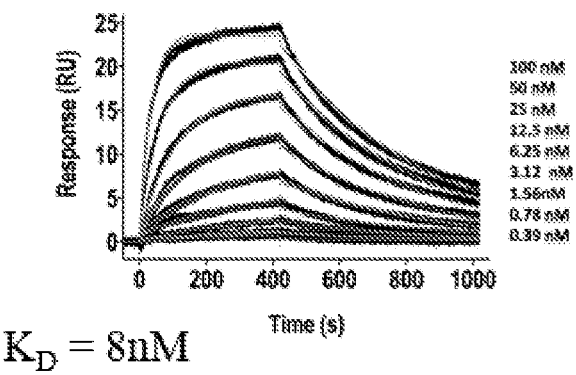
$K_D = 8nM$
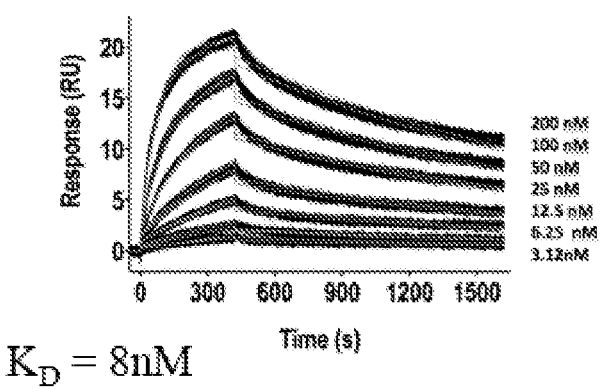
$K_D = 8nM$
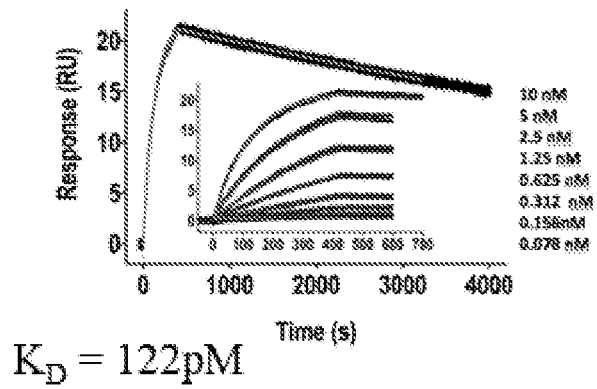
$K_D = 122pM$ scFv-based Bispecific T cell Engager IgG-based Bispecific T cell Engager

SDS-PAGE

FIG. 14A

CD33 N-terminus before and after SP cleavage

| | Exon 1 | | |
|---|---|---|---|
| before signal peptide cleavage | MPLLLLLPLLWAGALAMDPNFWLQVQESVTVQEGLCVLVPCTFF | CD33 |
| | MPLLLLLPLLWADLTHRPKILIPGTLEPGHSKNLTCSVS | CD33$^{\Delta E2}$ |
| | MPLLLLLPLLWAGALAMDLTHRPKILIPGTLEPGHSKNLTCSVS | FL SP on CD33$^{\Delta E2}$ |
| | MPLLLLLPLLWADLTHRPKILIPNFWLQVQESVTVQEGLCVLVPCTFF | $\Delta$E2 SP on CD33 |

| After signal peptide cleavage | DPNFWLQVQESVTVQEGLCVLVPCTFF | CD33 |
|---|---|---|
| | MPLLLLLPLLWADLTHRPKILIPGTLEPGHSKNLTCSVS | CD33$^{\Delta E2}$ |
| | DLTHRPKILIPGTLEPGHSKNLTCSVS | FL SP on CD33$^{\Delta E2}$ |

MPLLLLLPLLWADLTHRPKILIPNFWLQVQESVTVQEGLCVLVPCTFF $\Delta$E2 SP on CD33

13E11 epitope

ANTI-CD33 ANTIBODIES AND USES THEREOF

CROSS-REFERENCE TO RELATED APPLICATIONS

This application is a U.S. National Stage application based on International Patent Application No. PCT/US2018/034743, filed on May 25, 2018, which claims priority to U.S. Provisional Patent Application No. 62/511,792 filed May 26, 2017, and to U.S. Provisional Patent Application No. 62/532,772 filed Jul. 14, 2017, each of which is incorporated herein by reference in its entirety as if fully set forth herein.

STATEMENT REGARDING FEDERALLY SPONSORED RESEARCH OR DEVELOPMENT

This invention was made with government support under grant CA100632 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 2YZ6447-F053-0060US-ST25.txt. The text file is 149,122 bytes, was created on Sep. 25, 2023, and is being submitted electronically via Patent Center.

FIELD OF THE DISCLOSURE
IDC-A1_Sub,AMD

Anti-CD33 antibodies are described. The antibodies can bind CD33 proteins containing the V-set Ig-like domain or CD33 proteins containing the C2-set Ig-like domain (alone or together with V-set domain). Antibodies that bind the C2-set Ig-like domain (for instance, in $CD33^{\Delta E2}$ or in both $CD33^{FL}$ and $CD33^{\Delta E2}$) are directed at novel therapeutic targets and can increase the therapeutic efficacy against CD33-expressing disorders.

BACKGROUND OF THE DISCLOSURE

There are ~20,000 new cases of acute myeloid leukemia (AML) per year in the United States. Treatment outcomes remain unsatisfactory for many, with a 5-year relative survival of only 40% for patients younger than 45 years of age and only 5% for patients >65 years of age. The median age at diagnosis of AML is 67 years.

CD33 is a member of the sialic acid binding, immunoglobulin-like lectin protein family. It is a 67-kDa glycosylated transmembrane protein. Full-length CD33 ($CD33^{FL}$) is a myeloid differentiation antigen that is found at least on some leukemic cells in almost all patients with acute myeloid leukemia (AML) and, perhaps, on AML stem cells in some cases. Based on this broad expression pattern, $CD33^{FL}$ has been widely pursued as a therapeutic target in AML. Recent data from several randomized studies have demonstrated that the CD33 antibody-drug conjugate, gemtuzumab ozogamicin (GO), improves survival when added to chemotherapy in defined subsets of patients with newly diagnosed AML. This data has validated $CD33^{FL}$ as the first (and so far, only) target for immunotherapy in AML.

$CD33^{FL}$ includes a V-set Ig-like domain and a C2-set Ig-like domain (see FIGS. 1A, 1C, and 2). At the mRNA level, a splice variant of CD33 that lacks exon 2 ($CD33^{\Delta E2}$) has also been identified (see FIG. 1B). However, commercial antibodies that are currently available recognize immune-dominant epitope(s) on the V-set Ig-like domain that is encoded by exon 2 of the CD33 gene. Because of that, $CD33^{\Delta E2}$ and other CD33 proteins that lack the V-set domain are currently not recognized by any available antibody.

SUMMARY OF THE DISCLOSURE

The current disclosure provides antibodies that bind/recognize 1) the V-set domain of CD33 (including full-length CD33, $CD33^{FL}$; see FIG. 1A); 2) the C2-set domain only in CD33 proteins that lack the V-set domain (e.g., $CD33^{\Delta E2}$ is an example of such a CD33 protein; see FIG. 1B); and 3) the C2-set domain in CD33 proteins regardless of whether or not the V-set domain is present (e.g. can recognize $CD33^{FL}$ and $CD33^{\Delta E2}$; see FIG. 1C). The disclosed antibodies can be used alone or in various combinations to target unwanted CD33-expressing cells (e.g., CD33-expressing cancer cells). In combination, the disclosed antibodies can target a higher percentage of CD33-expressing cells because they can bind target cells expressing CD33 variants (such as $CD33^{\Delta E2}$) as well as $CD33^{FL}$. Further, the development of antibodies specifically binding CD33 only if the V-set domain is not present (e.g., $CD33^{\Delta E2}$) provides therapeutic targeting for cells that express variants, but that do not express protein(s) that contain the V-set domain (e.g., $CD33^{FL}$).

BRIEF DESCRIPTION OF THE SEVERAL VIEWS OF THE DRAWINGS

Many of the drawings submitted herein are better understood in color, which is not available in patent application publications at the time of filing. Applicant considers the color versions of the drawings as part of the original submission and reserve the right to present color images of the drawings in later proceedings.

FIG. 1A illustrates an example of an antibody that binds the V-set domain. FIG. 1B illustrates an example of an antibody that binds a novel epitope presented by the $CD33^{\Delta E2}$ isoform. FIG. 1C. illustrates an example of an antibody that binds the C2-set domain in the context of the full-length receptor or the $CD33^{\Delta E2}$ receptor.

FIG. 2. Sequence alignment of human, murine and cynomolgus monkey (cyno) CD33. Sequences are annotated to show secretion signals, domains, disulfide pairing and transmembrane regions: N-linked glycosylation sites are shown with asterisks. Cysteines that form disulfide bonds are shown with bars. Conserved disulfide bonds are formed between residues 41 and 101, 36 and 170, and 164 and 213; numbered as in the alignment.

FIG. 3C shows signal peptide prediction using the program SignalP. The sequence shown in FIG. 3C corresponds to positions 1-70 of SEQ ID NO: 2. FIG. 3D shows peptide sequences (SEQ ID NOs: 28-31) derived from the N-terminus of the recombinant CD33$^{\Delta E2}$ isoform as determined by mass spectrometry. Recombinant protein was reduced, alkylated and trypsinized to generate the data set.

FIGS. 4A-4C. Expression and characterization of two V-set binding (detected on CD33$^{FL}$) and one C2-set binding (detected on CD33$^{\Delta E2}$) specific antibodies. Affinities are characterized by Biacore using purified antibodies and the corresponding soluble ectodomains.

In FIG. 12A, $(G_4S)_3$ is SEQ ID NO: 158 and $G_4S$ is SEQ ID NO: 159.

FIG. 14A-14C. Schematic showing signal peptide cleavage of naturally-occurring CD33 isoforms and engineered hybrid isoforms (14A), along with characterization of two unique CD33 C2-set Ig-like domain specific CD33 antibodies with unique specificities for CD33$^{\Delta E2}$ protein. In order, the sequences shown in FIG. 14A correspond to:

residues 1-44 of SEQ ID NO: 1 (exon 1=positions 1-12);
residues 1-39 of SEQ ID NO: 2 (exon 1=positions 1-12);
SEQ ID NO: 156 (exon 1=positions 1-12);
SEQ ID NO: 157 (exon 1=positions 1-12);
residues 18-44 of SEQ ID NO: 1;
residues 1-39 of SEQ ID NO: 2 (exon 1=positions 1-12);
residues 140-166 of SEQ ID NO: 1 (which is also 13-39 of SEQ ID NO: 2); and
SEQ ID NO: 157 (exon 1=positions 1-12).

DETAILED DESCRIPTION

There are 20,000 new cases of acute myeloid leukemia (AML) per year in the United States. Treatment outcomes remain unsatisfactory for many, with a 5-year relative survival of only 40% for patients younger than 45 years of age and only 5% for patients >65 years of age. The median age at diagnosis of AML is 67 years.

Figures 1A, 1B, 1C:
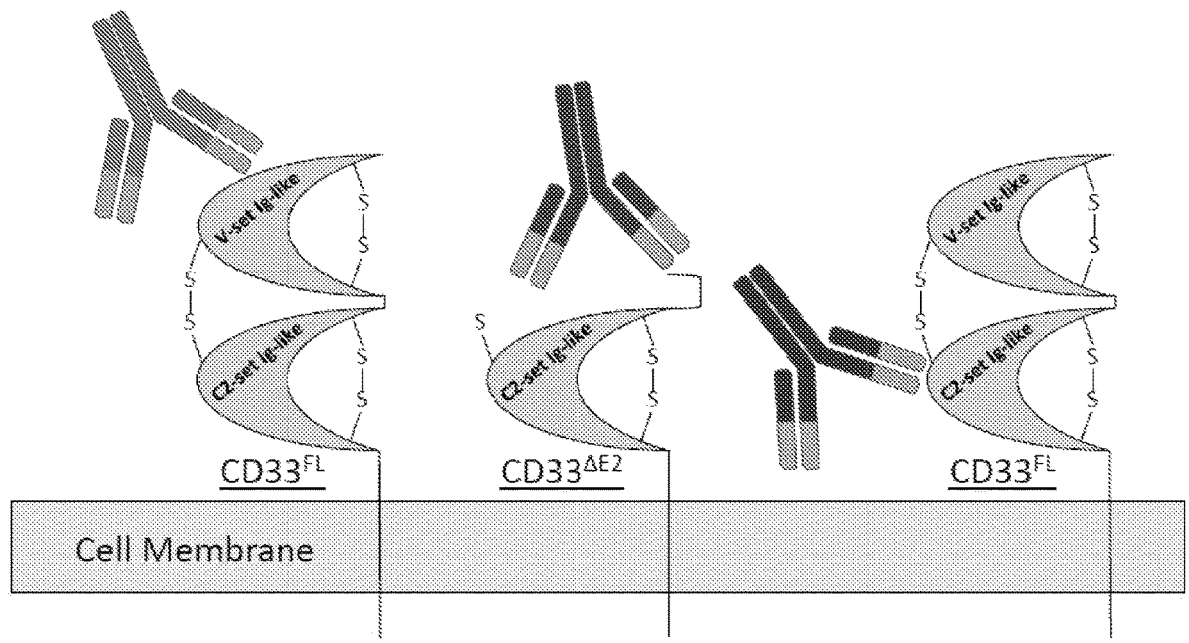
FIGS. 1A-1C. Diagrams schematically illustrating binding of anti-CD33 antibodies that bind different domains of CD33 and related isoforms.

CD33$^{FL}$ is a transmembrane glycoprotein that is characterized by an amino-terminal, membrane-distant V-set immunoglobulin (Ig)-like domain and a membrane-proximal C2-set Ig-like domain in its extracellular portion (see FIGS. 1A, 1B, and 2). CD33$^{FL}$ is primarily displayed on maturing and mature cells of the myeloid lineage, with initial expression on multipotent myeloid precursors. It is not found outside the hematopoietic system and is not thought to be expressed on pluripotent hematopoietic stem cells. Consistent with its role as a myeloid differentiation antigen, CD33$^{FL}$ is widely expressed on malignant cells in patients with myeloid neoplasms; e.g., in acute myeloid leukemia (AML), it is found on at least a subset of the AML blast cells in almost all cases and possibly leukemic stem cells in some. Because of this expression pattern, CD33$^{FL}$ has been widely exploited as an antigen for targeted therapy of AML. (Walter et al., Blood 119(26):6198-6208, 2012; Cowan et al., Front. Biosci. (Landmark Ed) 18:1311-1334, 2013; Laszlo et al., Blood Ref. 28(4):143-153, 2014.) While unconjugated monoclonal CD33 antibodies proved ineffective in the clinic, several recent randomized trials with the CD33 antibody-drug conjugate (ADC) gemtuzumab ozogamicin (GO) have demonstrated improved survival in subsets of patients with AML, establishing the value of antibodies in this disease and validating CD33$^{FL}$ as the first, and so far only, therapeutic target for immunotherapy of AML (Laszlo et al., Blood Rev. 28(4):143-153, 2014; Godwin et al., Leukemia 31(9) 31(9):1855-1868, 2017).

In addition to CD33$^{FL}$, a splice variant that misses exon 2 (CD33$^{\Delta E2}$) has also been identified at the mRNA level in normal hematopoietic cells as well as leukemia cells. Regarding the latter, CD33$^{\Delta E2}$ mRNA was identified in 29 of 29 tested AML patient specimens, indicating universal expression in human AML. CD33$^{\Delta E2}$ contains the C2-set Ig-like domain but not the V-set Ig-like domain of CD33 (see FIG. 1B). Since all commercial diagnostic CD33 antibodies and current CD33 antibody-based therapeutics recognize the immune-dominant V-set Ig-like domain that is encoded by exon 2 (see FIG. 1A), CD33$^{\Delta E2}$ and other CD33 proteins that lack the V-set domain are not recognized by any available CD33 antibody (previous studies suggested that one CD33 antibody [clone Him3-4] specifically recognizes the C2-set Ig-like domain, but other reports indicate Him3-4 only recognizes CD33$^{FL}$; Laszlo et al., Oncotarget 7(28): 43281-43294, 2016). Additional splice variants, identified at the mRNA level, include CD33$^{E7a}$ and CD33$^{\Delta E2/E7a}$.

CD33$^{E7a}$ uses an alternate exon 7 (E7a) which results in a truncation of the intracellular domain of CD33. CD33$^{\Delta E2/E7a}$ lacks exon 2 and also has the truncation of the intracellular domain of CD33. Other CD33 proteins may exist naturally.

Antibodies that recognize only CD33 proteins that lack the V-set domain (the CD33$^{\Delta E2}$ isoform being one example) (FIG. 1B) provide a novel therapeutic approach as such isoform can provide a "stand-alone" isoform-specific therapeutic target, which current CD33 antibodies are unable to bind. Additionally, antibodies that recognize both bind the C2-set domain and recognize CD33 proteins regardless of the presence/absence of the V-set domain (e.g. antibodies that bind the CD33$^{\Delta E2}$ and CD33$^{FL}$ isoforms) (FIG. 1C; "pan" antibodies) can provide better anti-CD33 effects than current CD33 antibodies because (1) they recognize a higher target antigen density due to binding to both isoforms, and/or (2) they bind closer to the membrane. For several therapeutic targets, the specifics of the targeted epitope have been shown to be critically important for antibody-based therapy, with membrane-proximal epitopes resulting in more potent anti-tumor effects than membrane-distal ones, as shown for CD20, CD22, CD25, and EpCAM. See, for instance, Cleary et al., J Immunol. 2017; 198(10):3999-4011; Lin, Pharmgenomics Pers Med. 2010; 3:51-59; Haso et al., Blood. 2013; 121(7):1165-1174; and Bluemel et al., Cancer Immunol Immunother. 2010; 59(8):1197-1209.

In particular embodiments, antibodies disclosed herein bind to CD33 and have one or more of the following characteristics:
(a) bind to recombinant human CD33;
(b) bind to recombinant cynomolgus monkey CD33;
(c) bind to endogenous CD33 on the surface of human peripheral blood mononuclear cells (PBMCs);
(d) bind to endogenous CD33 on the surface of cynomolgus monkey PBMCs;
(e) bind to endogenous CD33 on the surface of a cancer cell;
(f) bind to endogenous CD33 on the surface of an AML cancer cell;
(g) bind to an epitope within the CD33 V-set Ig-like domain;
(h) bind to an epitope within the CD33 C2-set Ig-like domain in the presence of a V-set Ig-like domain (e.g., in CD33$^{FL}$);
(i) bind to an epitope within the CD33 C2-set Ig-like domain in the absence of a V-set Ig-like domain (e.g., in CD33$^{\Delta E2}$);
(j) bind to a neoepitope on CD33$^{\Delta E2}$ due to a retained signal peptide on the amino terminal of CD33$^{\Delta E2}$;
(k) bind to a membrane proximal epitope of CD33;
(l) include a $V_L$ chain of SEQ ID NO: 8 and a $V_H$ chain of SEQ ID NO: 9;
(m) include a $V_L$ chain of SEQ ID NO: 10 and a $V_H$ chain of SEQ ID NO: 11;
(n) include a $V_L$ chain of SEQ ID NO: 12 and a $V_H$ chain of SEQ ID NO: 13;
(o) include a $V_L$ chain of SEQ ID NO: 14 and a $V_H$ chain of SEQ ID NO: 15;
(p) include a $V_L$ chain of SEQ ID NO: 16 and a $V_H$ chain of SEQ ID NO: 17;
(q) include a $V_L$ chain of SEQ ID NO: 18 and a $V_H$ chain of SEQ ID NO: 19;
(r) include a $V_L$ chain of SEQ ID NO: 20 and a $V_H$ chain of SEQ ID NO: 21;
(s) include a $V_L$ chain of SEQ ID NO: 22 and a $V_H$ chain of SEQ ID NO: 23;
(t) include a $V_L$ chain of SEQ ID NO: 24 and a $V_H$ chain of SEQ ID NO: 25;
(u) include a $V_L$ chain of SEQ ID NO: 84 and a $V_H$ chain of SEQ ID NO: 83;
(v) include a $V_L$ chain of SEQ ID NO: 154 and a $V_H$ chain of SEQ ID NO: 155;
(w) include CDRs including SEQ ID NO: 85; SEQ ID NO: 86; SEQ ID NO: 87; SEQ ID NO: 88; SEQ ID NO: 89; and SEQ ID NO: 90;
(x) include CDRs including SEQ ID NO: 130; SEQ ID NO: 131; SEQ ID NO: 132; SEQ ID NO: 133; SEQ ID NO: 134; and SEQ ID NO: 135;
(y) include CDRs including SEQ ID NO: 106, SEQ ID NO: 107, SEQ ID NO: 108, SEQ ID NO: 109, SEQ ID NO: 110, and SEQ ID NO: 111;
(z) include CDRs including SEQ ID NO: 112, SEQ ID NO: 113, SEQ ID NO: 114, SEQ ID NO: 115, SEQ ID NO: 116, and SEQ ID NO: 117;
(aa) include CDRs including SEQ ID NO: 118, SEQ ID NO: 119, SEQ ID NO: 120, SEQ ID NO: 121, SEQ ID NO: 122, and SEQ ID NO: 123;
(bb) include CDRs including SEQ ID NO: 124, SEQ ID NO: 125, SEQ ID NO: 126, SEQ ID NO: 127, SEQ ID NO: 128, and SEQ ID NO: 129;
(cc) include CDRs including SEQ ID NO: 136, SEQ ID NO: 137, SEQ ID NO: 138, SEQ ID NO: 139, SEQ ID NO: 140, and SEQ ID NO: 141;
(dd) include CDRs including SEQ ID NO: 142, SEQ ID NO: 143, SEQ ID NO: 144, SEQ ID NO: 145, SEQ ID NO: 146, and SEQ ID NO: 147
(ee) include CDRs including SEQ ID NO: 94, SEQ ID NO: 95, SEQ ID NO: 96, SEQ ID NO: 97, SEQ ID NO: 98, and SEQ ID NO: 99;
(ff) include CDRs including SEQ ID NO: 100, SEQ ID NO: 101, SEQ ID NO: 102, SEQ ID NO: 103, SEQ ID NO: 104, and SEQ ID NO: 105;
(gg) include CDRs including SEQ ID NO: 148, SEQ ID NO: 149, SEQ ID NO: 150, SEQ ID NO: 151, SEQ ID NO: 152, and SEQ ID NO: 153;
(hh) includes a humanized sequence of an antibody disclosed herein; and/or
(ii) binds to endogenous human CD33 with a $K_D$ of less than 10 nM.

Having highlighted key aspects of the current disclosure, the following more detailed description is now provided.

CD33 refers to any native, mature CD33 which results from processing of a CD33 precursor protein in a cell. A CD33-positive cell refers to any cell that expresses CD33 on its surface. A CD33-positive cancer refers to a cancer including one or more cells that express CD33 on their surface. Examples of CD33-positive cancers include leukemia, myeloid sarcoma, and lymphoma (e.g., Hodgkin's and non-Hodgkin's lymphoma). More particular examples of such cancers include acute myeloid leukemia (AML), myelodysplastic syndrome (MDS), chronic myelogenous leukemia (CML), chronic myelomonocytic leukemia (CMML), acute promyelocytic leukemia (APL), myeloproliferative neoplasms, megakaryocytic leukemia, B-cell acute lymphoblastic leukemia (B-ALL), T-cell acute lymphoblastic leukemia (T-ALL), multiple myeloma (MM) and other plasma cell dyscrasias, mast cell disease, mast cell leukemia, mast cell sarcoma, myeloid sarcomas, lymphoid leukemia, and undifferentiated leukemia.

The current disclosure provides antibodies against various CD33 epitopes.

Naturally occurring antibody structural units include a tetramer. Each tetramer includes two pairs of polypeptide chains, each pair having one light chain and one heavy chain. The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md., 1987 and 1991), or Chothia & Lesk, J. Mol. Biol., 196:901-917, 1987; Chothia et al., Nature, 342:878-883, 1989.

Definitive delineation of a CDR and identification of residues including the binding site of an antibody can be accomplished by solving the structure of the antibody and/or solving the structure of the antibody-epitope complex. In particular embodiments, this can be accomplished by methods such as X-ray crystallography. Alternatively, CDRs are determined by comparison to known antibodies (linear sequence) and without resorting to solving a crystal structure. To determine residues involved in binding, a co-crystal structure of the Fab (antibody fragment) bound to the target can optionally be determined.

The carboxy-terminal portion of each chain defines a constant region, which can be responsible for effector function particularly in the heavy chain (the Fc). Examples of effector functions include: C1q binding and complement dependent cytotoxicity (CDC); antibody-dependent cell-mediated cytotoxicity (ADCC); phagocytosis; down regulation of cell surface receptors (e.g. B-cell receptors); and B-cell activation.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989)).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgM has subclasses including IgM1 and IgM2. IgA is similarly subdivided into subclasses including IgA1 and IgA2.

As indicated, antibodies bind epitopes on antigens. The term antigen refers to a molecule or a portion of a molecule capable of being bound by an antibody. An epitope is a region of an antigen that is bound by the variable region of an antibody. Epitope determinants can include chemically active surface groupings of molecules such as amino acids, sugar side chains, phosphoryl or sulfonyl groups, and can have specific three-dimensional structural characteristics, and/or specific charge characteristics. When the antigen is a protein or peptide, the epitope includes specific amino acids within that protein or peptide that contact the variable region of an antibody.

In particular embodiments, an epitope denotes the binding site on CD33 bound by a corresponding variable region of an antibody. The variable region either binds to a linear epitope, (e.g., an epitope including a stretch of 5 to 12 consecutive amino acids), or the variable region binds to a three-dimensional structure formed by the spatial arrangement of several short stretches of the protein target. Three-dimensional epitopes recognized by a variable region, e.g. by the epitope recognition site or paratope of an antibody or antibody fragment, can be thought of as three-dimensional surface features of an epitope molecule. These features fit precisely (in) to the corresponding binding site of the variable region and thereby binding between the variable region and its target protein (more generally, antigen) is facilitated. In particular embodiments, an epitope can be considered to have two levels: (i) the "covered patch" which can be thought of as the shadow an antibody variable region would cast on the antigen to which it binds; and (ii) the individual participating side chains and backbone residues that facilitate binding. Binding is then due to the aggregate of ionic interactions, hydrogen bonds, and hydrophobic interactions.

Epitopes of the currently disclosed antibodies (that is, epitopes to which the antibodies bind) are found within the V-set Ig-like domain or the C2-set Ig-like domain of CD33. When present on the C2-set Ig-like domain, the epitope can provide a "pan binding" site, meaning that the antibody will bind regardless of whether the CD33 molecule also contains the V-set domain (as in, for example, is $CD33^{FL}$) or not (as in, for example, $CD33^{\Delta E2}$) (FIG. 1C). Alternatively, the epitope on the C2-set Ig-like domain in some embodiments can be only accessible for binding if the V-set domain is absent as in, for example, in the $CD33^{\Delta E2}$ splice variant (FIG. 1B). In particular embodiments, epitopes on the C2-set Ig-like domain are membrane-proximal epitopes. In particular embodiments, membrane membrane-proximal epitopes are within 115 residues of the transmembrane region; within 100 residues of the transmembrane region; within 75 residues of the transmembrane region; within 50 residues of the $CD33^{PAN}$ transmembrane region; within 25 residues of the transmembrane region or within 15 residues of the transmembrane region (see FIG. 2). Epitopes within the V-set Ig-like domain are also targeted by certain antibodies of the current disclosure (FIG. 1A).

In particular embodiments, "bind" means that the variable region associates with its target epitope with a dissociation constant (Kd or $K_D$) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$ M, in particular embodiments of from $10^{-8}$ M to $10^{-13}$ M, or in particular embodiments of from $10^{-9}$ M to $10^{-13}$ M. The term can be further used to indicate that the variable region does not bind to other biomolecules present (e.g., it binds to other biomolecules with a dissociation constant (Kd) of $10^{-4}$ M or more, in particular embodiments of from $10^{-4}$ M to 1 M). Binding can also reflect values as depicted in FIG. 4C ($K_D$=8 nM (8F5, 12B12); 122 pM (5D12)).

In particular embodiments, Kd can be characterized using BIAcore. For example, in particular embodiments, Kd can be measured using surface plasmon resonance assays using a BIACORE®-2000 or a BIACORE®-3000 (BIAcore, Inc., Piscataway, N.J.) at 25° C. with immobilized antigen CM5 chips at 10 response units (RU). Briefly, carboxymethylated dextran biosensor chips (CM5, BIACORE, Inc.) can be activated with N-ethyl-N'-(3-dimethylaminopropyl)-carbodiimide hydrochloride (EDC) and N-hydroxysuccinimide (NHS) according to the supplier's instructions. Antigen can be diluted with 10 mM sodium acetate, pH 4.8, to 5 pg/ml (0.2 µM) before injection at a flow rate of 5 µl/minute to achieve y 10 response units (RU) of coupled protein. Following the injection of antigen, 1 M ethanolamine can be injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of 25 µl/min. Association rates ($k_{on}$) and dissociation rates ($k_{off}$) can be calculated using a simple one-to-one Langmuir binding model (BIACORE® Evaluation Software version 3.2) by simultaneously fitting the association and dissociation sensorgrams. The equilibrium dissociation constant (Kd) can be calculated as the ratio $k_{off}/k_{on}$. See, e.g., Chen et al., J. Mol. Biol. 293:865-881, 1999. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

Unless otherwise indicated, the term "antibody" includes (in addition to antibodies having two full-length heavy chains and two full-length light chains as described above) variants, derivatives, and fragments thereof, examples of which are described below. Furthermore, unless explicitly excluded, antibodies can include monoclonal antibodies, human or humanized antibodies, bispecific antibodies, trispecific antibodies, tetraspecific antibodies, multi-specific antibodies, polyclonal antibodies, linear antibodies, minibodies, domain antibodies, synthetic antibodies, chimeric antibodies, antibody fusions, and fragments thereof, respectively. In particular embodiments, antibodies can include oligomers or multiplexed versions of antibodies.

A monoclonal antibody refers to an antibody obtained from a population of substantially homogeneous antibodies, i.e., the individual antibodies including the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies, and is not to be construed as requiring production of the antibody by any particular method. For example, monoclonal antibodies can be made by a variety of techniques, including the hybridoma method, recombinant DNA methods, phage-display methods, and methods utilizing transgenic animals containing all or part of the human immunoglobulin loci.

A "human antibody" is one which includes an amino acid sequence which corresponds to that of an antibody produced by a human or a human cell or derived from a non-human source that utilizes human antibody repertoires or other human antibody-encoding sequences.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al. (supra). In particular embodiments, for the $V_H$, the subgroup is subgroup Ill as in Kabat et al. (supra).

Human antibodies can be produced using various techniques known in the art. Human antibodies are described generally in van Dijk and van de Winkel, Curr. Opin. Pharmacol. 5: 368-74, 2001; and Lonberg, Curr. Opin. Immunol. 20:450-459, 2008. Human antibodies may be prepared by administering an immunogen to a transgenic animal that has been modified to produce intact human antibodies or intact antibodies with human variable regions in response to antigenic challenge. Such animals contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125, 2005. See also, e.g., U.S. Pat. Nos. 6,075,181 and 6,150,584 describing XENOMOUSE™ technology; U.S. Pat. No. 5,770,429 describing HUMAB technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001, 1984; Brodeur et al., Monoclonal Antibody Production Techniques and Applications, pp. 51-63 (Marcel Dekker, Inc., New York, 1987); and Boerner et al., J. Immunol., 147: 86, 1991.) Human antibodies generated via human B-cell hybridoma technology are also described in Li et al., Proc. Natl. Acad. Sci. USA, 103:3557-3562, 2006. Additional methods include those described, for example, in U.S. Pat. No. 7,189,826 (describing production of monoclonal human IgM antibodies from hybridoma cell lines) and Ni, Xiandai Mianyixue, 26(4):265-268, 2006 (describing human-human hybridomas). Human hybridoma technology (Trioma technology) is also described in Vollmers and Brandlein, Histology and Histopathology, 20(3):927-937, 2005; and Vollmers and Brandlein, Methods and Findings in Experimental and Clinical Pharmacology, 27(3):185-191, 2005.

A "humanized" antibody refers to a chimeric antibody including amino acid residues from non-human CDRs and amino acid residues from human FRs. In particular embodiments, a humanized antibody will include substantially all of at least one, and typically two, variable domains, in which all or substantially all of the CDRs correspond to those of a non-human antibody, and all or substantially all of the FRs correspond to those of a human antibody. A humanized antibody optionally may include at least a portion of an antibody constant region derived from a human antibody. A "humanized form" of an antibody, e.g., a non-human antibody, refers to an antibody that has undergone humanization.

Humanized antibodies and methods of making them are reviewed, e.g., in Almagro and Fransson, Front. Biosci. 13:1619-1633, 2008, and are further described, e.g., in Riechmann et al., Nature 332:323-329, 1988; Queen et al., Proc. Nat'l Acad. Sci. USA 86:10029-10033, 1989; U.S. Pat. Nos. 5,821,337, 7,527,791, 6,982,321, and 7,087,409; Kashmiri et al., Methods 36:25-34, 2005 (describing SDR (a-CDR) grafting); Padlan, Mol. Immunol. 28:489-498,1991 (describing "resurfacing"); Dall'Acqua et al., Methods 36:43-60,2005 (describing "FR shuffling"); and Osbourn et al., Methods 36:61-68, 2005 and Klimka et al., Br. J. Cancer, 83:252-260, 2000 (describing the "guided selection" approach to FR shuffling). EP-B-0239400 provides additional description of "CDR-grafting", in which one or more CDR sequences of a first antibody is/are placed within a framework of sequences not of that antibody, for instance of another antibody.

Human framework regions that may be used for humanization include: framework regions selected using the "best-fit" method (see, e.g., Sims et al. J. Immunol. 151:2296, 1993); framework regions derived from the consensus sequence of human antibodies of a particular subgroup of light or heavy chain variable regions (see, e.g., Carter et al., Proc. Natl. Acad. Sci. USA, 89:4285, 1992; and Presta et al., J. Immunol., 151:2623, 1993); human mature (somatically mutated) framework regions or human germline framework regions (see, e.g., Almagro and Fransson, Front. Biosci. 13:1619-1633, 2008); and framework regions derived from screening FR libraries (see, e.g., Baca et al., J. Biol. Chem. 272:10678-10684, 1997; and Rosok et al., J. Biol. Chem. 271:22611-22618, 1996).

Referring to the sequences provided herein, the following variable light ($V_L$) and variable heavy ($V_H$) chains, and CDRs, are provided for disclosed antibodies with the indicated specificities:

TABLE 1

Summary of Antibody Sequences

| Antibody Name | Specific For | Chain | SEQ ID NO: |
|---|---|---|---|
| 5D12 | V-set Ig-like domain (e.g., in $CD33^{FL}$) | $V_L$ | 8 |
| | | $V_H$ | 9 |
| | | CDRH1 | 94 |
| | | CDRH2 | 95 |
| | | CDRH3 | 96 |
| | | CDRL1 | 97 |
| | | CDRL2 | 98 |
| | | CDRL3 | 99 |
| 8F5 | V-set Ig-like domain (e.g., in $CD33^{FL}$) | $V_L$ | 10 |
| | | $V_H$ | 11 |
| | | CDRH1 | 100 |
| | | CDRH2 | 101 |
| | | CDRH3 | 102 |
| | | CDRL1 | 103 |
| | | CDRL2 | 104 |
| | | CDRL3 | 105 |
| 12B12 | C2-set Ig-like domain in the absence of V-set Ig-like domain (e.g., in $CD33^{\Delta E2}$) | $V_L$ | 12 |
| | | $V_H$ | 13 |
| | | CDRH1 | 106 |
| | | CDRH2 | 107 |
| | | CDRH3 | 108 |
| | | CDRL1 | 109 |
| | | CDRL2 | 110 |
| | | CDRL3 | 111 |
| 4H10 | C2-set Ig-like domain in the absence of V-set Ig-like domain (e.g., in $CD33^{\Delta E2}$) | $V_L$ | 14 |
| | | $V_H$ | 15 |
| | | CDRH1 | 112 |
| | | CDRH2 | 113 |
| | | CDRH3 | 114 |
| | | CDRL1 | 115 |
| | | CDRL2 | 116 |
| | | CDRL3 | 117 |

TABLE 1-continued

Summary of Antibody Sequences

| Antibody Name | Specific For | Chain | SEQ ID NO: |
|---|---|---|---|
| 11D5 | C2-set Ig-like domain in the absence of V-set Ig-like domain (e.g., in $CD33^{\Delta E2}$) | $V_L$ | 16 |
| | | $V_H$ | 17 |
| | | CDRH1 | 118 |
| | | CDRH2 | 119 |
| | | CDRH3 | 120 |
| | | CDRL1 | 121 |
| | | CDRL2 | 122 |
| | | CDRL3 | 123 |
| 13E11 | C2-set Ig-like domain in the absence of V-set Ig-like domain (e.g., in $CD33^{\Delta E2}$) | $V_L$ | 18 |
| | | $V_H$ | 19 |
| | | CDRH1 | 124 |
| | | CDRH2 | 125 |
| | | CDRH3 | 126 |
| | | CDRL1 | 127 |
| | | CDRL2 | 128 |
| | | CDRL3 | 129 |
| 5E10.7 | Pan binder, which binds C2-set Ig-like domain in the presence or absence of V-set Ig-like domain (e.g., in $CD33^{FL}$ and $CD33^{\Delta E2}$) | $V_L$ | 20 |
| | | $V_H$ | 21 |
| | | CDRH1 | 130 |
| | | CDRH2 | 131 |
| | | CDRH3 | 132 |
| | | CDRL1 | 133 |
| | | CDRL2 | 134 |
| | | CDRL3 | 135 |
| 1H7 | Pan binder, which binds C2-set Ig-like domain in the presence or absence of V-set Ig-like domain (e.g., in $CD33^{FL}$ and $CD33^{\Delta E2}$) | $V_L$ | 84 |
| | | $V_H$ | 83 |
| | | CDRL1 | 85 |
| | | CDRL2 | 86 |
| | | CDRL3 | 87 |
| | | CDRH1 | 88 |
| | | CDRH2 | 89 |
| | | CDRH3 | 90 |
| 11D11 | C2-set Ig-like domain in the absence of V-set Ig-like domain (e.g., in $CD33^{\Delta E2}$) | $V_L$ | 22 |
| | | $V_H$ | 23 |
| | | CDRH1 | 136 |
| | | CDRH2 | 137 |
| | | CDRH3 | 138 |
| | | CDRL1 | 139 |
| | | CDRL2 | 140 |
| | | CDRL3 | 141 |
| 7E7 | C2-set Ig-like domain in the absence of V-set Ig-like domain (e.g., in $CD33^{\Delta E2}$) | $V_L$ | 24 |
| | | $V_H$ | 25 |
| | | CDRH1 | 142 |
| | | CDRH2 | 143 |
| | | CDRH3 | 144 |
| | | CDRL1 | 145 |
| | | CDRL2 | 146 |
| | | CDRL3 | 147 |
| 2D5 | Pan binder, which binds C2-set Ig-like domain in the presence or absence of V-set Ig-like domain (e.g., in $CD33^{FL}$ and $CD33^{\Delta E2}$) | $V_L$ | 154 |
| | | $V_H$ | 155 |
| | | CDRH1 | 148 |
| | | CDRH2 | 149 |
| | | CDRH3 | 150 |
| | | CDRL1 | 151 |
| | | CDRL2 | 152 |
| | | CDRL3 | 153 |

Antibodies disclosed herein can be utilized to prepare various forms of relevant binding domain molecules. For example, particular embodiments can include binding fragments of an antibody, e.g., Fv, Fab, Fab', F(ab')$_2$, Fc, and single chain Fv fragments (scFvs) or any biologically effective fragments of an immunoglobulin that bind specifically to an epitope described herein.

In particular embodiments, an antibody fragment is used. An "antibody fragment" denotes a portion of a complete or full-length antibody that retains the ability to bind to an epitope. Antibody fragments can be made by various techniques, including proteolytic digestion of an intact antibody as well as production by recombinant host-cells (e.g., mammalian suspension cell lines, E. coli or phage), as described herein. Antibody fragments can be screened for their binding properties in the same manner as intact antibodies. Examples of antibody fragments include Fv, scFv, Fab, Fab', Fab'-SH, F(ab')$_2$; diabodies; and linear antibodies.

A single chain variable fragment (scFv) is a fusion protein of the variable regions of the heavy and light chains of immunoglobulins connected with a short linker peptide. Fv fragments include the $V_L$ and $V_H$ domains of a single arm of an antibody but lack the constant regions. Although the two domains of the Fv fragment, $V_L$ and $V_H$, are coded by separate genes, they can be joined, using, for example, recombinant methods, by a synthetic linker that enables them to be made as a single protein chain in which the $V_L$ and $V_H$ regions pair to form monovalent molecules (single chain Fv (scFv)). For additional information regarding Fv and scFv, see e.g., Bird, et al., Science 242:423-426, 1988; Huston, et al., Proc. Natl. Acad. Sci. USA 85:5879-5883, 1988; Plueckthun, in The Pharmacology of Monoclonal Antibodies, vol. 113, Rosenburg and Moore (eds.), Springer-Verlag, New York), (1994) 269-315; WO 1993/16185; U.S. Pat. Nos. 5,571,894; 5,587,458.

A Fab fragment is a monovalent antibody fragment including $V_L$, $V_H$, CL and CH1 domains. A F(ab')$_2$ fragment is a bivalent fragment including two Fab fragments linked by a disulfide bridge at the hinge region. For discussion of Fab and F(ab')$_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90:6444-6448, 1993. Dual affinity retargeting antibodies (DART™; based on the diabody format but featuring a C-terminal disulfide bridge for additional stabilization (Moore et al., Blood 117:4542-51, 2011)) can also be used. Antibody fragments can also include isolated CDRs. For a review of antibody fragments, see Hudson, et al., Nat. Med. 9:129-134, 2003.

In particular embodiments, an antibody disclosed herein can be a bispecific antibody. A bispecific antibody includes an antibody capable of selectively binding two or more epitopes.

Where bispecific antibodies are to be used, these may be conventional bispecific antibodies, which can be manufactured in a variety of ways (Holliger & Winter, Current Opinion Biotechnol. 4, 446-449 (1993)), for instance, prepared chemically or from hybrid hybridomas, or may be any of the bispecific antibody fragments mentioned above. scFv dimers or diabodies may be used, rather than whole antibodies. Diabodies and scFv can be constructed without an Fc region, using only variable domains (usually including the variable domain components from both light and heavy chains of the source antibody), potentially reducing the effects of anti-idiotypic reaction. Other forms of bispecific antibodies include the single chain "Janusins" described in Traunecker et al. (Embo Journal, 10, 3655-3659, 1991).

Bispecific antibodies generally include two different binding domains, with each binding domain specifically binding a different epitope either on two different antigens or on the same antigen. If a bispecific antibody is capable of selectively binding two different epitopes (a first epitope and a second epitope), the affinity of the first binding for the first epitope will generally be at least one to two or three or four orders of magnitude lower than the affinity of the first binding domain for the second epitope, and vice versa. The epitopes recognized by the bispecific antibody can be on the same or a different target (e.g., on the same or a different protein). Bispecific antibodies can be made, for example, by combining binding domains that recognize different epitopes of the same antigen.

Some example bispecific antibodies have two heavy chains (each having three heavy chain CDRs, followed by (N-terminal to C-terminal) a CH1 domain, a hinge, a CH2 domain, and a CH3 domain), and two immunoglobulin light chains that confer antigen-binding specificity through association with each heavy chain. However, additional architectures are envisioned, including bi-specific antibodies in which the light chain(s) associate with each heavy chain but do not (or minimally) contribute to antigen-binding specificity, or that can bind one or more of the epitopes bound by the heavy chain antigen-binding regions, or that can associate with each heavy chain and enable binding of one or both of the heavy chains to one or both epitopes.

In particular embodiments, a bispecific antibody can include an antibody arm combined with an arm that binds to a triggering molecule on a leukocyte, such as a T-cell receptor molecule (for example, CD3), or Fc receptors for IgG (Fc gamma R), such as Fc gamma RI (CD64), Fc gamma RII (CD32) and Fc gamma RIII (CD 16), so as to focus and localize cellular defense mechanisms to the targeted disease cell. Bispecific antibodies also can be used to localize cytotoxic agents to targeted disease cells.

Bispecific antibodies can be prepared as full-length antibodies or antibody fragments (for example, F(ab')$_2$ bispecific antibodies). For example, WO 1996/016673 describes a bispecific anti-ErbB2/anti-Fc gamma RIII antibody; U.S. Pat. No. 5,837,234 describes a bispecific anti-ErbB2/anti-Fc gamma RI antibody; WO 1998/002463 describes a bispecific anti-ErbB2/Fc alpha antibody; U.S. Pat. No. 5,821,337 describes a bispecific anti-ErbB2/anti-CD3 antibody. In particular embodiments, a bispecific antibody can be a bispecific T-cell engaging antibody (developed, for example, by Amgen, Thousand Oaks, CA under the tradename (BiTE®).

In particular embodiments, a bispecific antibody can have an extended half-life. In particular embodiments, half-life extension of a bispecific antibody can be achieved by: increasing the hydrodynamic volume of the antibody by coupling to inert polymers such as polyethylene glycol or other mimetic hydrophilic polymers; fusion or conjugation to large disordered peptides; fusing or coupling the antibody to a ligand, such as an Fc domain or to serum albumin, that binds neonatal Fc receptor (FcRn) directly to take advantage of FcRn-mediated recycling, as used by endogenous substrates such as IgGs and serum albumin; engaging FcRn recycling indirectly by fusion or coupling to a moiety that binds non-covalently to Fc or albumin (e.g., moieties such as IgG-binding domains or albumin-binding moieties, such as organic molecules (AlbuTag), fatty acids (myristic acid), peptides, binding domains from natural sources (Streptococcal protein G) and antibody modular domains (AlbudAbs, nanobodies)). In particular embodiments, the antibody can be fused or coupled to an Fc polypeptide that includes amino acid alterations that extend the in vivo half-life of an antibody that contains the altered Fc polypeptide as compared to the half-life of a similar antibody containing the same Fc polypeptide without the amino acid alterations. Such alterations can be included in an Fc polypeptide that is part of a bispecific antibody described herein. In particular embodiments, Fc polypeptide amino acid alterations can include M252Y, S254T, T256E, M428L, and/or N434S and can be used together, separately or in any combination. These alterations and a number of others are described in U.S. Pat. Nos. 7,083,784, 7,670,600, US Publication No. 2010/0234575, PCT/US2012/070146, and Zwolak, Scientific Reports 7: 15521, 2017. In particular embodiments, any substitution at one of the following amino acid positions in an Fc polypeptide can be considered an Fc alteration that extends half-life: 250, 251, 252, 259, 307, 308, 332, 378, 380, 428, 430, 434, 436. Each of these alterations or combinations of these alterations can be used to extend the half-life of a bispecific antibody as described herein. Bispecific antibodies with extended half-lives are described in, for example, U.S. Pat. No. 8,921,528 and US Patent Publication No. 2014/0308285.

Methods for making bispecific antibodies are known in the art. Traditional production of full length bispecific antibodies is based on the co-expression of two immunoglobulin heavy chain-light chain pairs, where the two chains have different specificities (see, for example, Millstein et al. Nature 305:37-39, 1983). Similar procedures are disclosed in, for example, WO 1993/008829, Traunecker et al., EMBO J. 10:3655-3659, 1991.

Techniques for generating bispecific antibodies from antibody fragments also have been described in the literature. For example, bispecific antibodies can be prepared using chemical linkage. For example, Brennan et al. (Science 229: 81, 1985) describe a procedure wherein intact antibodies are proteolytically cleaved to generate F(ab')₂ fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Binding domains derived from the antibodies disclosed herein can also be utilized within bispecific T-cell engaging antibody constructs. Bispecific T-cell engaging antibody constructs bind both a cancer antigen (e.g., CD33) on tumor cells and an immune cell (e.g., T-cell) activating epitope, with the goal of bringing immune cells to cancer cells to destroy the cancer cells. See, for example, US 2008/0145362. By way of example, SEQ ID NO: 91 is the amino acid sequence of a scFv-based bispecific T-cell engaging antibody construct containing 1H7 (based on SEQ ID NOs: 83 & 84) and a CD3 binding domain; SEQ ID NOs: 92 and 93 are the amino acid sequences of the light chain and heavy chain (respectively; based on SEQ ID NO: 83 and 84) of an IgG-based bispecific T-cell engaging antibody construct containing a CD3 binding domain and 1H7. See Example 7.

In particular embodiments, binding domains derived from the CD33 monoclonal antibodies disclosed herein can be coupled with an immune cell activating epitope to form a bispecific T-cell engaging antibody construct. Immune cells that can be targeted for localized activation by bispecific T-cell engaging antibody constructs of the current disclosure include, for example, T-cells, natural killer (NK) cells, and macrophages.

T-cell activation can be mediated by two distinct signals: those that initiate antigen-dependent primary activation and provide a T-cell receptor like signal (primary cytoplasmic signaling sequences) and those that act in an antigen-independent manner to provide a secondary or co-stimulatory signal (secondary cytoplasmic signaling sequences). Bispecific T-cell engaging antibody constructs disclosed herein can target any T-cell activating epitope that upon binding induces T-cell activation. Examples of such T-cell activating epitopes are on T-cell markers including CD2, CD3, CD7, CD27, CD28, CD30, CD40, CD83, 4-1BB (CD 137), OX40, lymphocyte function-associated antigen-1 (LFA-1), LIGHT, NKG2C, and B7-H3.

CD3 is a primary signal transduction element of T-cell receptors. CD3 is composed of a group of invariant proteins called gamma (γ), delta (Δ), epsilon (Σ), zeta (Z) and eta (H) chains. The γ, Δ, and Σ chains are structurally-related, each containing an Ig-like extracellular constant domain followed by a transmembrane region and a cytoplasmic domain of more than 40 amino acids. The Z and H chains have a distinctly different structure: both have a very short extracellular region of only 9 amino acids, a transmembrane region and a long cytoplasmic tail including 113 and 115 amino acids in the Z and H chains, respectively. The invariant protein chains in the CD3 complex associate to form noncovalent heterodimers of the Σ chain with a γ chain (Σγ) or with a Δ chain (ΣΔ) or of the Z and H chain (ZH), or a disulfide-linked homodimer of two Σ chains (ZZ). 90% of the CD3 complex incorporate the ZZ homodimer.

The cytoplasmic regions of the CD3 chains include a motif designated the immunoreceptor tyrosine-based activation motif (ITAM). This motif is found in a number of other receptors including the Ig-α/Ig-β heterodimer of the B-cell receptor complex and Fc receptors for IgE and IgG. The ITAM sites associate with cytoplasmic tyrosine kinases and participate in signal transduction following TCR-mediated triggering. In CD3, the γ, Δ and Σ chains each contain a single copy of ITAM, whereas the Z and H chains harbor three ITAMs in their long cytoplasmic regions. Indeed, the Z and H chains have been ascribed a major role in T-cell activation signal transduction pathways.

In particular embodiments, the CD3 binding domain (e.g., scFv) is derived from the OKT3 antibody (the same as the one utilized in blinatumomab). The OKT3 antibody is described in detail in U.S. Pat. No. 5,929,212. It includes a variable light chain including a CDRL1 sequence including SASSSVSYMN (SEQ ID NO: 38), a CDRL2 sequence including RWIYDTSKLAS (SEQ ID NO: 39), and a CDRL3 sequence including QQWSSNPFT (SEQ ID NO: 40). In particular embodiments, the CD3 T-cell activating epitope binding domain is a human or humanized binding domain (e.g., scFv) including a variable heavy chain including a CDRH1 sequence including KASGYTFTRYTMH (SEQ ID NO: 41), a CDRH2 sequence including INPSR-GYTNYNQKFKD (SEQ ID NO: 42), and a CDRH3 sequence including YYDDHYCLDY (SEQ ID NO: 43).

The following sequence is an scFv derived from OKT3 which retains the capacity to bind CD3: QVQLQQS-GAELARPGASVKMSCK-
ASGYTFTRYTMHWVKQRPGQGLEWIGYINPSR-GYTNYN
QKFKDKATLTTDKSSSTAYMQLSSLTSEDSAVYY-CARYYDDHYCLDYWGQGTTLTVSSSGGG
GSGGGGSGGGGSQIVLTQSPAIM-
SASPGEKVTMTCSASSSVSYMNWYQQKSGTSPKR-WIYD TSKLASGVPAHFRGSGSGTSYSLTISGMEAE-DAATYYCQQWSSNPFTFGSGTKLEINR (SEQ ID NO: 44). It may also be used as a CD3 binding domain.

In particular embodiments, the CD3 T-cell activating epitope binding domain is a human or humanized binding domain (e.g., scFv) including a variable light chain including a CDRL1 sequence including QSLVHNNGNTY (SEQ ID NO: 45), a CDRL2 sequence including KVS (SEQ ID NO: 46; not included in Sequence Listing), and a CDRL3 sequence including GQGTQYPFT (SEQ ID NO: 47). In particular embodiments, the CD3 T-cell activating epitope binding domain is a human or humanized binding domain (e.g., scFv) including a variable heavy chain including a CDRH1 sequence including GFTFTKAW (SEQ ID NO: 48), a CDRH2 sequence including IKDKSNSYAT (SEQ ID NO: 49), and a CDRH3 sequence including RGVYYAL-SPFDY (SEQ ID NO: 50). These reflect CDR sequences of the 20G6-F3 antibody.

In particular embodiments, the CD3 T-cell activating epitope binding domain is a human or humanized binding domain (e.g., scFv) including a variable light chain including a CDRL1 sequence including QSLVHDNGNTY (SEQ ID NO: 51), a CDRL2 sequence including KVS (SEQ ID NO: 52; not included in Sequence Listing), and a CDRL3 sequence including GQGTQYPFT (SEQ ID NO: 53). In particular embodiments, the CD3 T-cell activating epitope binding domain is a human or humanized binding domain (e.g., scFv) including a variable heavy chain including a CDRH1 sequence including GFTFSNAW (SEQ ID NO: 54), a CDRH2 sequence including IKARSNNYAT (SEQ ID NO: 55), and a CDRH3 sequence including RGTYYASKPFDY (SEQ ID NO: 56). These reflect CDR sequences of the 4B4-D7 antibody.

In particular embodiments, the CD3 T-cell activating epitope binding domain is a human or humanized binding domain (e.g., scFv) including a variable light chain including a CDRL1 sequence including QSLEHNNGNTY (SEQ ID NO: 57), a CDRL2 sequence including KVS (SEQ ID NO: 58; not included in Sequence Listing), and a CDRL3 sequence including GQGTQYPFT (SEQ ID NO: 59). In particular embodiments, the CD3 T-cell activating epitope binding domain is a human or humanized binding domain (e.g., scFv) including a variable heavy chain including a CDRH1 sequence including GFTFSNAW (SEQ ID NO: 60), a CDRH2 sequence including IKDKSNNYAT (SEQ ID NO: 61), and a CDRH3 sequence including RYVHYGIG-YAMDA (SEQ ID NO: 62). These reflect CDR sequences of the 4E7-C9 antibody.

In particular embodiments, the CD3 T-cell activating epitope binding domain is a human or humanized binding domain (e.g., scFv) including a variable light chain including a CDRL1 sequence including QSLVHTNGNTY (SEQ ID NO: 63), a CDRL2 sequence including KVS (SEQ ID NO: 64; not included in Sequence Listing), and a CDRL3 sequence including GQGTHYPFT (SEQ ID NO: 65). In particular embodiments, the CD3 T-cell activating epitope binding domain is a human or humanized binding domain (e.g., scFv) including a variable heavy chain including a CDRH1 sequence including GFTFTNAW (SEQ ID NO: 66), a CDRH2 sequence including KDKSNNYAT (SEQ ID NO: 67), and a CDRH3 sequence including RYVHYRFAY-ALDA (SEQ ID NO: 68). These reflect CDR sequences of the 18F5-H10 antibody.

Additional examples of anti-CD3 antibodies, binding domains, and CDRs can be found in WO2016/116626. TR66 may also be used.

CD28 is a surface glycoprotein present on 80% of peripheral T-cells in humans, and is present on both resting and activated T-cells. CD28 binds to B7-1 (CD80) and B7-2 (CD86) and is the most potent of the known co-stimulatory molecules (June et al., Immunol. Today 15:321, 1994; Linsley et al., Ann. Rev. Immunol. 11:191, 1993). In particular embodiments, the CD28 binding domain (e.g., scFv) is derived from CD80, CD86 or the 9D7 antibody. Additional antibodies that bind CD28 include 9.3, KOLT-2, 15E8, 248.23.2, and EX5.3D10. Further, 1 YJD provides a crystal structure of human CD28 in complex with the Fab fragment of a mitogenic antibody (5.11A1). In particular embodiments, antibodies that do not compete with 9D7 are selected.

Particular embodiments disclosed herein including binding domains that bind epitopes on CD8. In particular embodiments, the CD8 binding domain (e.g., scFv) is derived from the OKT8 antibody. For example, in particular embodiments, the CD8 T-cell activating epitope binding domain is a human or humanized binding domain (e.g., scFv) including a variable light chain including a CDRL1 sequence including RTSRSISQYLA (SEQ ID NO: 69), a CDRL2 sequence including SGSTLQS (SEQ ID NO: 70), and a CDRL3 sequence including QQHNENPLT (SEQ ID NO: 71). In particular embodiments, the CD8 T-cell activating epitope binding domain is a human or humanized binding domain (e.g., scFv) including a variable heavy chain including a CDRH1 sequence including GFNIKD (SEQ ID NO: 72), a CDRH2 sequence including RIDPANDNT (SEQ ID NO: 73), and a CDRH3 sequence including GYGYYVFDH (SEQ ID NO: 74). These reflect CDR sequences of the OKT8 antibody.

In particular embodiments, a binding domain is a single chain T-cell receptor (scTCR) including $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or including $V_\alpha$-$C_\alpha$, $V_\beta$-$C_\beta$, $V_\alpha$-$V_\beta$ pair specific for a target epitope of interest. In particular embodiments, T-cell activating epitope binding domains can be derived from or based on a $V_\alpha$, $V_\beta$, $C_\alpha$, or $C_\beta$ of a known TCR (e.g., a high-affinity TCR).

In particular embodiments natural killer cells (also known as NK-cells, K-cells, and killer cells) are targeted for localized activation by bispecific T-cell engaging antibody constructs. NK cells can induce apoptosis or cell lysis by releasing granules that disrupt cellular membranes, and can secrete cytokines to recruit other immune cells.

Examples of activating proteins expressed on the surface of NK cells include NKG2D, CD8, CD16, KIR2DL4, KIR2DS1, KIR2DS2, KIR3DS1, NKG2C, NKG2E, NKG2D, and several members of the natural cytotoxicity receptor (NCR) family. Examples of NCRs that activate NK cells upon ligand binding include NKp30, NKp44, NKp46, NKp80, and DNAM-1.

Examples of commercially available antibodies that bind to an NK cell receptor and induce and/or enhance activation of NK cells include: 5C6 and 1D11, which bind and activate NKG2D (available from BioLegend® San Diego, CA); mAb 33, which binds and activates KIR2DL4 (available from BioLegend®); P44-8, which binds and activates NKp44 (available from BioLegend®); SK1, which binds and activates CD8; and 3G8 which binds and activates CD16.

In particular embodiments, the bispecific T-cell engaging antibody construct can bind to and block an NK cell inhibitory receptor to enhance NK cell activation. Examples of NK cell inhibitory receptors that can be bound and blocked include KIR2DL1, KIR2DL⅔, KIR3DL1, NKG2A, and KLRG1. In particular embodiments, a binding domain that binds and blocks the NK cell inhibitory receptors KIR2DL1 and KIR2DL⅔ includes a variable light chain region of the sequence EIVLTQSPVTLSLSPGERATLSCRASQSVSSY-LAWYQQKPGQAPRLLIYDASNRATGIPARFSG SGSGTDFTLTISSLEPED-FAVYYCQQRSNWMYTFGQGTKLEIKRT (SEQ ID NO: 75) and a variable heavy chain region of the sequence QVQLVQSGAEVKKPGSSVKVS CKASGGTFSFYAISWVRQAPGQGLEWMGGFIP-IFGAANYAQKFQGRVTITADESTSTAYMELS SLRSDDTAVYYCAR-IPSGSYYYDYDMDVWGQGTTVTVSS (SEQ ID NO: 76). Additional NK cell activating antibodies are described in WO/2005/0003172 and U.S. Pat. No. 9,415,104.

In particular embodiments macrophages are targeted for localized activation by bispecific T-cell engaging antibody constructs. Macrophages are a type of leukocyte (or white blood cell) that can engulf and digest cells, cellular debris, and/or foreign substances in a process known as phagocytosis.

The bispecific T-cell engaging antibody constructs can be designed to bind to a protein expressed on the surface of macrophages. Examples of activating proteins expressed on the surface of macrophages (and their precursors, monocytes) include CD11b, CD11c, CD64, CD68, CD119, CD163, CD206, CD209, F4/80, IFGR2 Toll-like receptors (TLRs) 1-9, IL-4Rα, and MARCO. Commercially available antibodies that bind to proteins expressed on the surface of macrophages include M1/70, which binds and activates CD11b (available from BioLegend®); KP1, which binds and activates CD68 (available from ABCAM®, Cambridge, United Kingdom); and ab87099, which binds and activates CD163 (available from ABCAM®).

In particular embodiments, bispecific T-cell engaging antibody constructs can target a pathogen recognition receptor (PRR). PRRs are proteins or protein complexes that recognize a danger signal and activate and/or enhance the innate immune response. Examples of PRRs include the TLR4/MD-2 complex, which recognizes gram negative bacteria; Dectin-1 and Dectin-2, which recognize mannose moieties on fungus and other pathogens; TLR2/TLR6 or TLR2/TLR1 heterodimers, which recognize gram positive bacteria; TLR5, which recognizes flagellin; and TLR9 (CD289), which recognizes CpG motifs in DNA. In particular embodiments, bispecific T-cell engaging antibody constructs can bind and activate TLR4/MD-2, Dectin-1, Dectin-2, TRL2/TLR6, TLR2/TLR1, TLR5, and/or TLR9.

In particular embodiments, bispecific T-cell engaging antibody constructs can target the complement system. The complement system refers to an immune pathway that is induced by antigen-bound antibodies and involves signaling of complement proteins, resulting in immune recognition and clearance of the antibody-coated antigens.

Binding domains of bispecific T-cell engaging antibody constructs may be joined through a linker. A linker is an amino acid sequence which can provide flexibility and room for conformational movement between the binding domains of a bispecific T-cell engaging antibody construct. Any appropriate linker may be used. Examples of linkers can be found in Chen et al., Adv Drug Deliv Rev. 2013 Oct. 15; 65(10): 1357-1369. Linkers can be flexible, rigid, or semi-rigid, depending on the desired functional domain presentation to a target. Commonly used flexible linkers include Gly-Ser linkers such as GGSGGGSGGSG (SEQ ID NO: 77), GGSGGGSGSG (SEQ ID NO: 78) and GGSGGGSG (SEQ ID NO: 79). Additional examples include: GGGGSGGGGS (SEQ ID NO: 80); GGGSGGGS (SEQ ID NO: 81); and GGSGGS (SEQ ID NO: 82). Linkers that include one or more antibody hinge regions and/or immunoglobulin heavy chain constant regions, such as CH3 alone or a CH2CH3 sequence can also be used.

In some situations, flexible linkers may be incapable of maintaining a distance or positioning of binding domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

In particular embodiments, bispecific T-cell engaging antibody construct molecules from C2-set Ig-like domain-specific antibodies recognizing C2-set Ig-like domain in the absence of V-set Ig-like domain (e.g., in $CD33^{\Delta E2}$) or C2-set Ig-like domain in the presence or absence of V-set Ig-like domain (e.g., in $CD33^{FL}$ and $CD33^{\Delta E2}$; a pan-binding antibody) can be generated. In particular embodiments, bispecific T-cell engaging antibody construct molecules from V-set Ig-like domain-specific antibodies recognizing the V-set Ig-like domain (e.g., in $CD33^{FL}$) can be generated. Cytolytic properties of bispecific T-cell engaging antibody constructs can be confirmed in comparative in vitro assays. Briefly, for cell line experiments, target cancer cells can be incubated in 96-well round bottom plates at 5-10,000 cells/well containing increasing concentrations of the various bispecific T-cell engaging antibody constructs (e.g., CD33/CD3 bispecific T-cell engaging antibody construct including AMG 330) with/without healthy donor T-cells (used at an E:T cell ratio of 1:1 and 3:1). After 48 hours, cell numbers and drug-induced cytotoxicity, using 4',6-diamidino-2-phenylindole (DAPI) to detect non-viable cells, can be determined by flow cytometry. In experiments where healthy donor T-cells are added, cancer cells can be identified by forward/side scatter properties and negativity for CellVue Burgundy dye. Experiments can include technical duplicates.

In particular embodiments, an antibody described herein can be included as part of a chimeric antigen receptor (CAR). "Chimeric antigen receptors" or "CARs" refer to synthetically designed receptors including at least a binding domain (for instance, including domains from both a light and heavy chain) and an effector domain, and optionally a spacer domain and/or a transmembrane domain. In particular embodiments, a CAR refers to a recombinant polypeptide including an extracellular antigen binding domain in the form of a scFv, a transmembrane domain, and cytoplasmic signaling domains (also referred to herein as "an intracellular signaling domains") including a functional signaling domain derived from a stimulatory molecule as defined below. In particular embodiments, a central intracellular signaling domain of a CAR is derived from the CD3 zeta chain that is normally found associated with the TCR complex. As described more fully below, the CD3 zeta signaling domain can be fused with one or more functional signaling domains derived from at least one co-stimulatory molecule such as 4-1BB (i.e., CD137), CD27 and/or CD28.

Binding domains of CARs of the present disclosure. In particular embodiments, the binding domain binds CD33. Sources of binding domains include antibody variable regions from various species (which can be in the form of antibodies, sFvs, scFvs, Fabs, scFv-based grababody, or soluble VH domain or domain antibodies). Specific CD33 binding domains are described herein, including those which bind specifically only to the C2-set domain or only to the V-set domain of CD33. Specific CD33 binding domains include sequences from the antibodies (or $V_L$ or $V_H$, or CDRs) shown in Table 1. These antibodies can form antigen-binding regions using both a heavy and light chain variable region (for instance, functionally linked to form a single-chain antibody molecule), or in some instances only a light or only a heavy chain variable region. If only a heavy chain is used, these functional antibodies are homodimers referred to as "heavy chain antibodies" (Jespers et al., Nat. Biotechnol. 22:1161, 2004; Cortez-Retamozo et al., Cancer Res.

64:2853, 2004; Baral et al., Nature Med. 12:580, 2006; and Barthelemy et al., J. Biol. Chem. 283:3639, 2008).

An alternative source of binding domains includes sequences that encode random peptide libraries or sequences that encode an engineered diversity of amino acids in loop regions of alternative non-antibody scaffolds, such as scTCR (see, e.g., Lake et al., Int. Immunol. 11:745, 1999; Maynard et al., J. Immunol. Methods 306:51, 2005; U.S. Pat. No. 8,361,794), fibrinogen domains (see, e.g., Weisel et al., Science 230:1388, 1985), Kunitz domains (see, e.g., U.S. Pat. No. 6,423,498), designed ankyrin repeat proteins (DARPins) (Binz et al., J. Mol. Biol. 332:489, 2003 and Binz et al., Nat. Biotechnol. 22:575, 2004), fibronectin binding domains (adnectins or monobodies) (Richards et al., J. Mol. Biol. 326:1475, 2003; Parker et al., Protein Eng. Des. Selec. 18:435, 2005 and Hackel et al. (2008) J. Mol. Biol. 381:1238-1252), cysteine-knot miniproteins (Vita et al. (1995) Proc. Nat'l. Acad. Sci. (USA) 92:6404-6408; Martin et al. (2002) Nat. Biotechnol. 21:71, 2002 and Huang et al. (2005) Structure 13:755, 2005), tetratricopeptide repeat domains (Main et al., Structure 11:497, 2003 and Cortajarena et al., ACS Chem. Biol. 3:161, 2008), leucine-rich repeat domains (Stumpp et al., J. Mol. Biol. 332:471, 2003), lipocalin domains (see, e.g., WO 2006/095164, Beste et al., Proc. Nat'l. Acad. Sci. (USA) 96:1898, 1999 and Sch6 nfeld et al., Proc. Nat'l. Acad. Sci. (USA) 106:8198, 2009), V-like domains (see, e.g., US Patent Application Publication No. 2007/0065431), C-type lectin domains (Zelensky and Gready, FEBS J. 272:6179, 2005; Beavil et al., Proc. Nat'l. Acad. Sci. (USA) 89:753, 1992 and Sato et al., Proc. Nat'l. Acad. Sci. (USA) 100:7779, 2003), mAb$_2$ or Fcab (Fc antigen binding) (see, e.g., PCT Patent Application Publication Nos. WO 2007/098934 and WO 2006/072620; Wozniak-Knopp et al., Prot. Eng. Des. Select. 23:4, 289-297, 2010), armadillo repeat proteins (see, e.g., Madhurantakam et al., Protein Sci. 21: 1015, 2012; PCT Patent Application Publication No. WO 2009/040338), affilin (Ebersbach et al., J. Mol. Biol. 372: 172, 2007), affibody, avimers, knottins, fynomers, atrimers, cytotoxic T-lymphocyte associated protein-4 (Weidle et al., Cancer Gen. Proteo. 10:155, 2013) or the like (Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and Plückthun, Curr. Opin. Biotechnol. 22:849, 2011).

Effector Domains of CARs of the present disclosure. Effector domains are capable of transmitting functional signals to a cell. In particular embodiments, an effector domain will directly or indirectly promote a cellular response by associating with one or more other proteins that directly promote a cellular response. Effector domains can provide for activation of at least one function of a transduced lymphocyte expressing the CAR upon binding to CD33 on a targeted cell. Activation of the lymphocyte can include one or more of proliferation, differentiation, activation or other effector functions.

An effector domain may include one, two, three or more receptor signaling domains, intracellular signaling domains, costimulatory domains, or combinations thereof. Any intracellular effector domain, costimulatory domain or both from any of a variety of signaling molecules (e.g., signal transduction receptors) may be used in the CARs of this disclosure.

Exemplary effector domains include those from 4-1 BB, CD3ε, CD3δ, CD3ζ, CD27, CD28, CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, PTCH2, or any combination thereof.

T-cell activation can be said to be mediated by two distinct classes of cytoplasmic signaling sequence: those that initiate antigen-dependent primary activation and provide a T-cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as immunoreceptor tyrosine-based activation motifs or ITAMs. Examples of ITAMs containing primary cytoplasmic signaling sequences include those derived from CD3 zeta, FcR gamma, CD3 gamma, CD3 delta, CD3 epsilon, CD5, CD22, CD79a, CD79b, and CD66d.

In particular embodiments, an effector domain includes a cytoplasmic portion that associates with a cytoplasmic signaling protein, wherein the cytoplasmic signaling protein is a lymphocyte receptor or signaling domain thereof, a protein including a plurality of ITAMs, a costimulatory factor, or any combination thereof.

Examples of intracellular signaling domains include the cytoplasmic sequences of the CD3 zeta chain, and/or co-receptors that act in concert to initiate signal transduction following CAR engagement, as well as any derivative or variant of these sequences and any synthetic sequence that has the same functional capability. In particular embodiments, an intracellular signaling domain of a CAR can be designed to include an intracellular signaling domain combined with any other desired cytoplasmic domain(s). For example, the intracellular signaling domain of a CAR can include an intracellular signaling domain and a costimulatory signaling region. The costimulatory signaling region refers to a portion of the CAR including the intracellular domain of a costimulatory molecule. A costimulatory molecule is a cell surface molecule other than the expressed marker ligand that is required for a response of lymphocytes to a marker. Examples of such molecules include CD27, CD28, 4-1 BB (CD 137), OX40, CD30, CD40, lymphocyte function-associated antigen-1 (LFA-1), CD2, CD7, LIGHT, NKG2C, B7-H3, and a ligand that specifically binds with CD83.

CARs disclosed herein can also include spacer region(s). Spacer regions can be customized for individual markers on targets to optimize target recognition. In particular embodiments, a spacer length can be selected based upon the location of a marker epitope, affinity of an antibody for the epitope, and/or the ability of the lymphocytes expressing the CAR to proliferate in vitro and/or in vivo in response to marker recognition.

Typically, a spacer region is found between the binding domain and a transmembrane domain of the CAR. Spacer regions can provide for flexibility of the binding domain and allows for high expression levels in the modified cells. In particular embodiments, a spacer region can have at least 10 to 250 amino acids, at least 10 to 200 amino acids, at least 10 to 150 amino acids, at least 10 to 100 amino acids, at least 10 to 50 amino acids or at least 10 to 25 amino acids and including any integer between the endpoints of any of the listed ranges. particular embodiments, a spacer region has 250 amino acids or less; 200 amino acids or less, 150 amino acids or less; 100 amino acids or less; 50 amino acids or less; 40 amino acids or less; 30 amino acids or less; 20 amino acids or less; or 10 amino acids or less.

In particular embodiments, spacer regions can be derived from a hinge region of an immunoglobulin like molecule, for example all or a portion of the hinge region from a human IgG1, human IgG2, a human IgG3, or a human IgG4. Hinge regions can be modified to avoid undesirable structural interactions such as dimerization. In particular embodiments, all or a portion of a hinge region can be combined with one or more domains of a constant region of an immunoglobulin. For example, a portion of a hinge region can be combined with all or a portion of a CH2 or CH3 domain or variant thereof.

CARs disclosed herein can also include transmembrane domains. The transmembrane domain provides for anchoring of the CAR in the lymphocyte membrane. The transmembrane domain may be derived either from a natural or a synthetic source. When the source is natural, the domain may be derived from any membrane-bound or transmembrane protein.

Transmembrane regions include at least the transmembrane region(s) of) the alpha, beta, or zeta chain of the T-cell receptor, CD28, CD3, CD45, CD4, CD8, CD9, CD16, CD22; CD33, CD37, CD64, CD80, CD86, CD134, CD137, and CD154. In particular embodiments, synthetic or variant transmembrane domains include predominantly hydrophobic residues such as leucine and valine.

Different potential CAR nucleic acids that encode different CD33 binding domains, different spacer region lengths, different intracellular binding domains and/or different transmembrane domains, can be tested in vivo (for instance, in an animal model) and/or in vitro to identify CAR(s) with improved function over other CARs.

Variants of antibodies described herein are also included. Variants of antibodies can include those having one or more conservative amino acid substitutions or one or more non-conservative substitutions that do not adversely affect the binding of the protein as indicated in the accompanying FIGS.

In particular embodiments, a conservative amino acid substitution may not substantially change the structural characteristics of the reference sequence (e.g., a replacement amino acid should not tend to break a helix that occurs in the reference sequence, or disrupt other types of secondary structure that characterizes the reference sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden & J. Tooze, eds., Garland Publishing, New York, N.Y. (1991)); and Thornton et al., Nature, 354:105 (1991).

In particular embodiments, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (lie), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and lie. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, lie, Val, and Cys; and large aromatic residues: Phe, Tyr, and Trp. Additional information is found in Creighton (1984) Proteins, W.H. Freeman and Company.

In particular embodiments, a $V_L$ region can be derived from or based on a disclosed $V_L$ and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the disclosed $V_L$. An insertion, deletion or substitution may be anywhere in the $V_L$ region, including at the amino- or carboxy-terminus or both ends of this region, provided that each CDR includes zero changes or at most one, two, or three changes and provided an antibody including the modified $V_L$ region can still specifically bind its target epitope with an affinity similar to the wild type binding domain.

In particular embodiments, a $V_H$ region can be derived from or based on a disclosed $V_H$ and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_H$ disclosed herein. An insertion, deletion or substitution may be anywhere in the $V_H$ region, including at the amino- or carboxy-terminus or both ends of this region, provided that each CDR includes zero changes or at most one, two, or three changes and provided an antibody including the modified $V_H$ region can still specifically bind its target epitope with an affinity similar to the wild type binding domain.

In particular embodiments including bispecific T-cell engaging antibody constructs, T-cell activating epitope binding domains include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a $V_\alpha$, $V_\beta$, $C_\alpha$, or $C_\beta$ region, including at the amino- or carboxy-terminus or both ends of these regions, provided that each CDR includes zero changes or at most one, two, or three changes and provided a binding domain including a modified $V_\alpha$, $V_\beta$, $C_\alpha$, or $C_\beta$ region can still specifically bind its target with an affinity similar to wild type.

In particular embodiments, one or more amino acid modifications may be introduced into the Fc region of an antibody, thereby generating an Fc region variant. The Fc region variant may include a human Fc region sequence (e.g., a human IgG1, IgG2, IgG3 or IgG4 Fc region) including an amino acid modification (e.g., a substitution) at one or more amino acid positions.

In particular embodiments, variants have been modified from a reference sequence to produce an administration benefit. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-live.

In particular embodiments the antibodies can be mutated to increase the half-life of the antibodies in serum. M428L/

N434S is a pair of mutations that increase the half-life of antibodies in serum, as described in Zalevsky et al., Nature Biotechnology 28, 157-159, 2010.

In particular embodiments the antibodies can be mutated to increase their affinity for Fc receptors. Exemplary mutations that increase the affinity for Fc receptors include: G236A/S239D/A330L/I332E (GASDALIE). Smith et al., Proceedings of the National Academy of Sciences of the United States of America, 109(16), 6181-6186, 2012. In particular embodiments, an antibody variant includes an Fc region with one or more amino acid substitutions which improve ADCC, e.g., substitutions at positions 298, 333, and/or 334 of the Fc region (EU numbering of residues). In particular embodiments, alterations are made in the Fc region that result in altered C1q binding and/or Complement Dependent Cytotoxicity (CDC), e.g., as described in U.S. Pat. No. 6,194,551, WO 99/51642, and Idusogie et al., J. Immunol. 164: 4178-4184, 2000.

In particular embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further below. In particular embodiments, residue 5400 (EU numbering) of the heavy chain Fc region is selected. Cysteine engineered antibodies may be generated as described, e.g., in U.S. Pat. No. 7,521,541.

In particular embodiments, a variant includes or is a sequence that has at least 90%, at least 91%, at least 92%, at least 93%, at least 94%, at least 95%, at least 96%, at least 97%, at least 98%, at least 99%, at least 99.5% sequence identity to an antibody sequence disclosed herein. In particular embodiments, a variant includes or is a sequence that has at least 90%, at least 91%, at least 92%, at least 93%, at least 94%, at least 95%, at least 96%, at least 97%, at least 98%, at least 99%, at least 99.5% sequence identity to a light chain variable region ($V_L$) and/or to a heavy chain variable region ($V_H$), or both, wherein each CDR includes zero changes or at most one, two, or three changes, from the reference antibody disclosed herein or fragment or derivative thereof that specifically binds to a targeted CD33 epitope.

Antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at position 297 in the Fc region (Eu numbering of Fc region residues); however, Asn297 may also be located ±3 amino acids upstream or downstream of position 297, i.e., between positions 294 and 300, due to minor sequence variations in antibodies. Such fucosylation variants may have improved ADCC function.

See, e.g., WO2000/61739; WO 2001/29246; WO2002/031140; US2002/0164328; WO2003/085119; WO2003/084570; US2003/0115614; US2003/0157108; US2004/0093621; US2004/0110704; US2004/0132140; US2004/0110282; US2004/0109865; WO2005/035586; WO2005/035778; WO2005/053742; Okazaki et al. J. Mol. Biol. 336:1239-1249 (2004); and Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545, 1986, and knockout cell lines, such as alpha-1,6-fucosyltransferase gene, FUT8, knockout CHO cells (see, e.g., Yamane-Ohnuki et al., Biotech. Bioeng. 87: 614, 2004; Kanda et al., Biotechnol. Bioeng., 94(4):680-688, 2006; and WO2003/085107).

In particular embodiments, modified antibodies include those wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications also include nitrited constructs.

In particular embodiments, variants include glycosylation variants wherein the number and/or type of glycosylation site has been altered compared to the amino acid sequences of a reference sequence. In particular embodiments, glycosylation variants include a greater or a lesser number of N-linked glycosylation sites than the reference sequence. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (e.g., those that are naturally occurring) are eliminated and one or more new N-linked sites are created. Additional antibody variants include cysteine variants wherein one or more cysteine residues are deleted from or substituted for another amino acid (e.g., serine) as compared to the reference sequence. These cysteine variants can be useful when antibodies must be refolded into a biologically active conformation such as after the isolation of insoluble inclusion bodies. These cysteine variants generally have fewer cysteine residues than the reference sequence, and typically have an even number to minimize interactions resulting from unpaired cysteines.

PEGylation particularly is a process by which polyethylene glycol (PEG) polymer chains are covalently conjugated to other molecules such as proteins. Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

Covalent attachment of proteins to PEG has proven to be a useful method to increase the half-lives of proteins in the body (Abuchowski, A. et al., Cancer Biochem. Biophys., 1984, 7:175-186; Hershfield, M. S. et al., N. Engl. J. Medicine, 1987, 316:589-596; and Meyers, F. J. et al., Clin. Pharmacol. Ther., 49:307-313, 1991). The attachment of PEG to proteins not only protects the molecules against enzymatic degradation, but also reduces their clearance rate from the body. The size of PEG attached to a protein has significant impact on the half-life of the protein. The ability of PEGylation to decrease clearance is generally not a function of how many PEG groups are attached to the protein, but the overall molecular weight of the altered protein.

Usually the larger the PEG is, the longer the in vivo half-life of the attached protein. In addition, PEGylation can also decrease protein aggregation (Suzuki et al., Biochem. Bioph. Acta 788:248, 1984), alter protein immunogenicity (Abuchowski et al., J. Biol. Chem. 252: 3582, 1977), and increase protein solubility as described, for example, in PCT Publication No. WO 92/16221).

Several sizes of PEGs are commercially available (Nektar Advanced PEGylation Catalog 2005-2006; and NOF DDS Catalogue Ver 7.1), which are suitable for producing proteins with targeted circulating half-lives. A variety of active PEGs have been used including mPEG succinimidyl succinate, mPEG succinimidyl carbonate, and PEG aldehydes, such as mPEG-propionaldehyde.

In particular embodiments, antibodies disclosed herein are formed using the Daedalus expression system as described in Pechman et al. (Am J Physiol 294: R1234-R1239, 2008). The Daedalus system utilizes inclusion of minimized ubiquitous chromatin opening elements in transduction vectors to reduce or prevent genomic silencing and to help maintain the stability of decigram levels of expression. This system can bypass tedious and time-consuming steps of other protein production methods by employing the secretion pathway of serum-free adapted human suspension cell lines, such as 293 Freestyle. Using optimized lentiviral vectors, yields of 20-100 mg/l of correctly folded and post-translationally modified, endotoxin-free protein of up to 70 kDa in size, can be achieved in conventional, small-scale (100 ml) culture. At these yields, most proteins can be purified using a single size-exclusion chromatography step, immediately appropriate for use in structural, biophysical or therapeutic applications. Bandaranayake et al., Nucleic Acids Res., 39(21) 2011. In some instances, purification by chromatography may not be needed due to the purity of manufacture according to the methods described herein.

In particular embodiments, using variable region CD33 antibody sequences derived from 5' RACE (rapid cloning of cDNA ends) cloning and the CD3 sequence from AMG 330, bispecific molecules can be assembled by synthesizing each scFv as a DNA fragment with overlapping Gibson assembly-compatible ends in the canonical bispecific T-cell engaging antibody format. Prototypical intervening regions such as 3xG$_4$S (SEQ ID NO: 158) linkers can be used between paired variable domains and a short 1xG$_4$S (SEQ ID NO: 159) linker between the two scFvs.

Vector can be mixed with psPAX2 packaging and pMD2.G envelope vectors and complexed with PEI to transfect suspension adapted HEK293T cells in 96-deep well blocks. Lentivirus can be harvested and then used to transduce Freestyle® 293-F cells in 96-deep well format and the cells are allowed to grow until viability begins to decline. IRES-driven GFP reporter expression can be monitored by flow cytometry to track target expression and identify failed transductions or weak expressers. Following incubation, conditioned media can be harvested and proteins can be purified using Protino® 96-sample Ni-NTA purification plates. Typical yields for bispecific T-cell engaging antibody construct proteins at this scale range from 50-200 pg.

In particular embodiments, the antibodies can also be formed as immunoconjugates. Immunoconjugates include an anti-CD33 antibody disclosed herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioimmunoconjugate). A toxin can be any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom). The toxin may be obtained from essentially any source; it may be synthetic or a natural product isolated from a selected source, e.g., a plant, bacterial, insect, mammalian or fungal source. The toxin may also be a synthetically modified natural product or an analogue of a natural product. Frequently used plant toxins are divided into two classes: (1) holotoxins (or class II ribosome inactivating proteins), such as ricin, abrin, mistletoe lectin, and modeccin, and (2) hemitoxins (class I ribosome inactivating proteins), such as pokeweed antiviral protein (PAP), saporin, Bryodin 1, bouganin, and gelonin. Commonly used bacterial toxins include diphtheria toxin (DT) and *Pseudomonas* exotoxin (PE). Kreitman, Current Pharmaceutical Biotechnology 2:313-325 (2001). The toxin may also be an antibody or other peptide.

Examples of radioactive isotopes that can be conjugated to antibodies of the present disclosure include iodine-131, indium-111, yttrium-90, and lutetium-177, as well as alpha-emitting radionuclides such as astatine-211 or bismuth-212 or bismuth-213. Methods for preparing radioimmunoconjugates are established in the art. Examples of radioimmunoconjugates are commercially available, including Zevalin™ (DEC Pharmaceuticals), and similar methods can be used to prepare radioimmunoconjugates using the antibodies of the disclosure.

Immunoconjugates allow for the targeted delivery of a drug moiety to cancer cell, and, in particular embodiments intracellular accumulation therein, where systemic administration of unconjugated drugs may result in unacceptable levels of toxicity to normal cells (Polakis P. (2005) Current Opinion in Pharmacology 5:382-387).

Immunoconjugates include antibody-drug conjugates (ADC). ADC are targeted chemotherapeutic molecules which combine properties of both antibodies and cytotoxic drugs by targeting potent cytotoxic drugs to antigen-expressing cancer cells (Teicher, B. A. (2009) Current Cancer Drug Targets 9:982-1004), thereby enhancing the therapeutic index by maximizing efficacy and minimizing off-target toxicity (Carter, P. J. and Senter P. D. (2008) The Cancer Jour. 14(3):154-169; Chari, R. V. (2008) Acc. Chem. Res.

41:98-107). See also Kamath & Iyer (Pharm Res. 32(11): 3470-3479, 2015), which describes considerations for the development of ADCs.

ADC compounds of the disclosure include those with anticancer activity. In particular embodiments, the ADC compounds include an antibody conjugated, i.e. covalently attached, to the drug moiety. In particular embodiments, the antibody is covalently attached to the drug moiety through a linker. A linker can include any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid0 based linker. The ADCs selectively deliver an effective dose of a drug to cancer cells whereby greater selectivity, i.e. a lower efficacious dose, may be achieved while increasing the therapeutic index ("therapeutic window").

The drug moiety (D) of the ADC may include any compound, moiety or group that has a cytotoxic or cytostatic effect. Drug moieties may impart their cytotoxic and cytostatic effects by mechanisms including tubulin binding, DNA binding or intercalation, and inhibition of RNA polymerase, protein synthesis, and/or topoisomerase. Exemplary drug moieties include maytansinoid (including monomethyl auristatin E [MMAE]; vedotin), dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity.

To prepare ADCs, linker-cytotoxin conjugates can be made by conventional methods analogous to those described by Doronina et al. (Bioconjugate Chem. 17: 114-124, 2006). Antibodies, e.g., monoclonal antibodies, can be raised against a specific cancer target antigen (e.g., CD33), purified, and characterized. Therapeutic ADCs containing that antibody can be prepared by standard methods for cysteine conjugation, such as by methods analogous to that described in Hamblett et al., Clin. Cancer Res. 10:7063-7070, 2004; Doronina et al., Nat. Biotechnol. 21(7): 778-784, 2003; and Francisco et al., Blood 102:1458-1465, 2003.

Antibody-drug conjugates with multiple (e.g., four) drugs per antibody can be prepared by partial reduction of the antibody with an excess of a reducing reagent such as dithiothreitol (DTT) or tris(2-carboxyethyl)phosphine (TCEP) at 37° C. for 30 min, then the buffer can be exchanged by elution through the gel filtration polymer SEPHADEX® (Cytiva Bioprocess (Uppsala, Sweden)) G-25 with 1 mM DTPA in Dulbecco's phosphate-buffered saline (DPBS). The eluent can be diluted with further DPBS, and the thiol concentration of the antibody can be measured using 5,5'-dithiobis(2-nitrobenzoic acid) [Ellman's reagent]. An excess, for example 5-fold, of the linker-cytotoxin conjugate can be added at 4° C. for 1 hr, and the conjugation reaction can be quenched by addition of a substantial excess, for example 20-fold, of cysteine. The resulting ADC mixture can be purified on SEPHADEX® G-25 equilibrated in PBS to remove unreacted linker-cytotoxin conjugate, desalted if desired, and purified by size-exclusion chromatography. The resulting ADC can then be sterile filtered, for example, through a 0.2 µm filter, and can be lyophilized if desired for storage.

Any of the antibodies described herein in any exemplary format can be formulated alone or in combination into compositions for administration to subjects. Salts and/or pro-drugs of the antibodies can also be used.

A pharmaceutically acceptable salt includes any salt that retains the activity of the antibody and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes an active ingredient which is converted to a therapeutically active compound after administration, such as by cleavage or by hydrolysis of a biologically labile group.

In particular embodiments, the compositions include antibodies of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA (ethylene-diamine-tetra-acetic acid).

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the antibodies or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, a-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on therapeutic weight.

The compositions disclosed herein can be formulated for administration by, for example, injection, inhalation, infusion, perfusion, lavage, or ingestion. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, intrathecal, intratumoral, intramuscular, intravesicular, and/or subcutaneous injection.

For injection, compositions can be formulated as aqueous solutions, such as in buffers including Hanks' solution, Ringer's solution, or physiological saline. The aqueous solutions can include formulatory agents such as suspending, stabilizing, and/or dispersing agents.

Alternatively, the formulation can be in lyophilized and/or powder form for constitution with a suitable vehicle, e.g., sterile pyrogen-free water, before use.

For oral administration, the compositions can be formulated as tablets, pills, dragées, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g., lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated as an aerosol. In particular embodiments, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated including a powder mix of the composition and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salt.

Additionally, compositions can be formulated as sustained-release systems utilizing semipermeable matrices of solid polymers including at least one type of antibody. Various sustained-release materials have been established and are well known by those of ordinary skill in the art. Sustained-release systems may, depending on their chemical nature, release one or more antibodies following administration for a few weeks up to over 100 days. Depot preparations can be administered by injection; parenteral injection; instillation; or implantation into soft tissues, a body cavity, or occasionally into a blood vessel with injection through fine needles.

Depot formulations can include a variety of bioerodible polymers including poly(lactide), poly(glycolide), poly(caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Delaware), poly(vinyl alcohol) (PVA), Brij® (Croda Americas, Wilmington, Delaware), sucrose acetate isobutyrate (SAIB), salts, and buffers.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Methods of Use. Methods disclosed herein include treating subjects (humans, veterinary animals (dogs, cats, reptiles, birds, etc.) livestock (horses, cattle, goats, pigs, sheep, chickens, etc.) and research animals (monkeys, rats, mice, fish, etc.) with compositions disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. Effective amounts are often administered for research purposes. Effective amounts disclosed herein can cause a statistically-significant effect in an animal model or in vitro assay relevant to the assessment of a CD33-related disorder's development or progression.

A "prophylactic treatment" includes a treatment administered to a subject who does not display signs or symptoms of a CD33-related (for instance, CD33-expressing) disorder or displays only early signs or symptoms of a CD33-related disorder such that treatment is administered for the purpose of diminishing or decreasing the risk of developing the CD33-related disorder further. Thus, a prophylactic treatment functions as a preventative treatment against a CD33-related disorder.

A "therapeutic treatment" includes a treatment administered to a subject who displays symptoms or signs of a CD33-related disorder and is administered to the subject for the purpose of diminishing or eliminating those signs or symptoms of the CD33-related disorder. The therapeutic treatment can reduce, control, or eliminate the presence or activity of the CD33-related disorder and/or reduce control or eliminate side effects of the CD33-related disorder.

Function as an effective amount, prophylactic treatment or therapeutic treatment are not mutually exclusive, and in particular embodiments, administered dosages may accomplish more than one treatment type.

In particular embodiments, therapeutically effective amounts provide anti-cancer effects.

Anti-cancer effects include a decrease in the number of cancer cells, an increase in life expectancy, induced chemo- or radiosensitivity in cancer cells, inhibited cancer cell proliferation, prolonged subject life, reduced cancer-associated pain, and/or reduced relapse or re-occurrence of cancer following treatment.

In particular embodiments, therapeutically effects amounts induce an immune response.

The immune response can be against a cancer cell.

Examples of CD33-related disorders include hematological cancers such as leukemias and lymphomas and other myelo- or lymphoproliferative disorders.

Exemplary leukemias include acute lymphoblastic leukemia (ALL), acute myeloid leukemia (AML), chronic lymphoid leukemia, chronic myelogenous leukemia (CML), chronic myelomonocytic leukemia (CML), lymphoid leukemia, mast cell leukemia, myelodysplastic syndrome (MDS), B-cell acute lymphoblastic leukemia (B-ALL), T-cell acute lymphoblastic leukemia (T-ALL), megakaryocytic leukemia, and undifferentiated leukemia.

Exemplary sub-types of AML include: acute basophilic leukemia, acute erythroid leukemia (AML-M6), acute megakaryoblastic leukemia (AML-M7), acute monoblastic leukemia (AML-M5a), acute monocytic leukemia (AML-M5b), acute myeloblasts leukemia with granulocytic maturation, acute myeloblasts leukemia without maturation, acute myelomonocytic leukemia (AML-M4), acute panmyelosis with myelofibrosis, acute promyelocytic leukemia (APL), erythroleukemia (AML-M6a), minimally differentiated acute myeloblasts leukemia, myelomonocytic leukemia with bone marrow eosinophilia, and pure erythroid leukemia (AML-M6b).

Exemplary lymphomas include Burkitt's lymphoma, diffuse large B-cell lymphoma, follicular lymphoma (small cell and large cell), Hodgkin's and non-Hodgkin's lymphoma, mantle cell lymphoma, and multiple myeloma.

Compositions disclosed herein can also be used to treat a complication or disease related to the above-noted lymphoproliferative disorders and hematological cancers. For example, complications relating to AML may include a preceding myelodysplastic syndrome (MDS, formerly known as "preleukemia"), secondary leukemia, in particular secondary AML, high white blood cell count, and absence of Auer rods. Among others, leukostasis and involvement of the central nervous system (CNS), hyperleukocytosis, residual disease, are also considered complications or diseases related to AML.

Compositions disclosed herein can may also find use in the treatment of other pathological conditions or genetic syndromes associated with the risk of AML such as Down syndrome, trisomy, Fanconi anemia, Bloom syndrome, Ataxia-telangiectasia, Diamond-Blackfan anemia, Schwachman-Diamond syndrome, Li-Fraumeni syndrome, Neurofibromatosis type 1, Severe congenital neutropenia (also called Kostmann syndrome).

Compositions disclosed herein may also find use in the treatment of Alzheimer's disease.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of CD33-related disorder, stage of CD33-related disorder, previous or concurrent therapeutic interventions, idiopathy of the subject and route of administration.

Useful doses can range from 0.1 to 5 pg/kg or from 0.5 to 1 pg/kg. In other examples, a dose can include 1 pg/kg, 15 pg/kg, 30 pg/kg, 50 pg/kg, 55 pg/kg, 70 pg/kg, 90 pg/kg, 150 pg/kg, 350 pg/kg, 500 pg/kg, 750 pg/kg, 1000 pg/kg, 0.1 to 5 mg/kg or from 0.5 to 1 mg/kg. In other examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

The pharmaceutical compositions described herein can be administered by injection, inhalation, infusion, perfusion, lavage or ingestion. Routes of administration can include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

The Exemplary Embodiments and Example below are included to demonstrate particular, non-limiting embodiments of the disclosure. Those of ordinary skill in the art will recognize in light of the present disclosure that many changes can be made to the specific embodiments disclosed herein and still obtain a like or similar result without departing from the spirit and scope of the disclosure.

Exemplary Embodiments

1. An isolated antibody or binding-competent fragment thereof comprising a binding domain specific for an epitope in a CD33 domain, and comprising at least one of:
   (i) a VH domain comprising the following CDRs:
   SEQ ID NO: 85, SEQ ID NO: 86, and SEQ ID NO: 87; or
   SEQ ID NO: 130, SEQ ID NO: 131, and SEQ ID NO: 132; or
   SEQ ID NO: 148, SEQ ID NO: 149, and SEQ ID NO: 150; or
   SEQ ID NO: 106, SEQ ID NO: 107, and SEQ ID NO: 108; or
   SEQ ID NO: 112, SEQ ID NO: 113, and SEQ ID NO: 114; or
   SEQ ID NO: 118, SEQ ID NO: 119, and SEQ ID NO: 120; or
   SEQ ID NO: 124, SEQ ID NO: 125, and SEQ ID NO: 126; or
   SEQ ID NO: 136, SEQ ID NO: 137, and SEQ ID NO: 138; or
   SEQ ID NO: 142, SEQ ID NO: 143, and SEQ ID NO: 144; or
   SEQ ID NO: 94, SEQ ID NO: 95, and SEQ ID NO: 96; or
   SEQ ID NO: 100, SEQ ID NO: 101, ad SEQ ID NO: 102; and
   (ii) a VL domain comprising the following CDRs:
   SEQ ID NO: 88, SEQ ID NO: 89, and SEQ ID NO: 90; or
   SEQ ID NO: 133, SEQ ID NO: 134, and SEQ ID NO: 135; or
   SEQ ID NO: 151, SEQ ID NO: 152, and SEQ ID NO: 153; or
   SEQ ID NO: 109, SEQ ID NO: 110, and SEQ ID NO: 111; or
   SEQ ID NO: 115, SEQ ID NO: 116, and SEQ ID NO: 117; or
   SEQ ID NO: 121, SEQ ID NO: 122, and SEQ ID NO: 123; or
   SEQ ID NO: 127, SEQ ID NO: 128, and SEQ ID NO: 129; or
   SEQ ID NO: 139, SEQ ID NO: 140, and SEQ ID NO: 141; or
   SEQ ID NO: 145, SEQ ID NO: 146, and SEQ ID NO: 147; or
   SEQ ID NO: 97, SEQ ID NO: 98, and SEQ ID NO: 99; or
   SEQ ID NO: 103, SEQ ID NO: 104, and SEQ ID NO: 105.

2. The antibody or fragment thereof of embodiment 1, which binds the C2-set Ig-like domain of CD33, comprising:
   SEQ ID NO: 85, SEQ ID NO: 86, SEQ ID NO: 87, SEQ ID NO: 88, SEQ ID NO: 89, and SEQ ID NO: 90; or
   SEQ ID NO: 130, SEQ ID NO: 131, SEQ ID NO: 132, SEQ ID NO: 133, SEQ ID NO: 134, and SEQ ID NO: 135; or
   SEQ ID NO: 148, SEQ ID NO: 149, SEQ ID NO: 150, SEQ ID NO: 151, SEQ ID NO: 152, and SEQ ID NO: 153.

3. The antibody or fragment thereof of embodiment 2, comprising SEQ ID NO: 83 and SEQ ID NO: 84.

4. The antibody or fragment thereof of embodiment 2, comprising SEQ ID NO: 20 and SEQ ID NO: 21.

5. The antibody or fragment thereof of embodiment 2, comprising SEQ ID NO: 154 and SEQ ID NO: 155.

6. The antibody of embodiment 2, comprising 1H7, 5E10.7, or 2D5.

7. The antibody or fragment thereof of embodiment 1, which binds the C2-set Ig-like domain only in the absence of the V-set Ig-like domain, comprising:
   SEQ ID NO: 106, SEQ ID NO: 107, SEQ ID NO: 108, SEQ ID NO: 109, SEQ ID NO: 110, and SEQ ID NO: 111;
   SEQ ID NO: 112, SEQ ID NO: 113, SEQ ID NO: 114, SEQ ID NO: 115, SEQ ID NO: 116, and SEQ ID NO: 117;
   SEQ ID NO: 118, SEQ ID NO: 119, SEQ ID NO: 120, SEQ ID NO: 121, SEQ ID NO: 122, and SEQ ID NO: 123;
   SEQ ID NO: 124, SEQ ID NO: 125, SEQ ID NO: 126, SEQ ID NO: 127, SEQ ID NO: 128, and SEQ ID NO: 129; SEQ ID NO: 136, SEQ ID NO: 137, SEQ ID NO: 138, SEQ ID NO: 139, SEQ ID NO: 140, and SEQ ID NO: 141; or
   SEQ ID NO: 142, SEQ ID NO: 143, SEQ ID NO: 144, SEQ ID NO: 145, SEQ ID NO: 146, and SEQ ID NO: 147

8. The antibody or fragment thereof of embodiment 7, comprising SEQ ID NO: 12 and SEQ ID NO: 13.

9. The antibody or fragment thereof of embodiment 7, comprising SEQ ID NO: 14 and SEQ ID NO: 15.

10. The antibody or fragment thereof of embodiment 7, comprising SEQ ID NO: 16 and SEQ ID NO: 17.

11. The antibody or fragment thereof of embodiment 7, comprising SEQ ID NO: 18 and SEQ ID NO: 19.

12. The antibody or fragment thereof of embodiment 7, comprising SEQ ID NO: 22 and SEQ ID NO: 23.

13. The antibody or fragment thereof of embodiment 7, comprising SEQ ID NO: 24 and SEQ ID NO: 25.

14. The antibody of embodiment 7, comprising 12B12, 4H10, 11D5, 13E11, 11D11, or 7E7.

15. The antibody or fragment thereof of embodiment 1, which binds the V-set Ig-like domain of CD33, comprising:
   SEQ ID NO: 94, SEQ ID NO: 95, SEQ ID NO: 96, SEQ ID NO: 97, SEQ ID NO: 98, and SEQ ID NO: 99; or
   SEQ ID NO: 100, SEQ ID NO: 101, SEQ ID NO: 102, SEQ ID NO: 103, SEQ ID NO: 104, and SEQ ID NO: 105.

16. The antibody or fragment thereof of embodiment 15, comprising SEQ ID NO: 8 and SEQ ID NO: 9.

17. The antibody or fragment thereof of embodiment 15, comprising SEQ ID NO: 10 and SEQ ID NO: 11.

18. The antibody of embodiment 15, comprising 5D12 or 8F5.

19. The antibody or fragment thereof of any of embodiments 1-18 which is in the form of a whole antibody.

20. The antibody or fragment thereof of any one of embodiments 1-5, 7-13, or 15-17 which is in the form of a scFv.

21. A bi-specific antibody construct comprising a binding domain comprising an antibody fragment of any one of embodiment 1-5, 7-13, or 15-17.
22. The bi-specific antibody construct of embodiment 21, further comprising an immune cell activation epitope binding domain.
23. A chimeric antigen receptor (CAR) comprising a binding domain comprising an antibody fragment of any one of embodiments 1-5, 7-13, or 15-17, and an effector domain.
24. An scFV comprising a binding domain of (i) 5E10.7, 1H7, 12B12, 4H10, 11D5, 13E11, 11D11, 7E7, 5D12, 8F5, or 2D5; and (ii) an immune cell activator.
25. The scFV of embodiment 24, wherein the immune cell activator binding domain binds an epitope on CD3, CD28, or CD8.
26. The scFV of embodiment 24 wherein the immune cell activator binding domain comprises a CDR sequence of OKT3, OKT8, or 9D7.
27. The scFV of embodiment 24, comprising SEQ ID NO: 91.
28. An IgG-based bispecific antibody construct, comprising a binding domain of (i) 5E10.7, 1H7, 12B12, 4H10, 11D5, 13E11, 11D11, 7E7, 5D12, 8F5, or 2D5; and (ii) an immune cell activator.
29. The IgG-based bispecific antibody construct of embodiment 28, wherein the immune cell activator binding domain binds an epitope on CD3, CD28, or CD8.
30. The IgG-based bispecific antibody construct of embodiment 28, comprising SEQ ID NOs: 92 and 93.
31. A chimeric antigen receptor (CAR) comprising a binding domain of (i) 5E10.7, 1H7, 12B12, 4H10, 11D5, 13E11, 11D11, 7E7, 5D12, 8F5, or 2D5; and (ii) an effector domain.
32. The CAR of embodiment 23 or embodiment 31, comprising an effector domain from one or more of: 4-1BB, CD3ε, CD35, CD3ζ, CD27, CD28, CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, or PTCH2.
33. An antibody or binding-competent fragment thereof that binds a membrane-proximal epitope on CD33 that comprises at least one of residues 145-260 of SEQ ID NO: 36.
34. An anti-CD33 antibody or binding-competent fragment thereof essentially as described herein.
35. An immunoconjugate comprising an antibody, fragment, CAR, IgG-based bispecific antibody construct, or scFV of any of embodiments 1-35 conjugated to a cytotoxic agent.
36. A composition comprising an antibody, fragment, CAR, IgG-based bispecific antibody construct, scFV, or immunoconjugate of any of embodiments 1-36.
37. The composition of embodiment 36, further comprising a pharmaceutically acceptable excipient.
38. A method of treating a CD33-related disorder in a subject in need thereof, the method comprising administering a therapeutically amount of a composition of embodiment 36 or embodiment 37 to the subject, thereby treating the CD33-related disorder in the subject.
39. The method of embodiment 38, wherein the CD33-related disorder is a lymphoma or leukemia.
40. The method of embodiment 39, wherein the leukemia is acute myeloid leukemia (AML).

Example 1. Identification and Characterization of CD33-Specific Antibodies

FIGS. 4A-4C illustrate the expression (FIG. 4A, 4B) and characterization of two CD33$^{FL}$ specific (8F5 and 5D12) and one CD33$^{\Delta E2}$ specific (12B12) antibodies. Affinities for these antibodies (shown in FIG. 4C) were characterized by Biacore (Biacore, A&G Pharmaceutical, Inc., Columbia, MD) using purified antibodies and the corresponding soluble ectodomains. $K_D$ for 8F5 is 8 nM; $K_D$ for 12B12 is 8 nM, and $K_D$ for 5D12 is 112 µM.

Figure 5:
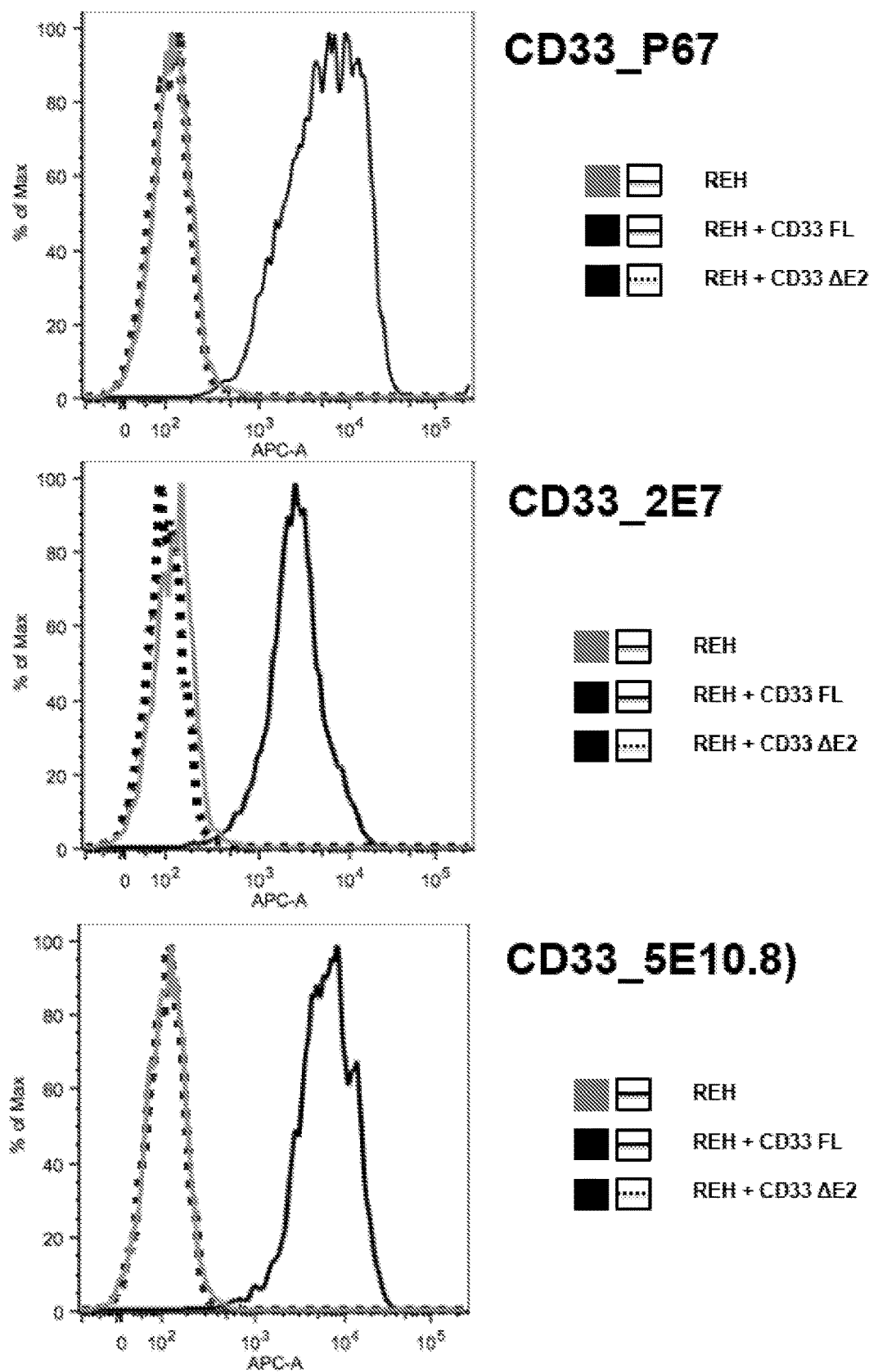
FIG. 5. CD33 V-set domain binding antibodies. Flow cytometry binding assay showing antibodies that bind CD33$^{FL}$ compared with P67.6. Most, if not all, therapeutic and diagnostic antibodies are specific for the membrane distal V-set Ig-like domain of CD33 and therefore do not recognize the C2-set Ig-like domain and consequently also do not recognize the CD33$^{\Delta E2}$ isoform. REH=human CD33$^{neg}$ lymphoid cells.

Most, if not all, therapeutic and diagnostic antibodies available prior to the developments are specific for the membrane distal V-set Ig-like domain of CD33 and therefore do not recognize the C2-set Ig-like domain and consequently also do not recognize the CD33$^{\Delta E2}$ isoform. FIG. 5 illustrates flow cytometry binding assay characterization of full-length CD33-specific antibodies (that is, which bind CD33$^{FL}$), compared with the commercially available anti-CD33 antibody P67.6.

REH=human CD33$^{neg}$ lymphoid cells.

Figure 6:
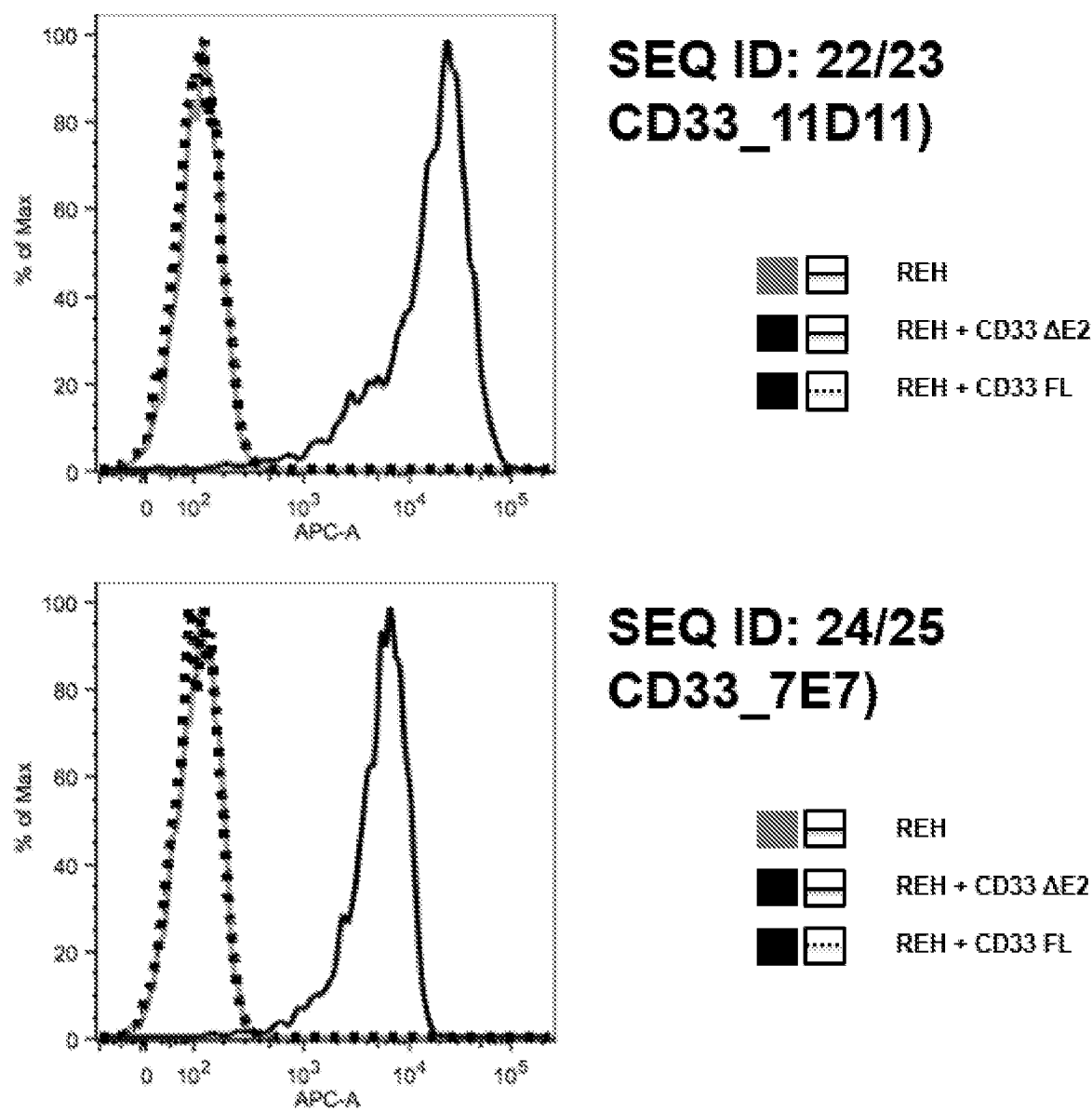
FIG. 6. CD33 C2-set Ig-like domain specific CD33 antibodies. Binding assay showing novel antibodies that bind the CD33$^{\Delta E2}$ isoform and not CD33$^{FL}$. Antibodies specific for CD33$^{\Delta E2}$ have not been described reliably in the literature and will be useful for determining expression profiles of this isoform across healthy and diseased individuals. REH=human CD33$^{neg}$ lymphoid cells.

FIG. 6 illustrates flow cytometry binding assay characterization of CD33$^{\Delta E2}$_specific 0033 antibodies. The binding assay shows novel antibodies (11D11 and 7E7) that bind the CD33$^{\Delta E2}$ isoform and not CD33$^{FL}$. Antibodies specific for CD33$^{\Delta E2}$ have not previously been described reliably in the literature. The herein-described CD33$^{\Delta E2}$ specific antibodies will be useful, including for determining expression profiles of this isoform across healthy and diseased individuals. REH =human CD33$^{neg}$ lymphoid cells.

Figure 7:
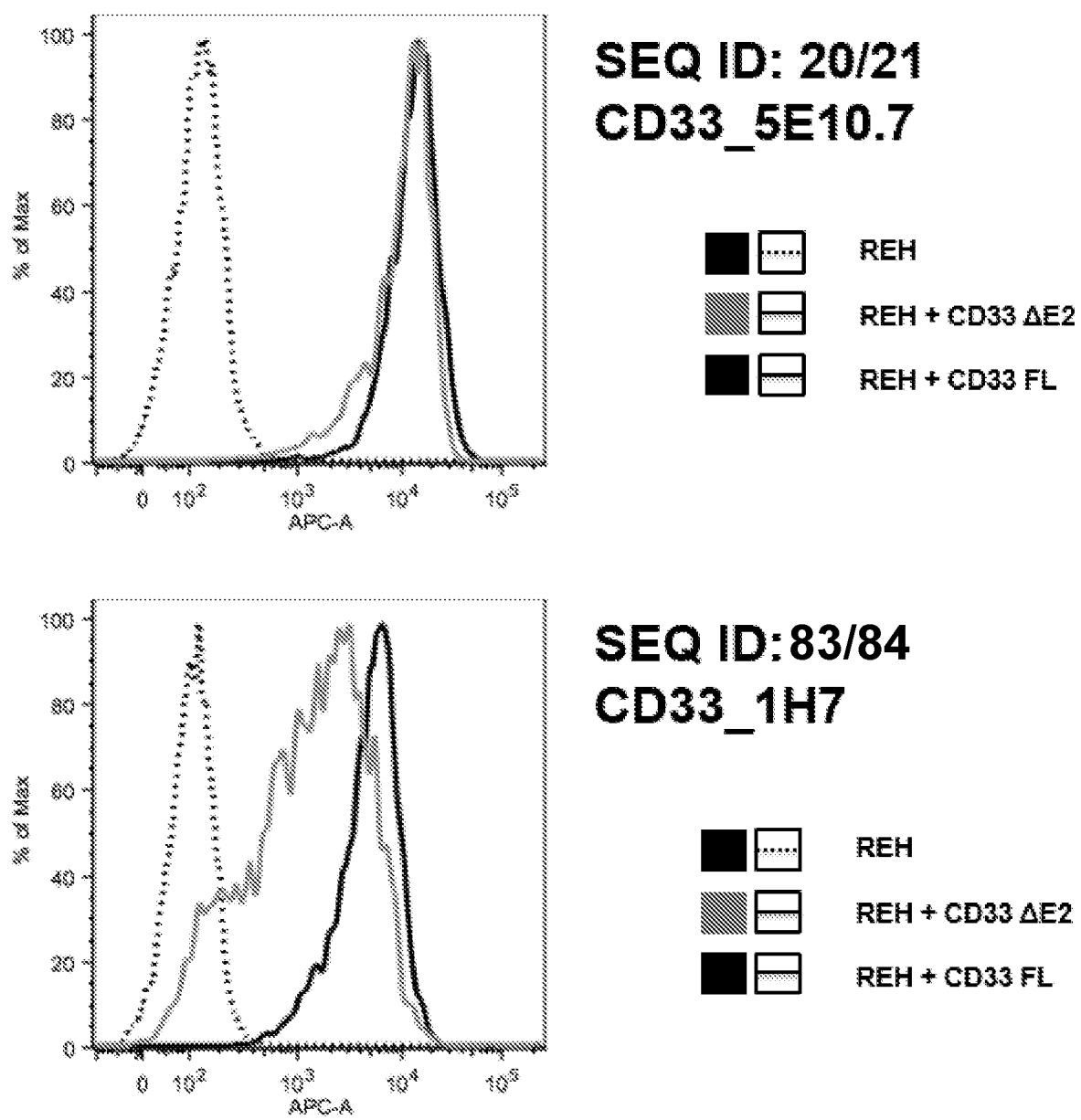
FIG. 7. "Pan-specific" CD33 antibody. Binding assay showing novel antibodies that bind the C2-set Ig-like domain and therefore recognize both CD33$^{FL}$ and CD33$^{\Delta E2}$, as well as other naturally occurring splice isoforms (e.g., CD33$^{\Delta 7a}$, CD33$^{\Delta E2,7a}$). These antibodies and others with similar specificities are superior to those described in the literature because (1) they can target a higher density of CD33 antigen and (2) they bind a membrane proximal epitope which is predicted to yield enhanced antibody effector functions, for example, increased activity of immune cell-engaging bispecific antibodies and chimeric antigen receptor (CAR)-modified immune cells, which could also benefit from a membrane proximal epitope. REH=human CD33$^{neg}$ lymphoid cells.

FIG. 7 illustrates flow cytometry binding assay characterization of pan specific CD33 antibodies. The binding assay shows novel antibodies (5E10.7 and 1H7) that bind the C2-set Ig-like domain and therefore recognize both CD33$^{FL}$ and CD33$^{\Delta E2}$. These antibodies and others with similar specificities are superior to those described in the literature because (1) they can target a higher density of CD33 antigen and (2) they bind a membrane proximal epitope which is predicted to yield, for example, more potent bispecific immune cell engaging antibodies and CAR-modified immune cells, which can also benefit from a membrane proximal epitope. REH=human CD33$^{neg}$ lymphoid cells.

Figure 3A:
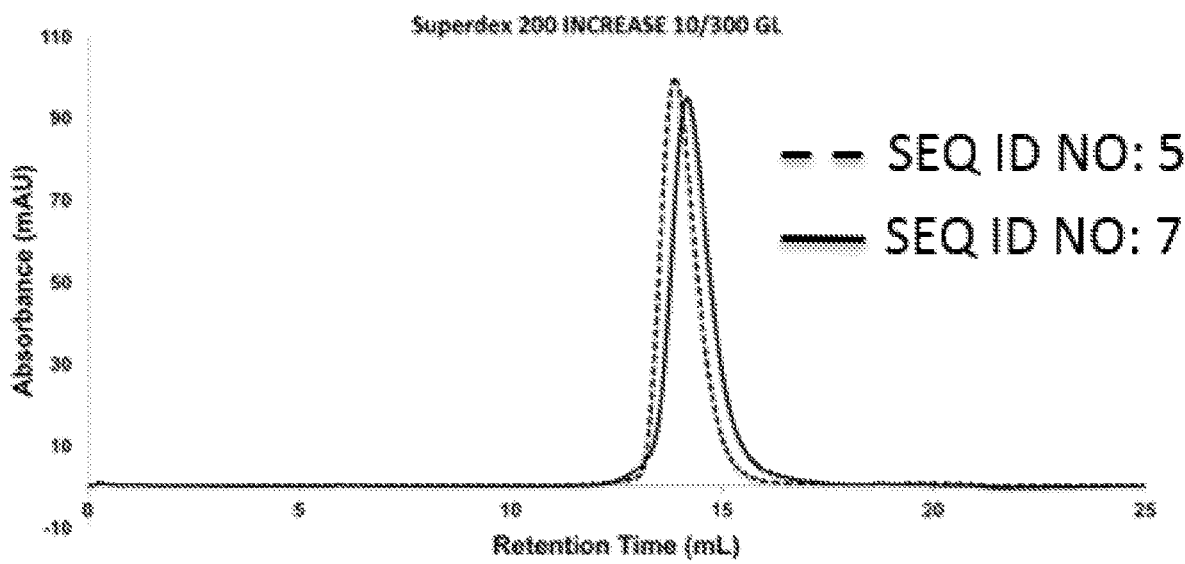
FIGS. 3A-3D. $CD33^{\Delta E2}$ Neoepitope. Extracellular versions of $CD33^{FL}$ (SEQ ID NO: 5) and the $CD33^{\Delta E2}$ (SEQ ID NO: 7) isoforms were expressed, purified, and characterized. Size exclusion chromatography (FIG. 3A) and SDS-PAGE gel (FIG. 3B) analyses show the purified recombinant proteins.
Figure 3B:
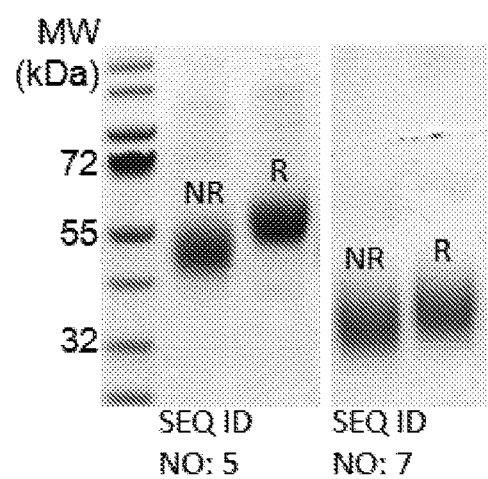
Figures 3C, 3D:
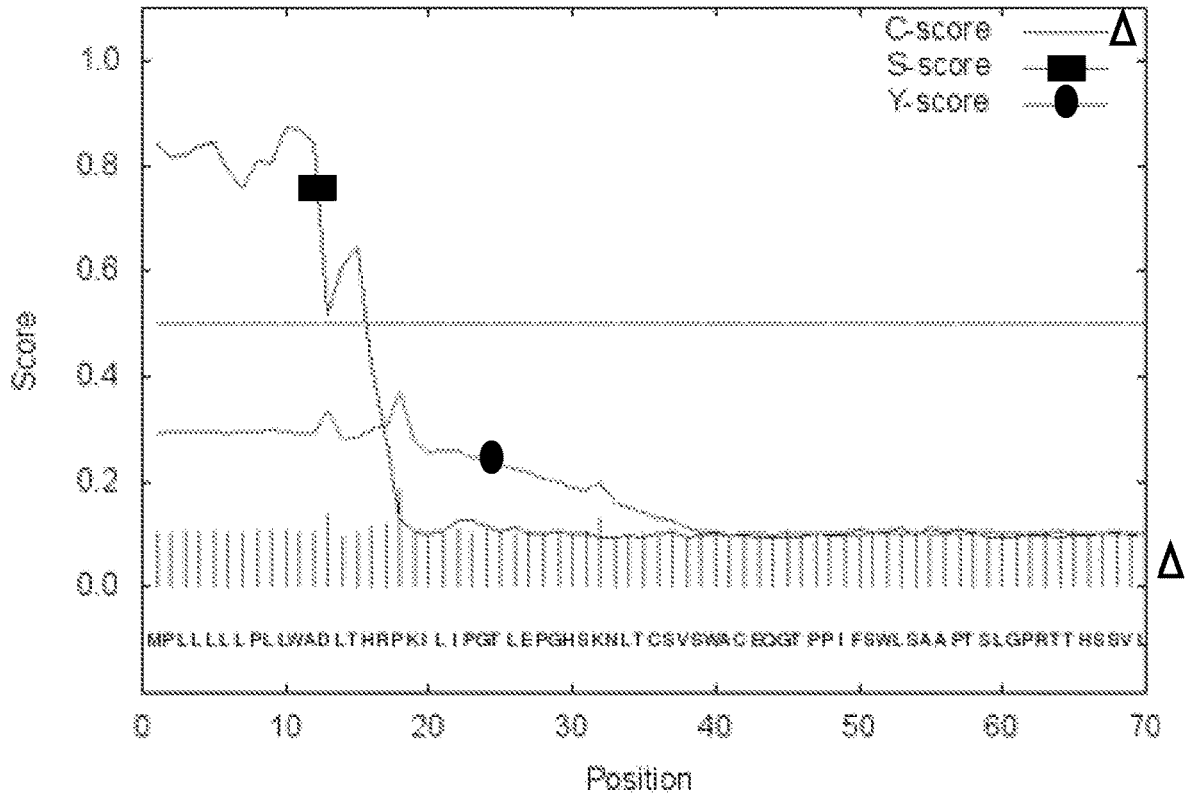

Example 2. Expression and Purification of CD33$^{FL}$ and CD33$^{\Delta E2}$ Isoforms Extracellular versions of CD33$^{FL}$ (SEQ ID NO: 5) and the CD33$^{\Delta E2}$ (SEQ ID NO: 7) isoforms were expressed, purified, and characterized. Size exclusion chromatography (FIG. 3A) and SDS-PAGE gel (FIG. 3B) show the purified recombinant proteins. FIG. 3C shows signal peptide prediction using the program SignalP (freely available on the World Wide Web at cbs.dtu.dk/services/SignalP/). This result highlights the fact that the leader peptide present on the CD33$^{\Delta E2}$ isoform is not recognizable as such (using SignalP) and therefore this portion of the isoform may represent a novel neoepitope. The sequence shown corresponds to positions 1-70 of SEQ ID NO: 2. FIG. 3D shows peptide sequences (SEQ ID NOs: 28-31) derived from the N-terminus of the recombinant CD33$^{\Delta E2}$ isoform as determined by mass spectrometry. Recombinant protein was reduced, alkylated and trypsinized to generate the data set.

Figure 8:
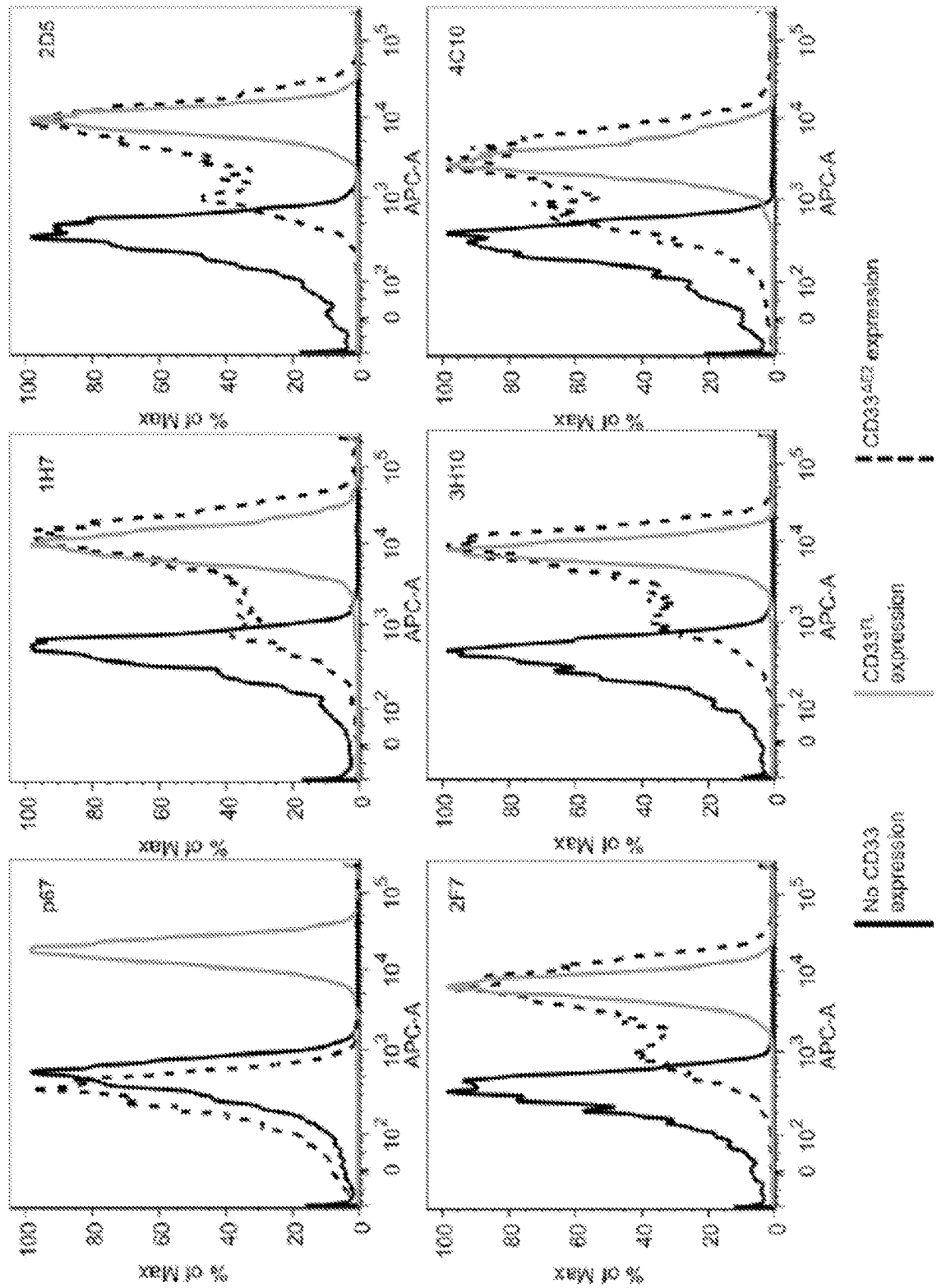
FIG. 8. Binding of commercial V-set domain CD33 antibody (P67.6) as well as in-house-made C2-set domain CD33$^{PAN}$ antibodies to parental (CD33-negative) acute leukemia cell line (REH cells; black) and REH sublines expressing either CD33$^{FL}$ (grey) or CD33$^{\Delta E2}$ (dashed).
Figure 9:
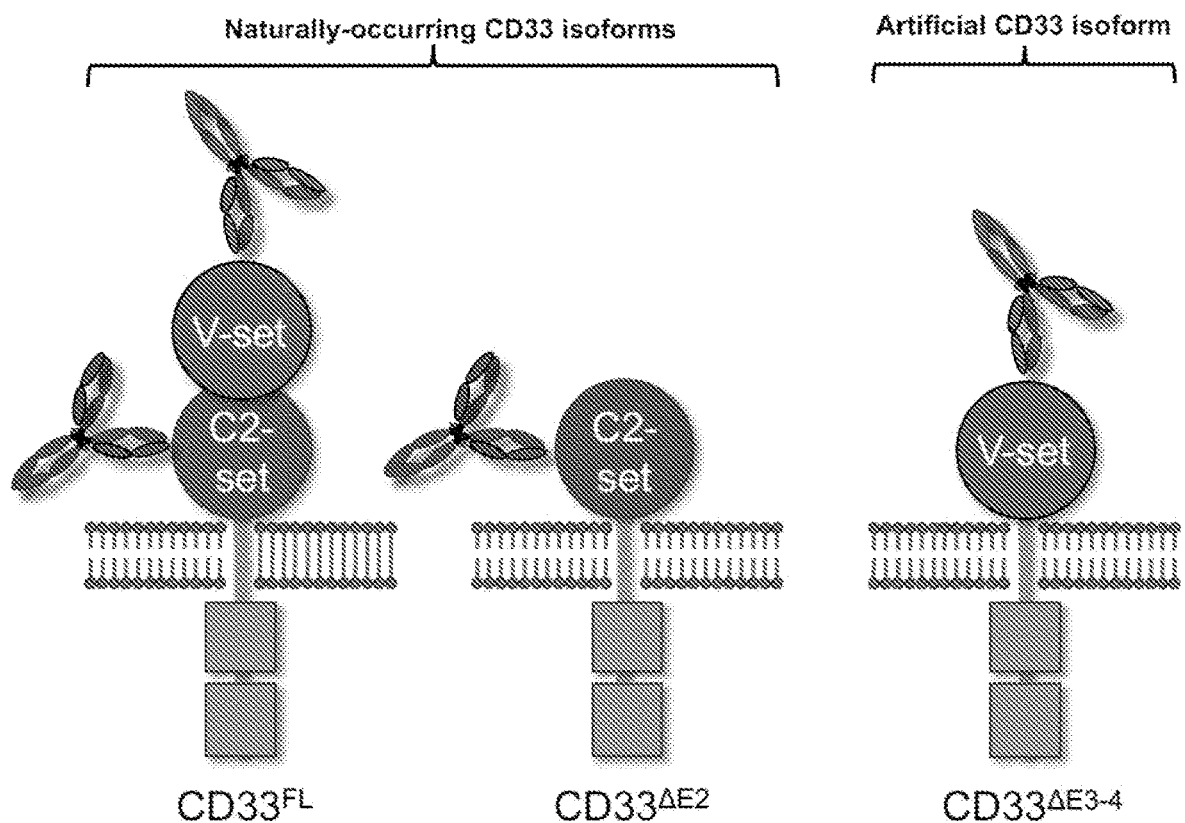
FIG. 9. Schemes of naturally-occurring CD33 isoforms and artificial CD33 proteins to characterize CD33 antibodies in this application.

Example 3. Identification and Characterization of Additional CD33-Specific Antibodies A series of C2-set domain-directed CD33 antibodies in mice were generated. As shown in FIG. 8, in REH (human CD33neg lymphoid) cells and sublines engineered to express CD33$^{\Delta E2}$ or CD33$^{FL}$, five antibody clones (1H7, 2D5, 2F7, 3H10, and 4C10) recognized both CD33$^{\Delta E2}$ and CD33$^{FL}$ and are therefore believed to bind the C2-set domain. Additional studies with 1 H7 showed lack of binding to cells displaying an artificial CD33 molecule that contains only the V-set domain (CD33$^{\Delta E3-4}$; FIG. 9), confirming C2-set domain binding. CD33$^{\Delta E3-E4}$ is an artificial, lab-generated CD33 molecule that contains only the V-set but not C2-set domain. This bring the V-set domain closer to the membrane and enables use of a V-set antibody (like AMG 330) to show that membrane proximal binding of therapeutic CD33 antibodies is superior to membrane-distal binding. This data supports the assertion that C2-set Ig-like domain antibodies (as describes herein, whether they bind only the C2-set domain alone or in the presence of V-set domain) have conceptual advantages over previously available antibodies.

Figure 10:
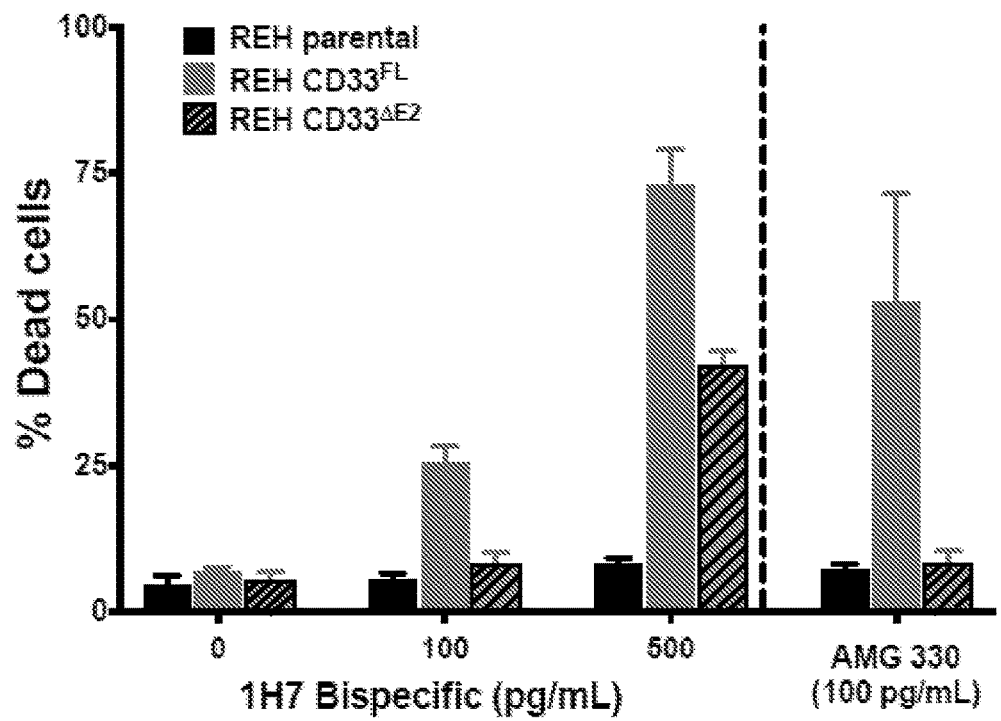
FIG. 10. Cytotoxicity of CD33$^{PAN}$/CD3 bispecific antibody and AMG 330 (a previously published investigational V-set domain-directed CD33/CD3 bispecific T-cell engager) on parental (CD33-negative) REH cells (black) and REH cells transduced with CD33$^{FL}$ (grey) or CD33$^{\Delta E2}$ (cross hatched); mean±SEM (n=4).

Studies with a bispecific 1H7 antibody showed that CD33$^{PAN}$ antibodies indeed can exert cytotoxic properties against cells expressing CD33$^{\Delta E2}$ and CD33$^{FL}$, whereas the V-set domain-directed CD33/CD3 bispecific T-cell engager AMG 330 (Laszlo et al. Blood. 123(4): 554-561, 2014; Harrington et al. PLoS One. 10(8): e0135945, 2015) was only effective against CD33$^{FL}$-expressing cells (FIG. 10).

Figure 11:
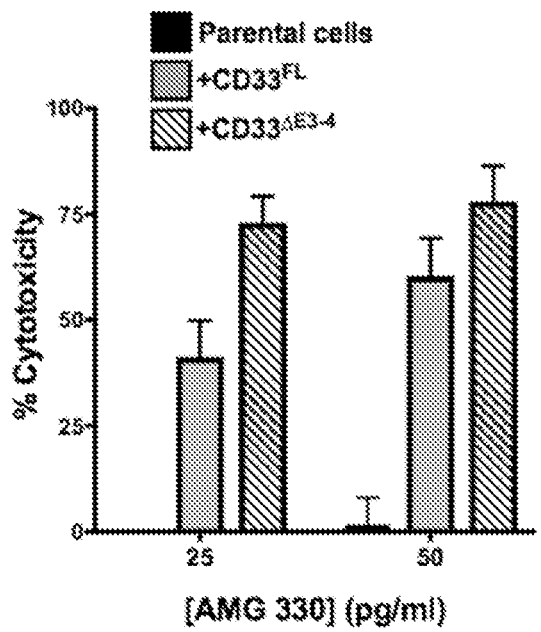
FIG. 11. Cytotoxicity of CD33$^{FL}$/CD3 bispecific antibody AMG 330 on parental (CD33-negative) RS4;11 cells (black) and RS4;11 cells transduced with CD33$^{FL}$ (grey) or CD33$^{\Delta E3}$-4 (cross hatched); mean±SEM (n=3).

The importance of membrane proximity for therapeutic efficacy was initially suggested by data with CD20, CD22, CD25, and EpCAM antibodies (Cleary et al., J Immunol. 198(10): 3999-4011, 2017; Lin, Pharmgenomics Pers Med. 3: 51-59, 2010; Haso et al., Blood. 121(7):1165-1174, 2013; Bluemel etal., Cancer Immunol Immunother. 59(8): 1197-1209, 2010). Without being bound by any one theory, membrane-proximal targeting of CD33 can enhance the cytolytic activity of CAR T-cells. Consistent with this, preliminary studies in parental (CD33$^{neg}$) human acute lymphoblastic RS4;11 cells and sublines engineered to express either CD33$^{FL}$ or CD33$^{\Delta E3}$-4 at the same cell surface density indicate greatly enhanced cytolytic activity AMG 330 (FIG. 11).

Example 4. CAR with Selected CD33 Specificity

This example describes representative methods that can be used to produce CD33 CAR T-cells.

A lentiviral CAR construct can be assembled using scFv(s) from anti-CD33 antibodies described in the disclosure fused to, for instance, a CD28 transmembrane sequence and containing both 4-1BB and CD3 zeta chain signaling domains. The presence of these components will create a functional CAR receptor with CD33$^{PAN}$ specificity (where a CD33$^{PAN}$ antibody is used, though other anti-CD33 antibodies described herein can be used for different specificities). Lentiviral vectors can subsequently be prepared from these CD33 CAR constructs by transfection of the env, gag, pol and rev plasmids in a packaging cell line and tittered for functional assays.

Example 5. In Vitro Assessment of CD33$^{PAN}$ CAR T-Cells-Directed Cytotoxicity Against AML and Myeloma Cells This example describes representative methods that can be used for assessing, in vitro, the cytotoxicity of CD33$^{PAN}$ CAR T-cell.

Once a CD33$^{PAN}$-directed CAR construct has successfully been created and expression confirmed, the ability of engineered T-cells expressing that construct to specifically kill CD33 expressing leukemia and myeloma cells will be tested, using a panel of acute leukemia and myeloma cell lines both as parental cells and sublines engineered to express either CD33$^{\Delta E2}$ or CD33$^{FL}$. Cell killing assays can be used to show efficacy of disclosed CARs using an assay to demonstrate CAR-T effectiveness, where target cells are adhered as a monolayer within individual wells of a 96-well plate. Each well contains microscopic electrodes covering the well floor with intact cells disrupting a small electrical current. This electrical current is then restored as cells are killed either through incubation with effector CAR modified T-cells at various concentrations or positive controls such as addition of Triton-X. This assay replaces previous versions which utilize flow cytometry-based analysis of cell viability markers or chromium release assays as a single endpoint readout. Alternatively, the assay allows for continuous real-time kinetics of cell killing over the course of days to directly compare head-to-head different constructs or tumor lines to one another and the relative rate of cell killing. Optimal concentration of tumor seeding can be empirically determined for each target line, and then growth kinetics can be tracked. Once standard curves have been established, modified T-cells from human donors expressing the CD33 CAR construct of interest can be added to target wells at concentrations ranging from 1:0.5 up to 1:20 (target:effector cell ratios) to observe for specific target cell killing as compared to either mock transduced or off-target modified T-cells. As confirmation of effective cell killing, secondary readout methods can be used to confirm cell cytotoxicity. including trypan blue exclusion and viability stain by flow cytometry, as well as microscopic imaging of effector wells.

Example 6. In Vivo Assessment of Anti-Leukemia Activity of CD33$^{PAN}$ CAR T-Cells using the immunodeficient mouse model This example describes representative methods that can be used for assessing, in vivo, the anti-leukemia activity of CD33$^{PAN}$ CAR T-cells.

Using guidelines previously established for the generation of an immunotherapy humanized mouse model (Haworth et al., Mol Ther Methods Clin Dev. 6: 17-30, 2017), neonate mice can first be infused with 1×10$^6$ CD34+HSPCs. Two different donor sources of HSPCs can be used for each experimental condition to account for donor-to-donor engraftment variability. Blood collection can occur every other week and analyzed by flow cytometry for peripheral human cell engraftment and lineage development. After T-cell development is observed in the peripheral blood of mice typically around 14-16 weeks post infusion, a portion of the mice can be sacrificed for total T-cell collection from blood and lymphoid compartments. Collected CD3+can be stimulated with CD3/CD28 beads for 3-5 days and transduced with the corresponding CD33$^{PAN}$ CAR lentiviral constructs. The first cohort of mice can include 4 mice per donor and can receive 1×10$^6$ CAR-transduced CD3+cells to verify that these cells can persist in the animals for several weeks without inducing GvHD.

Once successful, in cohorts 2 and 3 mice can then be divided into 3 different groups: i) mock mice receiving no cell injections, ii) mice receiving tumor cells alone, iii) mice receiving both tumor and modified T-cells. For this purpose, tumor cell lines can be generated that are transduced with a firefly luciferase to allow in vivo tumor burden monitoring. These tumor cells can be administered through intravenous injection 2-5 days prior to modified T-cell infusion in order to better mimic the clinical situation where tumor cells are already present in the patient. After infusion, mice will be monitored for both tumor burden using direct in vivo luciferase imaging. Additionally, peripheral blood will be analyzed by quantitative PCR to measure modified T-cell levels after infusion. T-cell subset composition will also be determined by flow cytometry phenotypic analysis.

The anti-leukemia activity of CD33$^{PAN}$ CAR CD3+cells will be verified by overall survival and by dissemination/growth of the tumor cell burden. At time of necropsy, animals can be sacrificed and multiple lymphoid tissues can be collected for analysis including bone marrow, spleen, and thymus. The frequency of modified cells can be quantified in each tissue by flow cytometry and validated by PCR based TaqMan methods. Tissues can also be assessed using both flow cytometry and quantitative PCR for the presence of residual tumor cells using methods for specifically detecting the luciferase gene present in the tumor lines.

Example 7. Production of 1H7-Based Bi-Specific T-Cell Engaging Antibodies

This example describes the production of a CD33/CD3-directed scFv-based bi-specific T-cell engaging antibody and a CD33/CD3-directed IgG-based bi-specific T-cell engaging antibody.

Representative bi-specific T-cell engaging antibodies based on the 1H7 antibody were produced and expressed. Protein sequences were reverse-translated and codon optimized for gene synthesis. The plasmids encoding the genetic expression constructs were packaged into lentiviral particles, which were then used to transduce HEK293F producer cells. The proteins were secreted into the culture medium and purified using NiNTA affinity chromatography. The proteins were then further purified by size exclusion chromatography and quantitated using standard techniques.

Figure 12A:
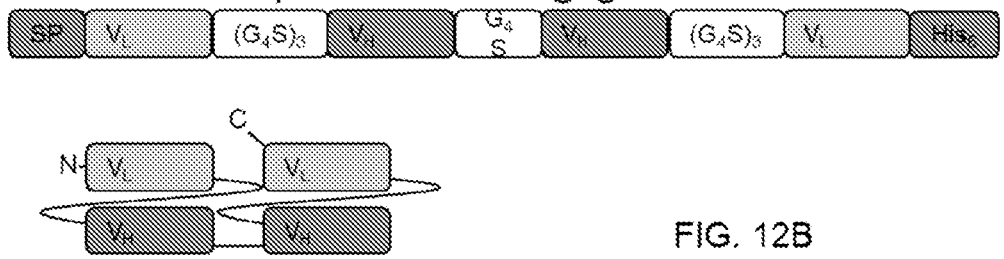
FIG. 12A-12B. Schematic showing the format of the 1H7 bispecific antibody T-cell engager (FIG. 12A), along with the amino acid sequence and SDS-PAGE gel of purified product (FIG. 12B).
Figure 12B:
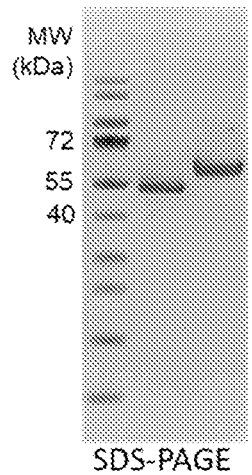

FIG. 12A illustrates the structure of a representative scFv-based bispecific T-cell engaging antibody (linear and folded). FIG. 12B is a SDS-PAGE gel showing expression of the 1 H7-CD3 bispecific T-cell engaging antibody shown in SEQ ID NO: 91; the 1H7 antibody sequences used to build this construct are SEQ ID NOs: 83 and 84. In SEQ ID NO: 91, positions 21-259 correspond to the scFv for 1H7, in VL-VH orientation separated by a linker (positions 128-142); and positions 165-513 correspond to the scFv for anti-CD3 (derived from AMG330; including a linker at positions 390-404).

Figure 13A:
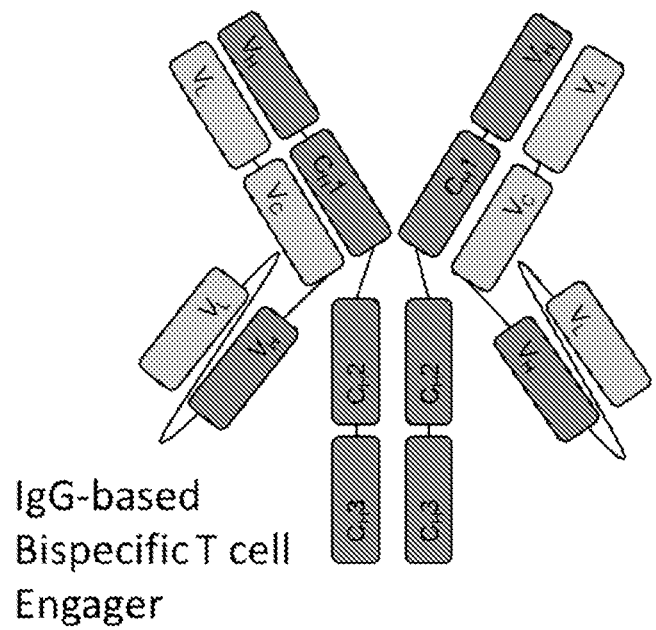
FIG. 13A-13B. Schematic showing the format of the 1H7 Ig-bispecific antibody T-cell engager (FIG. 13A), along with the amino acid sequence of the light and heavy chains and SDS-PAGE gel of purified product (FIG. 13B).
Figure 13B:
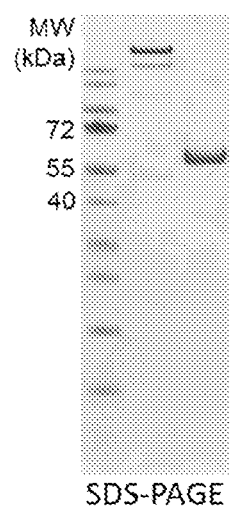

FIG. 13A illustrates the folded and assembled structure of a representative IgG-based bispecific T-cell engaging antibody construct. FIG. 13B is a SDS-PAGE gel showing expression of the 1H7-CD3 bispecific T-cell engaging antibody shown in SEQ ID NOs: 92 and 93; the 1H7 antibody light and heavy chain sequences used to build these constructs are SEQ ID NOs: 84 and 83 (respectively). In SEQ ID NO: 92, positions 21-234 correspond to the light chain for 1H7; positions 250-498 correspond to the scFv for anti-CD3 (derived from AMG330, as above); a linker separates these segments. In SEQ ID NO: 93, the heavy chain for 1H7 is positions 21-467.

Example 8. Characterization of Antibody Binding to CD33 Signal Peptides in Hybrid Proteins This example describes characterization of antigen binding to neoepitope(s) in CD33$^{ΔE2}$ formed due to a retained signal peptide on the amino terminal of CD33$^{ΔE2}$.

Hybrid proteins were produced wherein the signal peptide of native CD33 was swapped with that of CD33$^{ΔE2}$ and vice versa. The binding of two antibodies, 11D5 and 13E11, to these hybrid proteins was then analyzed.

FIG. 14A is a sequence illustration of the C-terminal end (including the signal peptide) of native CD33$^{FL}$ CD33$^{ΔE2}$ a hybrid protein including the signal peptide of CD33$^{FL}$ fused to the C-terminal end of CD33$^{ΔE2}$ (FL SP on CD33$^{ΔE2}$), and a hybrid protein including the signal peptide of CD33$^{ΔE2}$ fused to the C-terminal end of 0033$^{FL}$ (ΔE2 SP on CD33$^{FL}$). The upper section of FIG. 14A shows the sequences before signal peptide cleavage; the lower section, after such cleavage (as proposed). Signal peptide cleavage are sites indicated with filled triangle. Predicted possible signal peptide cleavage sites indicated with dotted empty triangles. The sequence comprising a 13E11 epitope is indicated. In order, the sequences shown in FIG. 14A correspond to: residues 1-44 of SEQ ID NO: 1 (exon 1=positions 1-12);
residues 1-39 of SEQ ID NO: 2 (exon 1=positions 1-12);
SEQ ID NO: 156 (exon 1=positions 1-12);
SEQ ID NO: 157 (exon 1=positions 1-12);
residues 18-44 of SEQ ID NO: 1;
residues 1-39 of SEQ ID NO: 2 (exon 1=positions 1-12);
residues 140-166 of SEQ ID NO: 1 (which is also 13-39 of SEQ ID NO: 2); and
SEQ ID NO: 157 (exon 1=positions 1-12).

Figure 14B:
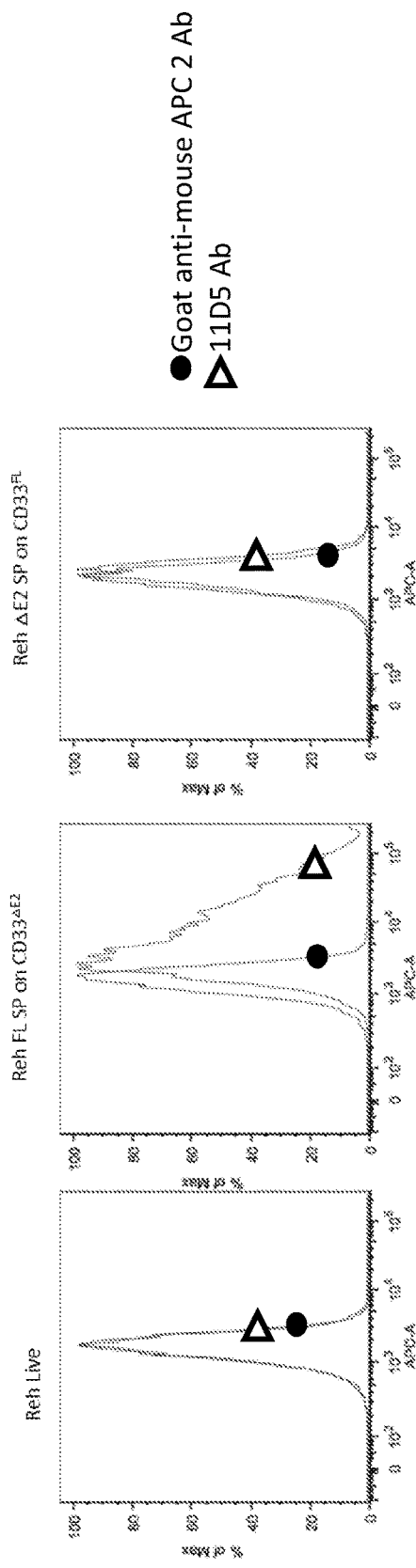
Figure 14C:
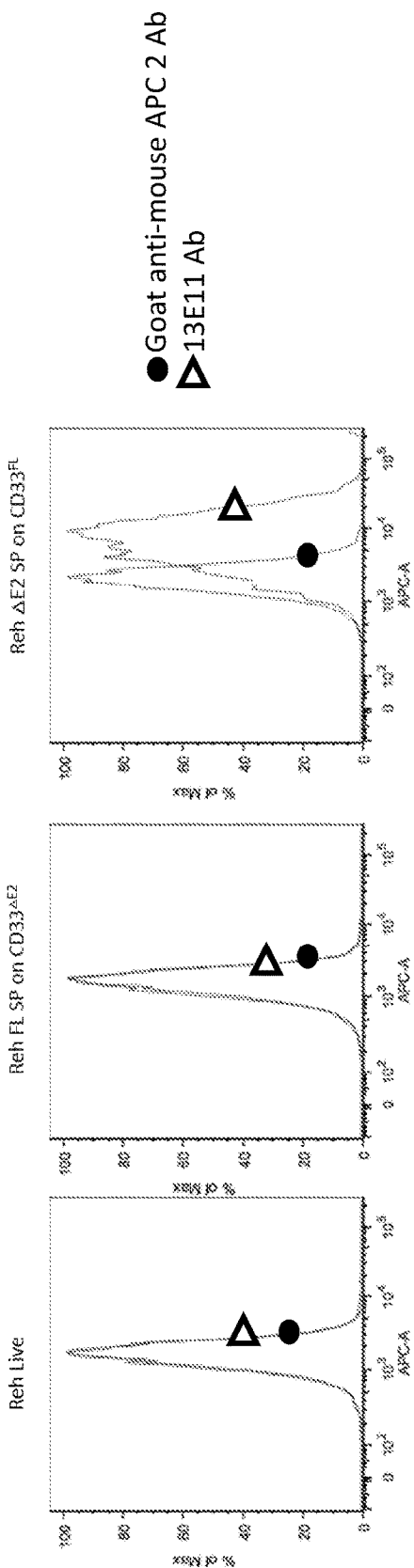

FIG. 14B-14C show REH cells engineered to express hybrid CD33 proteins. 11D5, a CD33$^{ΔE2}$-specific antibody that cannot bind to CD33$^{FL}$ can bind to CD33$^{ΔE2}$ in the absence of the ΔE2 SP, and the signal peptide of CD33$^{ΔE2}$ fused to the C-terminal end of CD33$^{FL}$ (ΔE2 SP on CD33$^{FL}$) does not confer 11D5 binding. This indicates that 11D5 binds to CD33$^{ΔE2}$ independent of the ΔE2 SP (FIG. 14B). 13E11, a CD33$^{ΔE}$-specific antibody that cannot bind to CD33$^{FL}$ also cannot bind to CD33$^{ΔE2}$ in the absence of the ΔE2 SP. Furthermore, the signal peptide of CD33$^{ΔE2}$ fused to the C-terminal end of CD33$^{FL}$ (ΔE2 SP on CD33$^{FL}$) does confer 11D5 binding to CD33$^{FL}$ indicating that 13E11 binds to an epitope within the ΔE2 SP.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in binding between an antibody and antigen as compared to the values depicted in the accompanying FIGS.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; ±18% of the stated value; 17% of the stated value; 16% of the stated value; ±15% of the stated value; 14% of the stated value; ±13% of the stated value; 12% of the stated value; 11% of the stated value; 10% of the stated value; 9% of the stated value; 8% of the stated value; 7% of the stated value; ±6% of the stated value; 5% of the stated value; 4% of the stated value; ±3% of the stated value; 2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

---

```
Supporting Sequences

SEQ ID NO: 1 is the amino acid sequence of human full-length CD33 hsCD33-mmFc used as
an immunogen for human FL (MDT000208):
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGGGSGCKPCICTVPEVSSVFIFPPKPKDVLTITLTPKVTCVVVDISKDDPEVQFSWFVDDVEVH
TAQTQPREEQFNSTFRSVSELPIMHQDWLNGKEFKCRVNSAAFPAPIEKTISKTKGRPKAPQV
YTIPPPKEQMAKDKVSLTCMITDFFPEDITVEWQWNGQPAENYKNTQPIMNTNGSYFVYSKLN
VQKSNWEAGNTFTCSVLHEGLHNHHTEKSLSHSPGK
```

-continued

| Supporting Sequences |
|---|

SEQ ID NO: 2 is the amino acid sequence of the human ΔE2 version of CD33 (CD33$^{ΔE2}$) with a mouse Fc domain (MDT000209; hsCD33_ΔE2-mmFc; Immunogen for human ΔE2):
MPLLLLLPLLWADLTHRPKILIPGTLEPGHSKNLTCSVSWACEQGTPPIFSWLSAAPTSLGPRTT
HSSVLIITPRPQDHGTNLTCQVKFAGAGVTTERTIQLNVTYVPQNPTTGIFPGDGSGKQETRAG
GGSGCKPCICTVPEVSSVFIFPPKPKDVLTITLTPKVTCVVVDISKDDPEVQFSWFVDDVEVHTA
QTQPREEQFNSTFRSVSELPIMHQDWLNGKEFKCRVNSAAFPAPIEKTIS SEQ ID NO: 3 is the amino acid sequence of *Macaca fascicularis* CD33$^{FL}$ with a mouse Fc domain (mfCD33-mmFc; MDT000210; Immunogen for cyno FL):
MPLLLLLPLLWAGALAMDPRVRLEVQESVTVQEGLCVLVPCTFFHPVPYHTRNSPVHGYWFRE
GAIVSLDSPVATNKLDQEVQEETQGRFRLLGDPSRNNCSLSIVDARRRDNGSYFFRMEKGSTK
YSYKSTQLSVHVTDLTHRPQILIPGALDPDHSKNLTCSVPWACEQGTPPIFSVVMSAAPTSLGLR
TTHSSVLIITPRPQDHGTNLTCQVKFPGAGVTTERTIQLNVSYASQNPRTDIFLGDGSGRKARK
QGGGSGCKPCICTVPEVSSVFIFPPKPKDVLTITLTPKVTCVVVDISKDDPEVQFSWFVDDVEV
HTAQTQPREEQFNSTFRSVSELPIMHQDWLNGKEFKCRVNSAAFPAPIEKTISKTKGRPKAPQ
VYTIPPPKEQMAKDKVSLTCMITDFFPEDITVEWQWNGQPAENYKNTQPIMNTNGSYFVYSKL
NVQKSNWEAGNTFTCSVLHEGLHNHHTEKSLSHSPGK SEQ ID NO: 4 is the amino acid sequence of the extracellular domain of mouse CD33$^{FL}$ where the C2-set Ig-like domain from mouse has been replaced with the C2-set Ig-like domain from human CD33, combined with a Fc region from human IgG1 (mmCD33_Vset-mmCD33_C2set-hsCD33_Fc_hsIgG1; MDT000524; Immunogen for human ΔE2):
MLWPLPLFLLCAGSLAQDLEFQLVAPESVTVEEGLCVHVPCSVFYPSIKLTLGPVTGSWLRKGV
SLHEDSPVATSDPRQLVQKATQGRFQLLGDPQKHDCSLFIRDAQKNDTGMYFFRVVREPFVR
YSYKKSQLSLHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGSEPKSSDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK SEQ ID NO: 5 is the amino acid sequence of the extracellular domain of CD33$^{FL}$ with a 6-histidine-avidin tag (hsCD33-His-Avi; MDT000235; Screening Reagent):
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGSHHHHHHGSGLNDIFEAQKIEWHE SEQ ID NO: 7 is the amino acid sequence of the extracellular domain of CD33$^{ΔE2}$ with a 6-histidine-avidin tag (hsCD33_ΔE2-His-Avi; MDT000239; Screening Reagent):
MPLLLLLPLLWAGALAMDPRVRLEVQESVTVQEGLCVLVPCTFFHPVPYHTRNSPVHGYWFRE
GAIVSLDSPVATNKLDQEVQEETQGRFRLLGDPSRNNCSLSIVDARRRDNGSYFFRMEKGSTK
YSYKSTQLSVHVTDLTHRPQILIPGALDPDHSKNLTCSVPWACEQGTPPIFSWMSAAPTSLGLR
TTHSSVLIITPRPQDHGTNLTCQVKFPGAGVTTERTIQLNVSYASQNPRTDIFLGDGSGRKARK
QGSHHHHHHGSGLNDIFEAQKIEWHE SEQ ID NO: 7 is the amino acid sequence of hsCD33_ΔE2-His-Avi Screening Reagent (MDT000239):
MPLLLLLPLLWADLTHRPKILIPGTLEPGHSKNLTCSVSWASEQGTPPIFSWLSAAPTSLGPRTT
HSSVLIITPRPQDHGTNLTCQVKFAGAGVTTERTIQLNVTYVPQNPTTGIFPGDGSGKQETRAG
SHHHHHHGSGLNDIFEAQKIEWHE SEQ ID NO: 8 is the amino acid sequence of the light chain of IgG2a anti-CD33 antibody 5D12 (Ab_CD33_5D12_mmIgG2a_Light Chain; MDT000444), which is specific for CD33$^{FL}$:
METDTLLLWVLLLWVPGSTGDIKMTQSPSSIYASLGERVTINCKASQDIKSYLSWYQQKPWKSP
KTLIYYATTLADGVPSRFSGSGSGQDYSLTISSLESDDTATYYCLHHGESPWTFGEGTKLEIKR
ADAAPTVSIFPPSSEQLTSGGASVVCFLNNFYPKDINVKWKIDGSERQNGVLNSWTDQDSKDS
TYSMSSTLTLTKDEYERHNSYTCEATHKTSTSPIVKSFNRNEC SEQ ID NO: 9 is the amino acid sequence of the heavy chain of IgG2a anti-CD33 antibody 5D12 (Ab_CD33_5D12_mmIgG2a_Heavy Chain; MDT000445), which is specific for CD33$^{FL}$:
METDTLLLWVLLLWVPGSTGQVQLQQSGAEVVKPGASVKISCRASGYAFSNYWMNWVKQRP
GKGLEWIGQIYPGNFNTDYNGQFKGKATLTVDKSSNTAYMQLSSLTSEDSAVYFCARFFDFGA
YFTLDYWGQGTSVTVSSAKTTAPSVYPLAPVCGDTTGSSVTLGCLVKGYFPEPVTLTWNSGSL
SSGVHTFPAVLQSDLYTLSSSVTVTSSTWPSQSITCNVAHPASSTKVDKKIEPRGPTLKPCPPC
KCPAPNLLGGPSVFIFPPKIKDVLMISLSPIVTCVVVDVSEDDPDVQISWFVNNVEVHTAQTQTH
REDYNSTLRVVSALPIQHQDWMSGKEFKCKVNNKDLPAPIERTISKPKGSVRAPQVYVLPPPE
EEMTKKQVTLTCMVTDFMPEDIYVEWTNNGKTELNYKNTEPVLDSDGSYFMYSKLRVEKKNW
VERNSYSCSVVHEGLHNHHTTKSFSRTPGK SEQ ID NO: 10 is the amino acid sequence of the light chain of IgG2a anti-CD33 antibody 8F5 (Ab_CD33_8F5_mmIgG2a_Light Chain; MDT000446), which is specific for CD33$^{FL}$:
METDTLLLWVLLLWVPGSTGDIVMSQSPSSLPVSVGEKVTLSCKSSQSLLYSRNQYNFLAWYQ
QRPGQSPKLLIYWASTRESGVPDRFTGSGSGTDFTLTISSVKAEDLAVYYCQQYYSYPYTFGG
GTKLEIKRADAAPTVSIFPPSSEQLTSGGASVVCFLNNFYPKDINVKWKIDGSERQNGVLNSWT
DQDSKDSTYSMSSTLTLTKDEYERHNSYTCEATHKTSTSPIVKSFNRNEC -continued Supporting Sequences SEQ ID NO: 11 is the amino acid sequence of the heavy chain of IgG2a anti-CD33 antibody
8F5 (Ab_CD33_8F5_mmIgG2a_Heavy Chain; MDT000446), which is specific for CD33$^{FL}$:
METDTLLLWVLLLWVPGSTGEVKLVESGGGLVQPGGSLKLSCAASGFTFSDFYMYWVRQTPE
KRLEWVAFISNAGVTTYYPDTVEGRFTISRDNAKNTLYLQMSRLMSEDTAMYYCTKSDYDGAW
FPYWGQGTLVTVSAAKTTAPSVYPLAPVCGDTTGSSVTLGCLVKGYFPEPVTLTWNSGSLSSG
VHTFPAVLQSDLYTLSSSVTVTSSTWPSQSITCNVAHPASSTKVDKKIEPRGPTIKPCPPCKPA
PNLLGGPSVFIFPPKIKDVLMISLSPIVTCVVVDVSEDDPDVQISWFVNNVEVHTAQTQTHREDY
NSTLRVVSALPIQHQDWMSGKEFKCKVNNKDLPAPIERTISKPKGSVRAPQVYVLPPPEEEMT
KKQVTLTCMVTDFMPEDIYVEWTNNGKTELNYKNTEPVLDSDGSYFMYSKLRVEKKNWVERN
SYSCSVVHEGLHNHHTTKSFSRTPGK SEQ ID NO: 12 is the amino acid sequence of the light chain of IgG2b anti-CD33 antibody
12B12 (Ab_CD33_12B12_mmIgG2b_Light Chain; MDT000448), which is specific for CD33$^{\Delta E2}$:
METDTLLLWVLLLWVPGSTGDIVMTQAAFSNPVTLGTSASISCRSSQSLLHSNGITYLYWYLQK
PGQSPQLLIYQMSNLASGVPDRFSSSGSGTDFTLRISRVEAEDVGVYYCAQNLELPPTFGGGT
KLEIKRADAAPTVSIFPPSSEQLTSGGASVVCFLNNFYPKDINVKWKIDGSERQNGVLNSWTDQ
DSKDSTYSMSSTLTLTKDEYERHNSYTCEATHKTSTSPIVKSFNRNEC SEQ ID NO: 13 is the amino acid sequence of the heavy chain of IgG2b anti-CD33 antibody
12B12 (Ab_CD33_12B12_mmIgG2b_Heavy Chain; MDT000449), which is specific for CD33$^{\Delta E2}$:
METDTLLLWVLLLWVPGSTGEVQLQQSGTVLARPGASVKMSCKASGYTFTTYWMHWIKQSP
GQGLEWIGAIYPGNSDTSYNQKFKGKAKLTAVTSASTAYMELSSLTNEDSAVYYCEIYDGYHFI
YWGQGTTLTVSSAKTTPPSVYPLAPGCGDTTGSSVTLGCLVKGYFPESVTVTWNSGSLSSSV
HTFPALLQSGLYTMSSSVTVPSSTWPSQTVTCSVAHPASSTTVDKKLEPSGPISTINPCPPCKE
CHKCPAPNLEGGPSVFIFPPNIKDVLMISLTPKVTCVVVDVSEDDPDVQISWFVNNVEVHTAQT
QTHREDYNSTIRVVSTLPIQHQDWMSGKEFKCKVNNKDLPSPIERTISKIKGLVRAPQVYILPPP
AEQLSRKDVSLTCLVVGFNPGDISVEWTSNGHTEENYKDTAPVLDSDGSYFIYSKLNMKTSKW
EKTDSFSCNVRHEGLKNYYLKKTISRSPGK SEQ ID NO: 14 is the amino acid sequence of the light chain of anti-CD33 antibody 4H10,
isolated as IgG2a and reformatted as IgG1 for recombinant expression
(Ab_CD33_4H10_mmIgG1_Light Chain; MDT000492), which is specific for CD33$^{\Delta E2}$:
METDTLLLWVLLLWVPGSTGDVVMTQTPLTLSVTIGQPASISCKSSQSLLYSNGKTYLHWFLQR
PGQSPKRLIYLVSKLDSGVPDRFTGSGSGTDFTLKISRVEAEDLGVYYCVQGTHFPRTFGGGT
KLEIKADAAPTVSIFPPSSEQLTSGGASVVCFLNNFYPKDINVKWKIDGSERQNGVLNSWTDQD
SKDSTYSMSSTLTLTKDEYERHNSYTCEATHKTSTSPIVKSFNRNEC SEQ ID NO: 15 is the amino acid sequence of the heavy chain of anti-CD33 antibody 4H10,
isolated as IgG2a and reformatted as IgG1 for recombinant expression
(Ab_CD33_4H10_mmIgG1_Heavy Chain; MDT000491), which is specific for CD33$^{\Delta E2}$:
METDTLLLWVLLLWVPGSTGQVQLQQSGAELVRPGTSVKVSCKASGYAFTNYLIEWVKQRPG
QGLEWIGVIHPGNNSTSYNAKFRGKATLTADRSSSTAYMQLSSLTSEDSAVYFCARYGYDERN
AMDYWGQGTSVTVSSAKTTPPSVYPLAPGSAAQTNSMVTLGCLVKGYFPEPVTVTWNSGSLS
SGVHTFPAVLQSDLYTLSSSVTVPSSPRPSETVTCNVAHPASSTKVDKKIVPRDCGCKPCICTV
PEVSSVFIFPPKPKDVLTITLTPKVTCVVVDISKDDPEVQFSWFVDDVEVHTAQTQPREEQFNS
TFRSVSELPIMHQDWLNGKEFKCRVNSAAFPAPIEKTISKTKGRPKAPQVYTIPPPKEQMAKDK
VSLTCMITDFFPEDITVEWQWNGQPAENYKNTQPIMNTNGSYFVYSKLNVQKSNWEAGNTFT
CSVLHEGLHNHHTEKSLSHSPGK SEQ ID NO: 16 is the amino acid sequence of the light chain of IgG1 anti-CD33 antibody 11D5
(Ab_CD33_11D5_mmIgG1_Light Chain; MDT000494), which is specific for CD33$^{\Delta E2}$:
METDTLLLWVLLLWVPGSTGDIVMTQAAFSNPVTLGTSASISCRSNKSLLHSNGITYLYWYLQK
PGQSPQLLIYQMSNLASGVPDRFSSSGSGTDFTLRISRVEAEDVGVYYCAQNLELPPTFGGGT
KLEIKRADAAPTVSIFPPSSEQLTSGGASVVCFLNNFYPKDINVKWKIDGSERQNGVLNSWTDQ
DSKDSTYSMSSTLTLTKDEYERHNSYTCEATHKTSTSPIVKSFNRNEC SEQ ID NO: 17 is the amino acid sequence of the heavy chain of IgG1 anti-CD33 antibody
11D5 (Ab_CD33_11D5_mmIgG1_Heavy Chain; MDT000493), which is specific for CD33$^{\Delta E2}$:
METDTLLLWVLLLWVPGSTGEVQFQQSETVLARPGTSVKLSCKASGYTFTSYWMHWLKQRP
GQGLEWIGAIYCGNSDTSYNQKFKGKAKLTAVTSATTAYMELSSLTNEDSAVYYCKIYDGYHFD
YWGQGTTLTVSSAKTTPPSVYPLAPGSAAQTNSMVTLGCLVKGYFPEPVTVTWNSGSLSSGV
HTFPAVLQSDLYTLSSSVTVPSSPRPSETVTCNVAHPASSTKVDKKIVPRDCGCKPCICTVPEV
SSVFIFPPKPKDVLTITLTPKVTCVVVDISKDDPEVQFSWFVDDVEVHTAQTQPREEQFNSTFR
SVSELPIMHQDWLNGKEFKCRVNSAAFPAPIEKTISKTKGRPKAPQVYTIPPPKEQMAKDKVSL
TCMITDFFPEDITVEWQWNGQPAENYKNTQPIMNTNGSYFVYSKLNVQKSNWEAGNTFTCSV
LHEGLHNHHTEKSLSHSPGK SEQ ID NO: 18 is the amino acid sequence of the light chain of IgG1 anti-CD33 antibody 13E11
(Ab_CD33_13E11_mmIgG1_Light Chain; MDT000499), which is specific for CD33$^{\Delta E2}$:
METDTLLLWVLLLWVPGSTGDIVLTQSPVSLAVSLGQRATISCKASHGVEYAGAHYMNWYQQK
PGQPPKLLIYAASNLGSGTDFTLNIHPVEEEDSATYYCQQSNEDPRTFGGGTKLEIKRADAAPT
VSIFPPSSEQLTSGGASVVCFLNNFYPKDINVKWKIDGSERQNGVLNSWTDQDSKDSTYSMSS
TLTLTKDEYERHNSYTCEATHKTSTSPIVKSFNRNEC

Supporting Sequences

SEQ ID NO: 19 is the amino acid sequence of the heavy chain of IgG1 anti-CD33 antibody
13E11 (Ab_CD33_13E11_mmIgG1_Heavy Chain; MDT000498), which is specific for CD33$^{\Delta E2}$:
METDTLLLWVLLLWVPGSTGKVQLQQSGAELVKPGASVKLSCKASGYTFTDYTLHWLKQRSG
QGLEWIGWFYPTSGSINYNERFKDKATLTADKSSSTVYMELSRLTSVDSAVYFCARHKFGFDY
WGQGTTLTVSSAKTTPPSVYPLAPGSAAQTNSMVTLGCLVKGYFPEPVTVTWNSGSLSSGVH
TFPAVLQSDLYTLSSSVTVPSSPRPSETVTCNVAHPASSTKVDKKIVPRDCGCKPCICTVPEVS
SVFIFPPKPKDVLTITLTPKVTCVVVDISKDDPEVQFSWFVDDVEVHTAQTQPREEQFNSTFRS
VSELPIMHQDWLNGKEFKCRVNSAAFPAPIEKTISKTKGRPKAPQVYTIPPPKEQMAKDKVSLT
CMITDFFPEDITVEWQWNGQPAENYKNTQPIMNTNGSYFVYSKLNVQKSNWEAGNTFTCSVL
HEGLHNHHTEKSLSHSPGK SEQ ID NO: 20 is the amino acid sequence of the light chain of IgG1 anti-CD33 antibody
5E10.7 (Ab_CD33_5E10.7_mmIgG1_Light Chain; MDT000551), which is specific for CD33F1-
and CD33$^{\Delta E2}$:
METDTLLLWVLLLWVPGSTGDIKMTQSPSSIYASLGERVTITCKASQDIKSYLSWYQQKPRKSP
KTLIYYATTLADGVPSRFSGSGSGQDFSLTISSLESDDTATYYCLHHSESPWTFGGGTKLEIKR
ADAAPTVSIFPPSSEQLTSGGASVVCFLNNFYPKDINVKWKIDGSERQNGVLNSWTDQDSKDS
TYSMSSTLTLTKDEYERHNSYTCEATHKTSTSPIVKSFNRNEC SEQ ID NO: 21 is the amino acid sequence of the heavy chain of IgG1 anti-CD33 antibody
5E10.7 (Ab_CD33_5E10.7_mmIgG1_Heavy Chain; MDT000552), which is specific for CD33$^{FL}$
and CD33$^{\Delta E2}$:
METDTLLLWVLLLWVPGSTGQVQLQQPGAEFVKPGASVKLSCKASGYTFTSYWMQWVKQRP
GQGLEWIGEIDSSDSYTNYNQKFKGMATLTVDRSSSTAYMQLSSLTSEDSAVYYCARSRPYD
WFPYWGQGTLVTVSTAKTTPPSVYPLAPGSAAQTNSMVTLGCLVKGYFPEPVTVTWNSGSLS
SGVHTFPAVLQSDLYTLSSSVTVPSSPRPSETVTCNVAHPASSTKVDKKIVPRDCGCKPCICTV
PEVSSVFIFPPKPKDVLTITLTPKVTCVVVDISKDDPEVQFSWFVDDVEVHTAQTQPREEQFNS
TFRSVSELPIMHQDWLNGKEFKCRVNSAAFPAPIEKTISKTKGRPKAPQVYTIPPPKEQMAKDK
VSLTCMITDFFPEDITVEWQWNGQPAENYKNTQPIMNTNGSYFVYSKLNVQKSNWEAGNTFT
CSVLHEGLHNHHTEKSLSHSPGK SEQ ID NO: 22 is the amino acid sequence of the light chain of IgG1 anti-CD33 antibody 11D11
(Ab_CD33_11D11_mmIgG1_Light Chain; MDT000553), which is specific for CD33$^{\Delta E2}$:
METDTLLLWVLLLWVPGSTGDIQMTQTTSSLSASLGDRVTISCRASQDISNYLNWYQQKPDGT
VKLLIYYTSRLHSGVPSRFSGSGSGTDYSLTISNLEQEDIATYFCQQGSTLPPTFGGGTKLEIKR
ADAAPTVSIFPPSSEQLTSGGASVVCFLNNFYPKDINVKWKIDGSERQNGVLNSWTDQDSKDS
TYSMSSTLTLTKDEYERHNSYTCEATHKTSTSPIVKSFNRNEC SEQ ID NO: 23 is the amino acid sequence of the heavy chain of IgG1 anti-CD33 antibody
11D11 (Ab_CD33_11D11_mmIgG1_Heavy Chain; MDT000554), which is specific for CD33$^{\Delta E2}$:
METDTLLLWVLLLWVPGSTGEVNLVESGGGLVQSGRSLRLSCATSGFTFSDFYMEWVRQAPG
KGLEWIAASRNKANDYTTEYKASVKGRFIVSRDTSQSILYLQMNALRAEDTAIYYCTRDTGPMD
YWGQGTSVTVSSAKTTPPSVYPLAPGSAAQTNSMVTLGCLVKGYFPEPVTVTWNSGSLSSGV
HTFPAVLQSDLYTLSSSVTVPSSPRPSETVTCNVAHPASSTKVDKKIVPRDCGCKPCICTVPEV
SSVFIFPPKPKDVLTITLTPKVTCVVVDISKDDPEVQFSWFVDDVEVHTAQTQPREEQFNSTFR
SVSELPIMHQDWLNGKEFKCRVNSAAFPAPIEKTISKTKGRPKAPQVYTIPPPKEQMAKDKVSL
TCMITDFFPEDITVEWQWNGQPAENYKNTQPIMNTNGSYFVYSKLNVQKSNWEAGNTFTCSV
LHEGLHNHHTEKSLSHSPGK SEQ ID NO: 24 is the amino acid sequence of the light chain of IgG1 anti-CD33 antibody 7E7
(Ab_CD33_7E7_mmIgG1_LC), which is specific for CD33$^{\Delta E2}$:
METDTLLLWVLLLWVPGSTGDVVMTQTPLILSVTIGQPASISCKSSQSLLDSDGKTYLSWLLQR
PGQSPKRLIHLVSKLDSGVPDRFTGSGSGTDFTLKISRVEAEDLGVYYCWQGTHFPLTFGAGT
KLELKRADAAPTVSIFPPSSEQLTSGGASVVCFLNNFYPKDINVKWKIDGSERQNGVLNSWTD
QDSKDSTYSMSSTLTLTKDEYERHNSYTCEATHKTSTSPIVKSFNRNEC SEQ ID NO: 25 is the amino acid sequence of the heavy chain of IgG1 anti-CD33 antibody 7E7
(Ab_CD33_7E7_mmIgG1_HC), which is specific for CD33$^{\Delta E2}$:
METDTLLLWVLLLWVPGSTGQVTLKESGPGILQPSQTLSLTCSFSGFSLNSYGMGIGWIRQPS
GKGLEWLAHIVWWDDNKYYKPDLKSRLTVSKDTSKNQVFLKIANVDTTDTATYFCARDGGYSLF
AYWGQGTLVTVSVAKTTPPSVYPLAPGSAAQTNSMVTLGCLVKGYFPEPVTVTWNSGSLSSG
VHTFPAVLQSDLYTLSSSVTVPSSPRPSETVTCNVAHPASSTKVDKKIVPRDCGCKPCICTVPE
VSSVFIFPPKPKDVLTITLTPKVTCVVVDISKDDPEVQFSWFVDDVEVHTAQTQPREEQFNSTF
RSVSELPIMHQDWLNGKEFKCRVNSAAFPAPIEKTISKTKGRPKAPQVYTIPPPKEQMAKDKVS
LTCMITDFFPEDITVEWQWNGQPAENYKNTQPIMNTNGSYFVYSKLNVQKSNWEAGNTFTCS
VLHEGLHNHHTEKSLSHSPGK SEQ ID NO: 26 is the amino acid sequence of human V-set Ig-like domain:
PNFWLQVQESVTVQEGLCVLVPCTFFHPIPYYDKNSPVHGYWFREGAIISRDSPVATNKLDQE
VQEETQGRFRLLGDPSRNNCSLSIVDARRRDNGSYFFRMERG-STKYSYKSPQLS SEQ ID NO: 27 is the amino acid sequence of human C2-set Ig-like domain:
PKILIPGTLEPGHSKNLTCSVSWACEQGTPPIFSWLSAAPTSLGPRTTHSSVLIITPRPQDHGTN
LTCQVKFAGAGVTTERTIQ SEQ ID NOs: 28-31 are amino terminal peptides (neoepitopes) in CD33 confirmed by mass
spectrophotometry (MS):

| Supporting Sequences |
|---|

SEQ ID NO: 28: MPLLLLLPLLWADLTHRPK (E-value: 2E-3)

SEQ ID NO: 29: M$^{oxy}$YPLLLLLPLLWADLTHRPK (E-value: 2E-3)

SEQ ID NO: 30: LLLLLLPLLWADLTHRPK (E-value: 4.9E-4)

SEQ ID NO: 31: PLLLLLLPLLWADLTHRPK (E-value: 1.2E-4)

SEQ ID NO: 32 is the amino acid sequence of human full-length CD33 (CD33$^{FL}$, signal peptide underline):
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGVVHGAIGGAGVTALLALCLCLIFFIVKTHRRKAARTAVGRNDTHPTTGSASPKHQKKSKLHG
PTETSSCSGAAPTVEMDEELHYASLNFHGMNPSKDTSTEYSEVRTQ SEQ ID NO: 33 is the amino acid sequence of the ΔE2 version of human CD33 (CD33$^{ΔE2}$) (signal peptide underlined):
MPLLLLLPLLWADLTHRPKILIPGTLEPGHSKNLTCSVSWACEQGTPPIFSWLSAAPTSLGPRTT
HSSVLIITPRPQDHGTNLTCQVKFAGAGVTTERTIQLNVTYVPQNPTTGIFPGDGSGKQETRAG
VVHGAIGGAGVTALLALCLCLIFFIVKTHRRKAARTAVGRNDTHPTTGSASPKHQKKSKLHGPT
ETSSCSGAAPTVEMDEELHYASLNFHGMNPSKDTSTEYSEVRTQ SEQ ID NO: 34 is the amino acid sequence of CD33$^{E7a}$ which lacks most of the intracellular domain of human CD33 (C-terminal truncation) (signal peptide underlined):
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGVVHGAIGGAGVTALLALCLCLIFFIVKTHRRKAARTAVGRNDTHPTTGSASPVR SEQ ID NO: 35 is the amino acid sequence of cynomolgus CD33 (MfCD33_G7PYH0) shown in the alignment in FIG. 2:
MPLLLLLPLLWAGALAMDPRVRLEVQESVTVQEGLCVLVPCTFFHPVPYHTRNSPVHGYWFRE
GAIVSLDSPVATNKLDQEVQEETQGRFRLLGDPSRNNCSLSIVDARRRDNGSYFFRMEKGSTK
YSYKSTQLSVHVTDLTHRPQILIPGALDPDHSKNLTCSVPWACEQGTPPIFSWMSAAPTSLGLR
TTHSSVLIITPRPQDHGTNLTCQVKFPGAGVTTERTIQLNVSYASQNPRTDIFLGDGSGRKARK
QGVVQGAIGGAGVTVLLALCLCLIFFTVQ SEQ ID NO: 36 is the amino acid sequence of human CD33 (HsCD33_P20138) shown in the alignment in FIG. 2:
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGVVHGAIGGAGVTALLALCLCLIFFIVQ SEQ ID NO: 37 is the amino acid sequence of murine CD33 (MmCD33_Q63994) shown in the alignment in FIG. 2:
MLWPLPLFLLCAGSLAQDLEFQLVAPESVTVEEGLCVHVPCSVFYPSIKLTLGPVTGSWLRKGV
SLHEDSPVATSDPRQLVQKATQGRFQLLGDPQKHDCSLFIRDAQKNDTGMYFFRVVREPFVR
YSYKKSQLSHVTSLSRTPDIIIPGTLEAGYPSNLTCSVPWACEQGTPPTFSWMSTALTSLSSRT
TDSSVLTFTPQPQDHGTKLTCLVTFSGAGVTVERTIQLNVTRKSGQMRELVLVAVG-
EATVKLLILGLCLVFLIVMF From the anti-CD3 antibody OKT3:
CDRL1: SASSSVSYMN (SEQ ID NO: 38)

CDRL2: RWIYDTSKLAS (SEQ ID NO: 39)

CDRL3: QQWSSNPFT (SEQ ID NO: 40)

CDRH1: KASGYTFTRYTMH (SEQ ID NO: 41)

CDRH2: INPSRGYTNYNQKFKD (SEQ ID NO: 42)

CDRH3: YYDDHYCLDY (SEQ ID NO: 43)

SEQ ID NO: 44 is the amino acid sequence of a scFv derived from OKT3 which retains the capacity to bind CD3:
QVQLQQSGAELARPGASVKMSCKASGYTFTRYTMHWVKQRPGQGLEWIGYINPSRGYTNYN
QKFKDKATLTTDKSSSTAYMQLSSLTSEDSAVYYCARYYDDHYCLDYWGQGTTLTVSSGGG
GSGGGGSGGGGSQIVLTQSPAIMSASPGEKVTMTCSASSSVSYMNWYQQKSGTSPKRWIYD
TSKLASGVPAHFRGSGSGTSYSLTISGMEAEDAATYYCQQWSSNPFTFGSGTKLEINR

| Supporting Sequences |
|---|

From the anti-CD3 antibody 20G6-F3
CDRL1: QSLVHNNGNTY (SEQ ID NO: 45)

CDRL2: KVS (SEQ ID NO: 46)

CDRL3: GQGTQYPFT (SEQ ID NO: 47)

CDRH1: GFTFTKAW (SEQ ID NO: 48)

CDRH2: IKDKSNSYAT (SEQ ID NO: 49)

CDRH3: RGVYYALSPFDY (SEQ ID NO: 50)

From the anti-CD3 antibody 4B4-D7
CDRL1: QSLVHDNGNTY (SEQ ID NO: 51)

CDRL2: KVS (SEQ ID NO: 52)

CDRL3: GQGTQYPFT (SEQ ID NO: 53)

CDRH1: GFTFSNAW (SEQ ID NO: 54)

CDRH2: IKARSNNYAT (SEQ ID NO: 55)

CDRH3: RGTYYASKPFDY (SEQ ID NO: 56)

From the anti-CD3 antibody 4E7-C9
CDRL1: QSLEHNNGNTY (SEQ ID NO: 57)

CDRL2: KVS (SEQ ID NO: 58)

CDRL3: GQGTQYPFT (SEQ ID NO: 59)

CDRH1: GFTFSNAW (SEQ ID NO: 60)

CDRH2: IKDKSNNYAT (SEQ ID NO: 61)

CDRH3: RYVHYGIGYAMDA (SEQ ID NO: 62)

From the anti-CD3 18F5-H10 antibody:
CDRL1: QSLVHTNGNTY (SEQ ID NO: 63)

CDRL2: KVS (SEQ ID NO: 64)

CDRL3: GQGTHYPFT (SEQ ID NO: 65)

CDRH1: GFTFTNAW (SEQ ID NO: 66)

CDRH2: KDKSNNYAT (SEQ ID NO: 67)

CDRH3: RYVHYRFAYALDA (SEQ ID NO: 68)

From the anti-CD8 antibody OKT8:
CDRL1: RTSRSISQYLA (SEQ ID NO: 69)

CDRL2: SGSTLQS (SEQ ID NO: 70)

CDRL3: QQHNENPLT (SEQ ID NO: 71)

CDRH1: GFNIKD (SEQ ID NO: 72)

CDRH2: RIDPANDNT (SEQ ID NO: 73)

CDRH3: GYGYYVFDH (SEQ ID NO: 74)

SEQ ID NO: 75 is the amino acid sequence of a variable light chain region of the sequence of a binding domain that binds and blocks the NK cell inhibitory receptors KIR2DL1 and KIR2DL2/3:
EIVLTQSPVTLSLSPGERATLSCRASQSVSSYLAWYQQKPGQAPRLLIYDASNRATGIPARFSG
SGSGTDFTLTISSLEPEDFAVYYCQQRSNWMYTFGQGTKLEIKRT SEQ ID NO: 76 is the amino acid sequence of a variable heavy chain region of the sequence of a binding domain that binds and blocks the NK cell inhibitory receptors KIR2DL1 and KIR2DL2/3:
QVQLVQSGAEVKKPGSSVKVSCKASGGTFSFYAISWVRQAPGQGLEWMGGFIPIFGAANYAQ
KFQGRVTITADESTSTAYMELSSLRSDDTAVYYCARIPSGSYYYDYDMDVWGQGTTVTVSS SEQ ID NOs: 77-82 are linkers:
GGSGGGSGGSG (SEQ ID NO: 77)

| Supporting Sequences |
| --- |

GGSGGGSGSG (SEQ ID NO: 78)

GGSGGGSG (SEQ ID NO: 79)

GGGGSGGGGS (SEQ ID NO: 80)

GGGSGGGS (SEQ ID NO: 81)

GGSGGS (SEQ ID NO: 82).

SEQ ID NO: 83 is the amino acid sequence of the heavy chain of anti-CD33 antibody 1H7
(Ab_CD33_1H7_HC):
METDTLLLWVLLLWVPGSTGQVQLQQSGAELVKPGASVKISCKASGYAFSNYWMNWVKQRP
GKGLEWIGQINPGDGDTNYNGKFKGKATLTADKSSSTAYMQLSSLTSEDSAVYFCAREDRDYF
DYWGQGTTLTVSSAKTTAPSVYPLAPVCGDTTGSSVTLGCLVKGYFPEPVTLTWNSGSLSSG
VHTFPAVLQSDLYTLSSSVTVTSSTWPSQSITCNVAHPASSTKVDKKIEPRGPTIKPCPPCKCPA
PNLLGGPSVFIFPPKIKDVLMISLSPIVTCVVVDVSEDDPDVQISWFVNNVEVHTAQTQTHREDY
NSTLRVVSALPIQHQDWMSGKEFKCKVNNKDLPAPIERTISKPKGSVRAPQVYVLPPPEEEMT
KKQVTLTCMVTDFMPEDIYVEWTNNGKTELNYKNTEPVLDSDGSYFMYSKLRVEKKNWVERN
SYSCSVVHEGLHNHHTTKSFSRTPGK SEQ ID NO: 84 is the amino acid sequence of the light chain of anti-CD33 antibody 1H7
(Ab_CD33_1H7_LC)
METDTLLLWVLLLWVPGSTGDIQMTQTTSSLSASLGDRVTISCRASQDINYYLNWYQQKPDGT
VKLLIYYSSRLHSGVPSRFSGSGSGTDFSLTISNLEQEDIATYFCQQDDALPYTFGGGTKLEIKR
ADAAPTVSIFPPSSEQLTSGGASVVCFLNNFYPKDINVKWKIDGSERQNGVLNSWTDQDSKDS
TYSMSSTLTLTKDEYERHNSYTCEATHKTSTSPIVKSFNRNEC In anti-CD33 antibody 1H7:
CDRL1: RASQDINYYLN (SEQ ID NO: 85)

CDRL2: YSSRLHSG (SEQ ID NO: 86)

CDRL3: QQDDALPYT (SEQ ID NO: 87)

CDRH1: GYAFSNYWMN (SEQ ID NO: 88)

CDRH2: QINPGDGDTNYNG (SEQ ID NO: 89)

CDRH3: EDRDYFDY (SEQ ID NO: 90)

SEQ ID NO: 91 is the amino acid sequence of a 1H7-CD3 BiTE:
METDTLLLWVLLLWVPGSTGDIQMTQTTSSLSASLGDRVTISCRASQDINYYLNWYQQKPDGT
VKLLIYYSSRLHSGVPSRFSGSGSGTDFSLTISNLEQEDIATYFCQQDDALPYTFGGGTKLEIKG
GGGSGGGGSGGGGSQVQLQQSGAELVKPGASVKISCKASGYAFSNYWMNWVKQRPGKGLE
WIGQINPGDGDTNYNGKFKGKATLTADKSSSTAYMQLSSLTSEDSAVYFCAREDRDYFDYWG
QGTTLTVSSGGGGSEVQLVESGGGLVQPGGSLKLSCAASGFTFNKYAMNWVRQAPGKGLEW
VARIRSKYNNYATYYADSVKDRFTISRDDSKNTAYLQMNNLKTEDTAVYYCVRHGNFGNSYISY
WAYWGQGTLVTVSSGGGGSGGGGSGGGGSQTVVTQEPSLTVSPGGTVTLTCGSSTGAVTS
GNYPNWVQQKPGQAPRGLIGGTKFLAPGTPARFSGSLLGGKAALTLSGVQPEDEAEYYCVLW
YSNRWVFGGGTKLTVLHHHHHH SEQ ID NO: 92 is the amino acid sequence of a light chain 1H7-CD3 engager:
METDTLLLWVLLLWVPGSTGDIQMTQTTSSLSASLGDRVTISCRASQDINYYLNWYQQKPDGT
VKLLIYYSSRLHSGVPSRFSGSGSGTDFSLTISNLEQEDIATYFCQQDDALPYTFGGGTKLEIKR
ADAAPTVSIFPPSSEQLTSGGASVVCFLNNFYPKDINVKWKIDGSERQNGVLNSWTDQDSKDS
TYSMSSTLTLTKDEYERHNSYTCEATHKTSTSPIVKSFNRNECGGGGSGGGGSGGGGSEVQL
VESGGGLVQPGGSLKLSCAASGFTFNKYAMNWVRQAPGKGLEWVARIRSKYNNYATYYADS
VKDRFTISRDDSKNTAYLQMNNLKTEDTAVYYCVRHGNFGNSYISYWAYWGQGTLVTVSSGG
GGSGGGGSGGGGSQTVVTQEPSLTVSPGGTVTLTCGSSTGAVTSGNYPNWVQQKPGQAPR
GLIGGTKFLAPGTPARFSGSLLGGKAALTLSGVQPEDEAEYYCVLWYSNRWVFGGGTKLTVLH
HHHHH SEQ ID NO: 93 is the amino acid sequence of a heavy chain 1H7-CD3 engager:
METDTLLLWVLLLWVPGSTGQVQLQQSGAELVKPGASVKISCKASGYAFSNYWMNWVKQRP
GKGLEWIGQINPGDGDTNYNGKFKGKATLTADKSSSTAYMQLSSLTSEDSAVYFCAREDRDYF
DYWGQGTTLTVSSAKTTAPSVYPLAPVCGDTTGSSVTLGCLVKGYFPEPVTLTWNSGSLSSG
VHTFPAVLQSDLYTLSSSVTVTSSTWPSQSITCNVAHPASSTKVDKKIEPRGPTIKPCPPCKCPA
PNLLGGPSVFIFPPKIKDVLMISLSPIVTCVVVDVSEDDPDVQISWFVNNVEVHTAQTQTHREDY
NSTLRVVSALPIQHQDWMSGKEFKCKVNNKDLPAPIERTISKPKGSVRAPQVYVLPPPEEEMT
KKQVTLTCMVTDFMPEDIYVEWTNNGKTELNYKNTEPVLDSDGSYFMYSKLRVEKKNWVERN
SYSCSVVHEGLHNHHTTKSFSRTPGK -continued

| | Supporting Sequences | |
|---|---|---|
| | SEQ ID NOs: 94-153 are CDR sequences from anti-CD33 antibodies, as follows: | |
| SEQ ID NO: | Sequence | Antibody and CDR |
| 94 | GYAFSNYWMN | 5D12_CDRH1 |
| 95 | QIYPGNFNTDYNGQFKG | 5D12_CDRH2 |
| 96 | FFDFGAYFTLDY | 5D12_CDRH3 |
| 97 | KASQDIKSYLS | 5D12_CDRL1 |
| 98 | YATTLAD | 5D12_CDRL2 |
| 99 | LHHGESPWT | 5D12_CDRL3 |
| 100 | SGFTFSDFYMY | 8F5_CDRH1 |
| 101 | FISNAGVTTYYPDTVEG | 8F5_CDRH2 |
| 102 | SDYDGAWFPY | 8F5_CDRH3 |
| 103 | KSSQSLLYSRNQYNFLA | 8F5_CDRL1 |
| 104 | WASTRES | 8F5_CDRL2 |
| 105 | QQYYSYPYT | 8F5_CDRL3 |
| 106 | GYTFTTYWMH | 12B12_CDRH1 |
| 107 | AIYPGNSDTSYNQ | 12B12_CDRH2 |
| 108 | YDGYHFI | 12B12_CDRH3 |
| 109 | RSSQSLLHSNGITYLY | 12B12_CDRL1 |
| 110 | QMSNLAS | 12B12_CDRL2 |
| 111 | AQNLELPPT | 12B12_CDRL3 |
| 112 | GYAFTNYLIE | 4H10_CDRH1 |
| 113 | VIHPGNNSTSYNA | 4H10_CDRH2 |
| 114 | YGYDERNAMDY | 4H10_CDRH3 |
| 115 | QSLLYSNGKTYLH | 4H10_CDRL1 |
| 116 | VPDRFTGSGSGTDFTL | 4H10_CDRL2 |
| 117 | GTHFPRTFG | 4H10_CDRL3 |
| 118 | GYTFTSYWMH | 11D5_CDRH1 |
| 119 | AIYCGNSDTSYNQ | 11D5_CDRH2 |
| 120 | YDGYHFDY | 11D5_CDRH3 |
| 121 | RSNKSLLHSNGITYLY | 11D5_CDRL1 |
| 122 | QMSNLAS | 11D5_CDRL2 |
| 123 | AQNLELPPT | 11D5_CDRL3 |
| 124 | GYTFTDYTLH | 13E11_CDRH1 |
| 125 | WFYPTSGSINYNE | 13E11_CDRH2 |
| 126 | HKFGFDY | 13E11_CDRH3 |
| 127 | KASHGVEYAGAHYMN | 13E11_CDRL1 |
| 128 | AASNLGS | 13E11_CDRL2 |
| 129 | QQSNEDPRT | 13E11_CDRL3 |
| 136 | SGFTFSDFYME | 11D11_CDRH1 |

| | | |
|---|---|---|
| Supporting Sequences | | |
| 137 | ASRNKANDYTTEY | 11D11_CDRH2 |
| 138 | DTGPMDY | 11D11_CDRH3 |
| 139 | RASQDISNYLN | 11D11_CDRL1 |
| 140 | YTSRLHS | 11D11_CDRL2 |
| 141 | QQGSTLPPT | 11D11_CDRL3 |
| 142 | GFSLNSYGMGIG | 7E7_CDRH1 |
| 143 | HIWWDDNKYYKPDLKS | 7E7_CDRH2 |
| 144 | DGGYSLFAY | 7E7_CDRH3 |
| 145 | KSSQSLLDSDGKTYLS | 7E7_CDRL1 |
| 146 | VSKLDSG | 7E7_CDRL2 |
| 147 | WQGTHFPLT | 7E7_CDRL3 |
| 130 | GYTFTSYWMQ | 5E10.7_CDRH1 |
| 131 | EIDSSDSYTNYNQ | 5E10.7_CDRH2 |
| 132 | SRPYDWFPY | 5E10.7_CDRH3 |
| 133 | KASQDIKSYLS | 5E10.7_CDRL1 |
| 134 | YATTLAD | 5E10.7_CDRL2 |
| 135 | LHHSESPWT | 5E10.7_CDRL3 |
| 148 | GYTFTDYDMH | 2D5_CDRH1 |
| 149 | AIDPETGGTAYNQNF | 2D5_CDRH2 |
| 150 | DYDYFGV | 2D5_CDRH3 |
| 151 | KASQNVGTNVV | 2D5_CDRL1 |
| 152 | SASDRYS | 2D5_CDRL2 |
| 153 | QQYNIYPYT | 2D5_CDRL3 |

SEQ ID NO: 154 is the amino acid sequence of the light chain of anti-CD33 antibody 2D5:
MESQTQVFVYMLLWLSGVDGDIVMTQSQKFMSTSVGDRVSVTCKASQNVGTNVVWYHKKPG
QSPKGLIYSASDRYSGVPDRFTGSGSGTDFTLTINNVQSEDLAEYFCQQYNIYPYTFGGGTKLE
IKR SEQ ID NO: 155 is the amino acid sequence of the heavy chain of anti-CD33 antibody 2D5:
MEWSWVCLFLLSVIAGVQSQVQLQQSGAELVRPGASVTLSCKASGYTFTDYDMHWVKQTPV
HGLEWIGAIDPETGGTAYNQNFKGKAILTVDKSSRIAYMELRSLTSEDSAVFYCTSDYDYFGVW
GTGTTVTVSS SEQ ID NO: 156 is the amino acid sequence of CD33$^{FL}$ signal peptide fused to the C-terminal end of CD33$^{\Delta E2}$, from FIG. 14A:
MPLLLLLPLLWAGALAMDLTHRPKILIPGTLEPGHSKNLTCSVS SEQ ID NO: 157 is the amino acid sequence of CD33$^{\Delta E2}$ signal peptide fused to the C-terminal end of CD33$^{FL}$, from FIG. 14A:
MPLLLLLPLLWADLTHRPKILIPNFWLQVQESVTVQEGLCVLVPCTFF

SEQUENCE LISTING

<160> NUMBER OF SEQ ID NOS: 159

<210> SEQ ID NO 1
<211> LENGTH: 481
<212> TYPE: PRT
<213> ORGANISM: Artificial Sequence -continued

```
<220> FEATURE:
<223> OTHER INFORMATION: amino acid sequence of human full-length CD33
      (MDT000208; hsCD33-mmFc; Immunogen for human full-length)

<400> SEQUENCE: 1

Met Pro Leu Leu Leu Leu Pro Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
                100                 105                 110

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
            210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Gly Gly Ser Gly Cys Lys Pro Cys Ile Cys Thr Val Pro Glu Val Ser
            260                 265                 270

Ser Val Phe Ile Phe Pro Pro Lys Pro Lys Asp Val Leu Thr Ile Thr
        275                 280                 285

Leu Thr Pro Lys Val Thr Cys Val Val Asp Ile Ser Lys Asp Asp
    290                 295                 300

Pro Glu Val Gln Phe Ser Trp Phe Val Asp Asp Val Glu Val His Thr
305                 310                 315                 320

Ala Gln Thr Gln Pro Arg Glu Glu Gln Phe Asn Ser Thr Phe Arg Ser
                325                 330                 335

Val Ser Glu Leu Pro Ile Met His Gln Asp Trp Leu Asn Gly Lys Glu
            340                 345                 350

Phe Lys Cys Arg Val Asn Ser Ala Ala Phe Pro Ala Pro Ile Glu Lys
        355                 360                 365

Thr Ile Ser Lys Thr Lys Gly Arg Pro Lys Ala Pro Gln Val Tyr Thr
    370                 375                 380

Ile Pro Pro Pro Lys Glu Gln Met Ala Lys Asp Lys Val Ser Leu Thr
```

```
385                 390                 395                 400
Cys Met Ile Thr Asp Phe Phe Pro Glu Asp Ile Thr Val Glu Trp Gln
                405                 410                 415

Trp Asn Gly Gln Pro Ala Glu Asn Tyr Lys Asn Thr Gln Pro Ile Met
                420                 425                 430

Asn Thr Asn Gly Ser Tyr Phe Val Tyr Ser Lys Leu Asn Val Gln Lys
                435                 440                 445

Ser Asn Trp Glu Ala Gly Asn Thr Phe Thr Cys Ser Val Leu His Glu
                450                 455                 460

Gly Leu His Asn His His Thr Glu Lys Ser Leu Ser His Ser Pro Gly
465                 470                 475                 480

Lys

<210> SEQ ID NO 2
<211> LENGTH: 244
<212> TYPE: PRT
<213> ORGANISM: Artificial Sequence
<220> FEATURE:
<223> OTHER INFORMATION: amino acid sequence of human DeltaE2 version of
      CD33 with a mouse Fc domain

<400> SEQUENCE: 2

Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
                20                  25                  30

Asn Leu Thr Cys Ser Val Ser Trp Ala Cys Glu Gln Gly Thr Pro Pro
                35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
                100                 105                 110

Thr Gly Ile Phe Pro Gly Asp Gly Ser Gly Lys Gln Glu Thr Arg Ala
            115                 120                 125

Gly Gly Gly Ser Gly Cys Lys Pro Cys Ile Cys Thr Val Pro Glu Val
130                 135                 140

Ser Ser Val Phe Ile Phe Pro Pro Lys Pro Lys Asp Val Leu Thr Ile
145                 150                 155                 160

Thr Leu Thr Pro Lys Val Thr Cys Val Val Asp Ile Ser Lys Asp
                165                 170                 175

Asp Pro Glu Val Gln Phe Ser Trp Phe Val Asp Asp Val Glu Val His
                180                 185                 190

Thr Ala Gln Thr Gln Pro Arg Glu Glu Gln Phe Asn Ser Thr Phe Arg
                195                 200                 205

Ser Val Ser Glu Leu Pro Ile Met His Gln Asp Trp Leu Asn Gly Lys
            210                 215                 220

Glu Phe Lys Cys Arg Val Asn Ser Ala Ala Phe Pro Ala Pro Ile Glu
225                 230                 235                 240

Lys Thr Ile Ser

<210> SEQ ID NO 3
```

```
<211> LENGTH: 480
<212> TYPE: PRT
<213> ORGANISM: Artificial Sequence
<220> FEATURE:
<223> OTHER INFORMATION: amino acid sequence of Macaca fascicularis CD33
      full-length with a mouse Fc domain

<400> SEQUENCE: 3
```

| | | | | | | | | | | | | | | |
|---|---|---|---|---|---|---|---|---|---|---|---|---|---|---|
| Met | Pro | Leu | Leu | Leu | Pro | Leu | Leu | Trp | Ala | Gly | Ala | Leu | Ala | Met |
| 1 | | | | 5 | | | | | 10 | | | | | 15 |
| Asp | Pro | Arg | Val | Arg | Leu | Glu | Val | Gln | Glu | Ser | Val | Thr | Val | Gln | Glu |
| | | | 20 | | | | | 25 | | | | | 30 | | |
| Gly | Leu | Cys | Val | Leu | Val | Pro | Cys | Thr | Phe | Phe | His | Pro | Val | Pro | Tyr |
| | | 35 | | | | | 40 | | | | | 45 | | | |
| His | Thr | Arg | Asn | Ser | Pro | Val | His | Gly | Tyr | Trp | Phe | Arg | Glu | Gly | Ala |
| | 50 | | | | | 55 | | | | | 60 | | | | |
| Ile | Val | Ser | Leu | Asp | Ser | Pro | Val | Ala | Thr | Asn | Lys | Leu | Asp | Gln | Glu |
| 65 | | | | | 70 | | | | | 75 | | | | | 80 |
| Val | Gln | Glu | Glu | Thr | Gln | Gly | Arg | Phe | Arg | Leu | Leu | Gly | Asp | Pro | Ser |
| | | | | 85 | | | | | 90 | | | | | 95 | |
| Arg | Asn | Asn | Cys | Ser | Leu | Ser | Ile | Val | Asp | Ala | Arg | Arg | Arg | Asp | Asn |
| | | | 100 | | | | | 105 | | | | | 110 | | |
| Gly | Ser | Tyr | Phe | Phe | Arg | Met | Glu | Lys | Gly | Ser | Thr | Lys | Tyr | Ser | Tyr |
| | | 115 | | | | | 120 | | | | | 125 | | | |
| Lys | Ser | Thr | Gln | Leu | Ser | Val | His | Val | Thr | Asp | Leu | Thr | His | Arg | Pro |
| 130 | | | | | 135 | | | | | 140 | | | | | |
| Gln | Ile | Leu | Ile | Pro | Gly | Ala | Leu | Asp | Pro | Asp | His | Ser | Lys | Asn | Leu |
| 145 | | | | | 150 | | | | | 155 | | | | | 160 |
| Thr | Cys | Ser | Val | Pro | Trp | Ala | Cys | Glu | Gln | Gly | Thr | Pro | Pro | Ile | Phe |
| | | | | 165 | | | | | 170 | | | | | 175 | |
| Ser | Trp | Met | Ser | Ala | Ala | Pro | Thr | Ser | Leu | Gly | Leu | Arg | Thr | Thr | His |
| | | | 180 | | | | | 185 | | | | | 190 | | |
| Ser | Ser | Val | Leu | Ile | Ile | Thr | Pro | Arg | Pro | Gln | Asp | His | Gly | Thr | Asn |
| | | 195 | | | | | 200 | | | | | 205 | | | |
| Leu | Thr | Cys | Gln | Val | Lys | Phe | Pro | Gly | Ala | Gly | Val | Thr | Thr | Glu | Arg |
| | 210 | | | | | 215 | | | | | 220 | | | | |
| Thr | Ile | Gln | Leu | Asn | Val | Ser | Tyr | Ala | Ser | Gln | Asn | Pro | Arg | Thr | Asp |
| 225 | | | | | 230 | | | | | 235 | | | | | 240 |
| Ile | Phe | Leu | Gly | Asp | Gly | Ser | Gly | Arg | Lys | Ala | Arg | Lys | Gln | Gly | Gly |
| | | | | 245 | | | | | 250 | | | | | 255 | |
| Gly | Ser | Gly | Cys | Lys | Pro | Cys | Ile | Cys | Thr | Val | Pro | Glu | Val | Ser | Ser |
| | | | 260 | | | | | 265 | | | | | 270 | | |
| Val | Phe | Ile | Phe | Pro | Pro | Lys | Pro | Lys | Asp | Val | Leu | Thr | Ile | Thr | Leu |
| | | 275 | | | | | 280 | | | | | 285 | | | |
| Thr | Pro | Lys | Val | Thr | Cys | Val | Val | Asp | Ile | Ser | Lys | Asp | Asp | Pro |
| | 290 | | | | | 295 | | | | | 300 | | | | |
| Glu | Val | Gln | Phe | Ser | Trp | Phe | Val | Asp | Asp | Val | Glu | Val | His | Thr | Ala |
| 305 | | | | | 310 | | | | | 315 | | | | | 320 |
| Gln | Thr | Gln | Pro | Arg | Glu | Glu | Gln | Phe | Asn | Ser | Thr | Phe | Arg | Ser | Val |
| | | | | 325 | | | | | 330 | | | | | 335 | |
| Ser | Glu | Leu | Pro | Ile | Met | His | Gln | Asp | Trp | Leu | Asn | Gly | Lys | Glu | Phe |
| | | | 340 | | | | | 345 | | | | | 350 | | |
| Lys | Cys | Arg | Val | Asn | Ser | Ala | Ala | Phe | Pro | Ala | Pro | Ile | Glu | Lys | Thr |
| | | 355 | | | | | 360 | | | | | 365 | | | |
| Ile | Ser | Lys | Thr | Lys | Gly | Arg | Pro | Lys | Ala | Pro | Gln | Val | Tyr | Thr | Ile |

```
                    370                 375                 380
Pro Pro Pro Lys Glu Gln Met Ala Lys Asp Lys Val Ser Leu Thr Cys
385                 390                 395                 400

Met Ile Thr Asp Phe Phe Pro Glu Asp Ile Thr Val Glu Trp Gln Trp
                    405                 410                 415

Asn Gly Gln Pro Ala Glu Asn Tyr Lys Asn Thr Gln Pro Ile Met Asn
                420                 425                 430

Thr Asn Gly Ser Tyr Phe Val Tyr Ser Lys Leu Asn Val Gln Lys Ser
            435                 440                 445

Asn Trp Glu Ala Gly Asn Thr Phe Thr Cys Ser Val Leu His Glu Gly
        450                 455                 460

Leu His Asn His His Thr Glu Lys Ser Leu Ser His Ser Pro Gly Lys
465                 470                 475                 480
```

<210> SEQ ID NO 4
<211> LENGTH: 489
<212> TYPE: PRT
<213> ORGANISM: Artificial Sequence
<220> FEATURE:
<223> OTHER INFORMATION: amino acid sequence of the extracellular domain of mouse CD33 full length where the C2-set Ig-like domain from mouse has been replaced with the C2-set Ig-like domain from human CD33, combined with a with a Fc region from human IgG1

<400> SEQUENCE: 4

```
Met Leu Trp Pro Leu Pro Leu Phe Leu Leu Cys Ala Gly Ser Leu Ala
1               5                   10                  15

Gln Asp Leu Glu Phe Gln Leu Val Ala Pro Glu Ser Val Thr Val Glu
                20                  25                  30

Glu Gly Leu Cys Val His Val Pro Cys Ser Val Phe Tyr Pro Ser Ile
            35                  40                  45

Lys Leu Thr Leu Gly Pro Val Thr Gly Ser Trp Leu Arg Lys Gly Val
        50                  55                  60

Ser Leu His Glu Asp Ser Pro Val Ala Thr Ser Asp Pro Arg Gln Leu
65                  70                  75                  80

Val Gln Lys Ala Thr Gln Gly Arg Phe Gln Leu Leu Gly Asp Pro Gln
                85                  90                  95

Lys His Asp Cys Ser Leu Phe Ile Arg Asp Ala Gln Lys Asn Asp Thr
                100                 105                 110

Gly Met Tyr Phe Phe Arg Val Val Arg Glu Pro Phe Val Arg Tyr Ser
            115                 120                 125

Tyr Lys Lys Ser Gln Leu Ser Leu His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
                180                 185                 190

His Ser Ser Val Leu Ile Ile Thr Pro Arg Pro Gln Asp His Gly Thr
            195                 200                 205

Asn Leu Thr Cys Gln Val Lys Phe Ala Gly Ala Gly Val Thr Thr Glu
        210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
```

```
                        245                 250                 255
Ser Glu Pro Lys Ser Asp Lys Thr His Thr Cys Pro Cys Pro
            260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
        290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
        370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
        450                 455                 460

Phe Ser Cys Ser Val Met His Glu Ala Leu His Asn His Tyr Thr Gln
465                 470                 475                 480

Lys Ser Leu Ser Leu Ser Pro Gly Lys
            485

<210> SEQ ID NO 5
<211> LENGTH: 280
<212> TYPE: PRT
<213> ORGANISM: Artificial Sequence
<220> FEATURE:
<223> OTHER INFORMATION: amino acid sequence of the extracellular domain
      of CD33 full-length with a 6-histidine-avidin tag

<400> SEQUENCE: 5

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110
```

```
Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Ser His His His His His Gly Ser Gly Leu Asn Asp Ile Phe Glu
            260                 265                 270

Ala Gln Lys Ile Glu Trp His Glu
        275                 280

<210> SEQ ID NO 6
<211> LENGTH: 279
<212> TYPE: PRT
<213> ORGANISM: Artificial Sequence
<220> FEATURE:
<223> OTHER INFORMATION: amino acid sequence of the extracellular domain
      of Macaque fascicularis CD33 full-length with a 6-histidine-avidin
      tag

<400> SEQUENCE: 6

Met Pro Leu Leu Leu Leu Pro Leu Leu Trp Ala Gly Ala Leu Ala Met
1               5                   10                  15

Asp Pro Arg Val Arg Leu Glu Val Gln Glu Ser Val Thr Val Gln Glu
            20                  25                  30

Gly Leu Cys Val Leu Val Pro Cys Thr Phe His Pro Val Pro Tyr
        35                  40                  45

His Thr Arg Asn Ser Pro Val His Gly Tyr Trp Phe Arg Glu Gly Ala
    50                  55                  60

Ile Val Ser Leu Asp Ser Pro Val Ala Thr Asn Lys Leu Asp Gln Glu
65                  70                  75                  80

Val Gln Glu Glu Thr Gln Gly Arg Phe Arg Leu Leu Gly Asp Pro Ser
                85                  90                  95

Arg Asn Asn Cys Ser Leu Ser Ile Val Asp Ala Arg Arg Asp Asn
            100                 105                 110

Gly Ser Tyr Phe Phe Arg Met Glu Lys Gly Ser Thr Lys Tyr Ser Tyr
        115                 120                 125

Lys Ser Thr Gln Leu Ser Val His Val Thr Asp Leu Thr His Arg Pro
    130                 135                 140

Gln Ile Leu Ile Pro Gly Ala Leu Asp Pro Asp His Ser Lys Asn Leu
145                 150                 155                 160

Thr Cys Ser Val Pro Trp Ala Cys Glu Gln Gly Thr Pro Pro Ile Phe
                165                 170                 175

Ser Trp Met Ser Ala Ala Pro Thr Ser Leu Gly Leu Arg Thr Thr His
```

```
            180                 185                 190
Ser Ser Val Leu Ile Ile Thr Pro Arg Pro Gln Asp His Gly Thr Asn
                195                 200                 205

Leu Thr Cys Gln Val Lys Phe Pro Gly Ala Gly Val Thr Thr Glu Arg
    210                 215                 220

Thr Ile Gln Leu Asn Val Ser Tyr Ala Ser Gln Asn Pro Arg Thr Asp
225                 230                 235                 240

Ile Phe Leu Gly Asp Gly Ser Gly Arg Lys Ala Arg Lys Gln Gly Ser
                245                 250                 255

His His His His His His Gly Ser Gly Leu Asn Asp Ile Phe Glu Ala
                260                 265                 270

Gln Lys Ile Glu Trp His Glu
        275
```

<210> SEQ ID NO 7
<211> LENGTH: 153
<212> TYPE: PRT
<213> ORGANISM: Artificial Sequence
<220> FEATURE:
<223> OTHER INFORMATION: amino acid sequence of the extracellular domain
      of CD33DeltaE2 with a 6-histidine-avidin tag

<400> SEQUENCE: 7

```
Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
                20                  25                  30

Asn Leu Thr Cys Ser Val Ser Trp Ala Ser Glu Gln Gly Thr Pro Pro
            35                  40                  45

Ile Phe Ser Trp Leu Ser Ala Ala Pro Thr Ser Leu Gly Pro Arg Thr
        50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
                100                 105                 110

Thr Gly Ile Phe Pro Gly Asp Gly Ser Gly Lys Gln Glu Thr Arg Ala
            115                 120                 125

Gly Ser His His His His His His Gly Ser Gly Leu Asn Asp Ile Phe
        130                 135                 140

Glu Ala Gln Lys Ile Glu Trp His Glu
145                 150
```

<210> SEQ ID NO 8
<211> LENGTH: 234
<212> TYPE: PRT
<213> ORGANISM: Artificial Sequence
<220> FEATURE:
<223> OTHER INFORMATION: amino acid sequence of the light chain of IgG2a
      anti-CD33 antibody 5D12

<400> SEQUENCE: 8

```
Met Glu Thr Asp Thr Leu Leu Leu Trp Val Leu Leu Leu Trp Val Pro
1               5                   10                  15

Gly Ser Thr Gly Asp Ile Lys Met Thr Gln Ser Pro Ser Ser Ile Tyr
                20                  25                  30

Ala Ser Leu Gly Glu Arg Val Thr Ile Asn Cys Lys Ala Ser Gln Asp
```

```
            35                  40                  45
Ile Lys Ser Tyr Leu Ser Trp Tyr Gln Gln Lys Pro Trp Lys Ser Pro
 50                  55                  60

Lys Thr Leu Ile Tyr Tyr Ala Thr Thr Leu Ala Asp Gly Val Pro Ser
 65                  70                  75                  80

Arg Phe Ser Gly Ser Gly Ser Gly Gln Asp Tyr Ser Leu Thr Ile Ser
                     85                  90                  95

Ser Leu Glu Ser Asp Asp Thr Ala Thr Tyr Tyr Cys Leu His His Gly
                100                 105                 110

Glu Ser Pro Trp Thr Phe Gly Glu Gly Thr Lys Leu Glu Ile Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230

<210> SEQ ID NO 9
<211> LENGTH: 471
<212> TYPE: PRT
<213> ORGANISM: Artificial Sequence
<220> FEATURE:
<223> OTHER INFORMATION: amino acid sequence of the heavy chain of IgG2a
      anti-CD33 antibody 5D12

<400> SEQUENCE: 9

Met Glu Thr Asp Thr Leu Leu Leu Trp Val Leu Leu Leu Trp Val Pro
 1               5                  10                  15

Gly Ser Thr Gly Gln Val Gln Leu Gln Gln Ser Gly Ala Glu Val Val
                 20                  25                  30

Lys Pro Gly Ala Ser Val Lys Ile Ser Cys Arg Ala Ser Gly Tyr Ala
             35                  40                  45

Phe Ser Asn Tyr Trp Met Asn Trp Val Lys Gln Arg Pro Gly Lys Gly
 50                  55                  60

Leu Glu Trp Ile Gly Gln Ile Tyr Pro Gly Asn Phe Asn Thr Asp Tyr
 65                  70                  75                  80

Asn Gly Gln Phe Lys Gly Lys Ala Thr Leu Thr Val Asp Lys Ser Ser
                 85                  90                  95

Asn Thr Ala Tyr Met Gln Leu Ser Ser Leu Thr Ser Glu Asp Ser Ala
                100                 105                 110

Val Tyr Phe Cys Ala Arg Phe Phe Asp Phe Gly Ala Tyr Phe Thr Leu
            115                 120                 125

Asp Tyr Trp Gly Gln Gly Thr Ser Val Thr Val Ser Ser Ala Lys Thr
130                 135                 140

Thr Ala Pro Ser Val Tyr Pro Leu Ala Pro Val Cys Gly Asp Thr Thr
145                 150                 155                 160
```

```
Gly Ser Ser Val Thr Leu Gly Cys Leu Val Lys Gly Tyr Phe Pro Glu
                165                 170                 175

Pro Val Thr Leu Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Thr Ser Ser Thr Trp Pro Ser Gln Ser Ile Thr Cys Asn
210                 215                 220

Val Ala His Pro Ala Ser Ser Thr Lys Val Asp Lys Lys Ile Glu Pro
225                 230                 235                 240

Arg Gly Pro Thr Ile Lys Pro Cys Pro Pro Cys Lys Cys Pro Ala Pro
                245                 250                 255

Asn Leu Leu Gly Gly Pro Ser Val Phe Ile Phe Pro Pro Lys Ile Lys
            260                 265                 270

Asp Val Leu Met Ile Ser Leu Ser Pro Ile Val Thr Cys Val Val Val
        275                 280                 285

Asp Val Ser Glu Asp Asp Pro Asp Val Gln Ile Ser Trp Phe Val Asn
    290                 295                 300

Asn Val Glu Val His Thr Ala Gln Thr Gln Thr His Arg Glu Asp Tyr
305                 310                 315                 320

Asn Ser Thr Leu Arg Val Val Ser Ala Leu Pro Ile Gln His Gln Asp
                325                 330                 335

Trp Met Ser Gly Lys Glu Phe Lys Cys Lys Val Asn Asn Lys Asp Leu
            340                 345                 350

Pro Ala Pro Ile Glu Arg Thr Ile Ser Lys Pro Lys Gly Ser Val Arg
        355                 360                 365

Ala Pro Gln Val Tyr Val Leu Pro Pro Pro Glu Glu Glu Met Thr Lys
370                 375                 380

Lys Gln Val Thr Leu Thr Cys Met Val Thr Asp Phe Met Pro Glu Asp
385                 390                 395                 400

Ile Tyr Val Glu Trp Thr Asn Asn Gly Lys Thr Glu Leu Asn Tyr Lys
                405                 410                 415

Asn Thr Glu Pro Val Leu Asp Ser Asp Gly Ser Tyr Phe Met Tyr Ser
            420                 425                 430

Lys Leu Arg Val Glu Lys Lys Asn Trp Val Glu Arg Asn Ser Tyr Ser
        435                 440                 445

Cys Ser Val Val His Glu Gly Leu His Asn His His Thr Thr Lys Ser
450                 455                 460

Phe Ser Arg Thr Pro Gly Lys
465                 470

<210> SEQ ID NO 10
<211> LENGTH: 240
<212> TYPE: PRT
<213> ORGANISM: Artificial Sequence
<220> FEATURE:
<223> OTHER INFORMATION: amino acid sequence of the light chain of IgG2a
      anti-CD33 antibody 8F5

<400> SEQUENCE: 10

Met Glu Thr Asp Thr Leu Leu Leu Trp Val Leu Leu Leu Trp Val Pro
1               5                   10                  15

Gly Ser Thr Gly Asp Ile Val Met Ser Gln Ser Pro Ser Ser Leu Pro
            20                  25                  30

Val Ser Val Gly Glu Lys Val Thr Leu Ser Cys Lys Ser Ser Gln Ser
        35                  40                  45
```

Leu Leu Tyr Ser Arg Asn Gln Tyr Asn Phe Leu Ala Trp Tyr Gln Gln
            50                  55                  60

Arg Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
                100                 105                 110

Tyr Cys Gln Gln Tyr Tyr Ser Tyr Pro Tyr Thr Phe Gly Gly Gly Thr
            115                 120                 125

Lys Leu Glu Ile Lys Arg Ala Asp Ala Ala Pro Thr Val Ser Ile Phe
130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
                180                 185                 190

Asp Ser Lys Asp Ser Thr Tyr Ser Met Ser Ser Thr Leu Thr Leu Thr
            195                 200                 205

Lys Asp Glu Tyr Glu Arg His Asn Ser Tyr Thr Cys Glu Ala Thr His
210                 215                 220

Lys Thr Ser Thr Ser Pro Ile Val Lys Ser Phe Asn Arg Asn Glu Cys
225                 230                 235                 240

<210> SEQ ID NO 11
<211> LENGTH: 469
<212> TYPE: PRT
<213> ORGANISM: Artificial Sequence
<220> FEATURE:
<223> OTHER INFORMATION: amino acid sequence of the heavy chain of IgG2a
      anti-CD33 antibody 8F5

<400> SEQUENCE: 11

Met Glu Thr Asp Thr Leu Leu Leu Trp Val Leu Leu Leu Trp Val Pro
 1               5                   10                  15

Gly Ser Thr Gly Glu Val Lys Leu Val Glu Ser Gly Gly Gly Leu Val
                20                  25                  30

Gln Pro Gly Gly Ser Leu Lys Leu Ser Cys Ala Ala Ser Gly Phe Thr
            35                  40                  45

Phe Ser Asp Phe Tyr Met Tyr Trp Val Arg Gln Thr Pro Glu Lys Arg
 50                  55                  60

Leu Glu Trp Val Ala Phe Ile Ser Asn Ala Gly Val Thr Thr Tyr Tyr
 65                  70                  75                  80

Pro Asp Thr Val Glu Gly Arg Phe Thr Ile Ser Arg Asp Asn Ala Lys
                85                  90                  95

Asn Thr Leu Tyr Leu Gln Met Ser Arg Leu Met Ser Glu Asp Thr Ala
                100                 105                 110

Met Tyr Tyr Cys Thr Lys Ser Asp Tyr Asp Gly Ala Trp Phe Pro Tyr
            115                 120                 125

Trp Gly Gln Gly Thr Leu Val Thr Val Ser Ala Ala Lys Thr Thr Ala
130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val

```
                165                 170                 175
Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
            245                 250                 255

Leu Gly Gly Pro Ser Val Phe Ile Phe Pro Pro Lys Ile Lys Asp Val
        260                 265                 270

Leu Met Ile Ser Leu Ser Pro Ile Val Thr Cys Val Val Val Asp Val
    275                 280                 285

Ser Glu Asp Asp Pro Asp Val Gln Ile Ser Trp Phe Val Asn Asn Val
290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
            325                 330                 335

Ser Gly Lys Glu Phe Lys Cys Lys Val Asn Asn Lys Asp Leu Pro Ala
        340                 345                 350

Pro Ile Glu Arg Thr Ile Ser Lys Pro Lys Gly Ser Val Arg Ala Pro
    355                 360                 365

Gln Val Tyr Val Leu Pro Pro Pro Glu Glu Glu Met Thr Lys Lys Gln
370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
            405                 410                 415

Glu Pro Val Leu Asp Ser Asp Gly Ser Tyr Phe Met Tyr Ser Lys Leu
        420                 425                 430

Arg Val Glu Lys Lys Asn Trp Val Glu Arg Asn Ser Tyr Ser Cys Ser
    435                 440                 445

Val Val His Glu Gly Leu His Asn His His Thr Thr Lys Ser Phe Ser
    450                 455                 460

Arg Thr Pro Gly Lys
465

<210> SEQ ID NO 12
<211> LENGTH: 239
<212> TYPE: PRT
<213> ORGANISM: Artificial Sequence
<220> FEATURE:
<223> OTHER INFORMATION: amino acid sequence of the light chain of IgG2b
      anti-CD33 antibody 12B12

<400> SEQUENCE: 12

Met Glu Thr Asp Thr Leu Leu Leu Trp Val Leu Leu Leu Trp Val Pro
1               5                   10                  15

Gly Ser Thr Gly Asp Ile Val Met Thr Gln Ala Ala Phe Ser Asn Pro
            20                  25                  30

Val Thr Leu Gly Thr Ser Ala Ser Ile Ser Cys Arg Ser Ser Gln Ser
        35                  40                  45
```

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Pro Thr Phe Gly Gly Gly Thr Lys
                115                 120                 125

Leu Glu Ile Lys Arg Ala Asp Ala Ala Pro Thr Val Ser Ile Phe Pro
    130                 135                 140

Pro Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 13
<211> LENGTH: 473
<212> TYPE: PRT
<213> ORGANISM: Artificial Sequence
<220> FEATURE:
<223> OTHER INFORMATION: amino acid sequence of the heavy chain of IgG2b
      anti-CD33 antibody 12B12

<400> SEQUENCE: 13

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Thr Val Leu Ala
                20                  25                  30

Arg Pro Gly Ala Ser Val Lys Met Ser Cys Lys Ala Ser Gly Tyr Thr
            35                  40                  45

Phe Thr Thr Tyr Trp Met His Trp Ile Lys Gln Ser Pro Gly Gln Gly
    50                  55                  60

Leu Glu Trp Ile Gly Ala Ile Tyr Pro Gly Asn Ser Asp Thr Ser Tyr
65                  70                  75                  80

Asn Gln Lys Phe Lys Gly Lys Ala Lys Leu Thr Ala Val Thr Ser Ala
                85                  90                  95

Ser Thr Ala Tyr Met Glu Leu Ser Ser Leu Thr Asn Glu Asp Ser Ala
            100                 105                 110

Val Tyr Tyr Cys Glu Ile Tyr Asp Gly Tyr His Phe Ile Tyr Trp Gly
        115                 120                 125

Gln Gly Thr Thr Leu Thr Val Ser Ser Ala Lys Thr Thr Pro Pro Ser
    130                 135                 140

Val Tyr Pro Leu Ala Pro Gly Cys Gly Asp Thr Thr Gly Ser Ser Val
145                 150                 155                 160

Thr Leu Gly Cys Leu Val Lys Gly Tyr Phe Pro Glu Ser Val Thr Val
                165                 170                 175

```
Thr Trp Asn Ser Gly Ser Leu Ser Ser Val His Thr Phe Pro Ala
            180                 185                 190

Leu Leu Gln Ser Gly Leu Tyr Thr Met Ser Ser Val Thr Val Pro
        195                 200                 205

Ser Ser Thr Trp Pro Ser Gln Thr Val Thr Cys Ser Val Ala His Pro
    210                 215                 220

Ala Ser Ser Thr Thr Val Asp Lys Lys Leu Glu Pro Ser Gly Pro Ile
225                 230                 235                 240

Ser Thr Ile Asn Pro Cys Pro Cys Lys Glu Cys His Lys Cys Pro
                245                 250                 255

Ala Pro Asn Leu Glu Gly Gly Pro Ser Val Phe Ile Phe Pro Pro Asn
                260                 265                 270

Ile Lys Asp Val Leu Met Ile Ser Leu Thr Pro Lys Val Thr Cys Val
        275                 280                 285

Val Val Asp Val Ser Glu Asp Asp Pro Asp Val Gln Ile Ser Trp Phe
    290                 295                 300

Val Asn Asn Val Glu Val His Thr Ala Gln Thr Gln Thr His Arg Glu
305                 310                 315                 320

Asp Tyr Asn Ser Thr Ile Arg Val Val Ser Thr Leu Pro Ile Gln His
                325                 330                 335

Gln Asp Trp Met Ser Gly Lys Glu Phe Lys Cys Lys Val Asn Asn Lys
                340                 345                 350

Asp Leu Pro Ser Pro Ile Glu Arg Thr Ile Ser Lys Ile Lys Gly Leu
                355                 360                 365

Val Arg Ala Pro Gln Val Tyr Ile Leu Pro Pro Ala Glu Gln Leu
    370                 375                 380

Ser Arg Lys Asp Val Ser Leu Thr Cys Leu Val Val Gly Phe Asn Pro
385                 390                 395                 400

Gly Asp Ile Ser Val Glu Trp Thr Ser Asn Gly His Thr Glu Glu Asn
                405                 410                 415

Tyr Lys Asp Thr Ala Pro Val Leu Asp Ser Asp Gly Ser Tyr Phe Ile
                420                 425                 430

Tyr Ser Lys Leu Asn Met Lys Thr Ser Lys Trp Glu Lys Thr Asp Ser
                435                 440                 445

Phe Ser Cys Asn Val Arg His Glu Gly Leu Lys Asn Tyr Tyr Leu Lys
450                 455                 460

Lys Thr Ile Ser Arg Ser Pro Gly Lys
465                 470

<210> SEQ ID NO 14
<211> LENGTH: 238
<212> TYPE: PRT
<213> ORGANISM: Artificial Sequence
<220> FEATURE:
<223> OTHER INFORMATION: amino acid sequence of the light chain of IgG1
      anti-CD33 antibody 4H10

<400> SEQUENCE: 14

Met Glu Thr Asp Thr Leu Leu Leu Trp Val Leu Leu Leu Trp Val Pro
1               5                   10                  15

Gly Ser Thr Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Tyr Ser Asn Gly Lys Thr Tyr Leu His Trp Phe Leu Gln Arg
```

```
            50                  55                  60
Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Arg Thr Phe Gly Gly Gly Thr Lys
                115                 120                 125

Leu Glu Ile Lys Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 15
<211> LENGTH: 464
<212> TYPE: PRT
<213> ORGANISM: Artificial Sequence
<220> FEATURE:
<223> OTHER INFORMATION: amino acid sequence of the heavy chain of IgG1
      anti-CD33 antibody 4H10

<400> SEQUENCE: 15

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Ala Glu Leu Val
                20                  25                  30

Arg Pro Gly Thr Ser Val Lys Val Ser Cys Lys Ala Ser Gly Tyr Ala
            35                  40                  45

Phe Thr Asn Tyr Leu Ile Glu Trp Val Lys Gln Arg Pro Gly Gln Gly
        50                  55                  60

Leu Glu Trp Ile Gly Val Ile His Pro Gly Asn Asn Ser Thr Ser Tyr
65                  70                  75                  80

Asn Ala Lys Phe Arg Gly Lys Ala Thr Leu Thr Ala Asp Arg Ser Ser
                85                  90                  95

Ser Thr Ala Tyr Met Gln Leu Ser Ser Leu Thr Ser Glu Asp Ser Ala
            100                 105                 110

Val Tyr Phe Cys Ala Arg Tyr Gly Tyr Asp Glu Arg Asn Ala Met Asp
        115                 120                 125

Tyr Trp Gly Gln Gly Thr Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175
```

-continued

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Val
        195                 200                 205

Thr Val Pro Ser Ser Pro Arg Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
        260                 265                 270

Thr Pro Lys Val Thr Cys Val Val Val Asp Ile Ser Lys Asp Asp Pro
    275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asn
                405                 410                 415

Thr Asn Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

<210> SEQ ID NO 16
<211> LENGTH: 239
<212> TYPE: PRT
<213> ORGANISM: Artificial Sequence
<220> FEATURE:
<223> OTHER INFORMATION: amino acid sequence of the light chain of IgG1
      anti-CD33 antibody 11D5

<400> SEQUENCE: 16

Met Glu Thr Asp Thr Leu Leu Leu Trp Val Leu Leu Leu Trp Val Pro
1               5                   10                  15

Gly Ser Thr Gly Asp Ile Val Met Thr Gln Ala Ala Phe Ser Asn Pro
            20                  25                  30

Val Thr Leu Gly Thr Ser Ala Ser Ile Ser Cys Arg Ser Asn Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65                  70                  75                  80

```
Ser Gly Val Pro Asp Arg Phe Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Pro Thr Phe Gly Gly Gly Thr Lys
            115                 120                 125

Leu Glu Ile Lys Arg Ala Asp Ala Ala Pro Thr Val Ser Ile Phe Pro
            130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
            210                 215                 220

Thr Ser Thr Ser Pro Ile Val Lys Ser Phe Asn Arg Asn Glu Cys
225                 230                 235

<210> SEQ ID NO 17
<211> LENGTH: 461
<212> TYPE: PRT
<213> ORGANISM: Artificial Sequence
<220> FEATURE:
<223> OTHER INFORMATION: amino acid sequence of the heavy chain of IgG1
      anti-CD33 antibody 11D5

<400> SEQUENCE: 17

Met Glu Thr Asp Thr Leu Leu Leu Trp Val Leu Leu Trp Val Pro
1               5                   10                  15

Gly Ser Thr Gly Glu Val Gln Phe Gln Gln Ser Glu Thr Val Leu Ala
            20                  25                  30

Arg Pro Gly Thr Ser Val Lys Leu Ser Cys Lys Ala Ser Gly Tyr Thr
            35                  40                  45

Phe Thr Ser Tyr Trp Met His Trp Leu Lys Gln Arg Pro Gly Gln Gly
        50                  55                  60

Leu Glu Trp Ile Gly Ala Ile Tyr Cys Gly Asn Ser Asp Thr Ser Tyr
65                  70                  75                  80

Asn Gln Lys Phe Lys Gly Lys Ala Lys Leu Thr Ala Val Thr Ser Ala
                85                  90                  95

Thr Thr Ala Tyr Met Glu Leu Ser Ser Leu Thr Asn Glu Asp Ser Ala
            100                 105                 110

Val Tyr Tyr Cys Lys Ile Tyr Asp Gly Tyr His Phe Asp Tyr Trp Gly
            115                 120                 125

Gln Gly Thr Thr Leu Thr Val Ser Ser Ala Lys Thr Thr Pro Pro Ser
        130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
```

```
            195                 200                 205
Ser Ser Pro Arg Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asn Thr Asn Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
    450                 455                 460

<210> SEQ ID NO 18
<211> LENGTH: 227
<212> TYPE: PRT
<213> ORGANISM: Artificial Sequence
<220> FEATURE:
<223> OTHER INFORMATION: amino acid sequence of the light chain of IgG1
      anti-CD33 antibody 13E11

<400> SEQUENCE: 18

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Val Ser Leu Ala
            20                  25                  30

Val Ser Leu Gly Gln Arg Ala Thr Ile Ser Cys Lys Ala Ser His Gly
        35                  40                  45

Val Glu Tyr Ala Gly Ala His Tyr Met Asn Trp Tyr Gln Gln Lys Pro
    50                  55                  60

Gly Gln Pro Pro Lys Leu Leu Ile Tyr Ala Ala Ser Asn Leu Gly Ser
65                  70                  75                  80

Gly Thr Asp Phe Thr Leu Asn Ile His Pro Val Glu Glu Glu Asp Ser
                85                  90                  95
```

```
Ala Thr Tyr Tyr Cys Gln Gln Ser Asn Glu Asp Pro Arg Thr Phe Gly
            100                 105                 110

Gly Gly Thr Lys Leu Glu Ile Lys Arg Ala Asp Ala Ala Pro Thr Val
        115                 120                 125

Ser Ile Phe Pro Pro Ser Ser Glu Gln Leu Thr Ser Gly Gly Ala Ser
    130                 135                 140

Val Val Cys Phe Leu Asn Asn Phe Tyr Pro Lys Asp Ile Asn Val Lys
145                 150                 155                 160

Trp Lys Ile Asp Gly Ser Glu Arg Gln Asn Gly Val Leu Asn Ser Trp
                165                 170                 175

Thr Asp Gln Asp Ser Lys Asp Ser Thr Tyr Ser Met Ser Ser Thr Leu
            180                 185                 190

Thr Leu Thr Lys Asp Glu Tyr Glu Arg His Asn Ser Tyr Thr Cys Glu
        195                 200                 205

Ala Thr His Lys Thr Ser Thr Ser Pro Ile Val Lys Ser Phe Asn Arg
    210                 215                 220

Asn Glu Cys
225

<210> SEQ ID NO 19
<211> LENGTH: 460
<212> TYPE: PRT
<213> ORGANISM: Artificial Sequence
<220> FEATURE:
<223> OTHER INFORMATION: amino acid sequence of the heavy chain of IgG1
      anti-CD33 antibody 13E11

<400> SEQUENCE: 19

Met Glu Thr Asp Thr Leu Leu Leu Trp Val Leu Leu Leu Trp Val Pro
1               5                   10                  15

Gly Ser Thr Gly Lys Val Gln Leu Gln Gln Ser Gly Ala Glu Leu Val
            20                  25                  30

Lys Pro Gly Ala Ser Val Lys Leu Ser Cys Lys Ala Ser Gly Tyr Thr
        35                  40                  45

Phe Thr Asp Tyr Thr Leu His Trp Leu Lys Gln Arg Ser Gly Gln Gly
    50                  55                  60

Leu Glu Trp Ile Gly Trp Phe Tyr Pro Thr Ser Gly Ser Ile Asn Tyr
65                  70                  75                  80

Asn Glu Arg Phe Lys Asp Lys Ala Thr Leu Thr Ala Asp Lys Ser Ser
                85                  90                  95

Ser Thr Val Tyr Met Glu Leu Ser Arg Leu Thr Ser Val Asp Ser Ala
            100                 105                 110

Val Tyr Phe Cys Ala Arg His Lys Phe Gly Phe Asp Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Pro Arg Pro Ser Glu Thr Val Thr Cys Asn Val Ala His Pro Ala
    210                 215                 220
```

```
Ser Ser Thr Lys Val Asp Lys Ile Val Pro Arg Asp Cys Gly Cys
225                 230                 235                 240

Lys Pro Cys Ile Cys Thr Val Pro Glu Val Ser Ser Val Phe Ile Phe
            245                 250                 255

Pro Pro Lys Pro Lys Asp Val Leu Thr Ile Thr Leu Thr Pro Lys Val
        260                 265                 270

Thr Cys Val Val Val Asp Ile Ser Lys Asp Asp Pro Glu Val Gln Phe
    275                 280                 285

Ser Trp Phe Val Asp Asp Val Glu Val His Thr Ala Gln Thr Gln Pro
290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
            325                 330                 335

Asn Ser Ala Ala Phe Pro Ala Pro Ile Glu Lys Thr Ile Ser Lys Thr
        340                 345                 350

Lys Gly Arg Pro Lys Ala Pro Gln Val Tyr Thr Ile Pro Pro Pro Lys
    355                 360                 365

Glu Gln Met Ala Lys Asp Lys Val Ser Leu Thr Cys Met Ile Thr Asp
370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asn Thr Asn Gly Ser
            405                 410                 415

Tyr Phe Val Tyr Ser Lys Leu Asn Val Gln Lys Ser Asn Trp Glu Ala
        420                 425                 430

Gly Asn Thr Phe Thr Cys Ser Val Leu His Glu Gly Leu His Asn His
    435                 440                 445

His Thr Glu Lys Ser Leu Ser His Ser Pro Gly Lys
450                 455                 460

<210> SEQ ID NO 20
<211> LENGTH: 234
<212> TYPE: PRT
<213> ORGANISM: Artificial Sequence
<220> FEATURE:
<223> OTHER INFORMATION: amino acid sequence of the light chain of IgG1
      anti-CD33 antibody 5E10.7

<400> SEQUENCE: 20

Met Glu Thr Asp Thr Leu Leu Leu Trp Val Leu Leu Leu Trp Val Pro
1               5                   10                  15

Gly Ser Thr Gly Asp Ile Lys Met Thr Gln Ser Pro Ser Ser Ile Tyr
            20                  25                  30

Ala Ser Leu Gly Glu Arg Val Thr Ile Thr Cys Lys Ala Ser Gln Asp
        35                  40                  45

Ile Lys Ser Tyr Leu Ser Trp Tyr Gln Gln Lys Pro Arg Lys Ser Pro
    50                  55                  60

Lys Thr Leu Ile Tyr Tyr Ala Thr Thr Leu Ala Asp Gly Val Pro Ser
65                  70                  75                  80

Arg Phe Ser Gly Ser Gly Ser Gly Gln Asp Phe Ser Leu Thr Ile Ser
            85                  90                  95

Ser Leu Glu Ser Asp Asp Thr Ala Thr Tyr Tyr Cys Leu His His Ser
        100                 105                 110

Glu Ser Pro Trp Thr Phe Gly Gly Gly Thr Lys Leu Glu Ile Lys Arg
```

```
              115                 120                 125
Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
                195                 200                 205

His Asn Ser Tyr Thr Cys Glu Ala Thr His Lys Thr Ser Thr Ser Pro
            210                 215                 220

Ile Val Lys Ser Phe Asn Arg Asn Glu Cys
225                 230

<210> SEQ ID NO 21
<211> LENGTH: 462
<212> TYPE: PRT
<213> ORGANISM: Artificial Sequence
<220> FEATURE:
<223> OTHER INFORMATION: amino acid sequence of the heavy chain of IgG1
      anti-CD33 antibody 5E10.7

<400> SEQUENCE: 21

Met Glu Thr Asp Thr Leu Leu Leu Trp Val Leu Leu Leu Trp Val Pro
1               5                   10                  15

Gly Ser Thr Gly Gln Val Gln Leu Gln Gln Pro Gly Ala Glu Phe Val
                20                  25                  30

Lys Pro Gly Ala Ser Val Lys Leu Ser Cys Lys Ala Ser Gly Tyr Thr
            35                  40                  45

Phe Thr Ser Tyr Trp Met Gln Trp Val Lys Gln Arg Pro Gly Gln Gly
        50                  55                  60

Leu Glu Trp Ile Gly Glu Ile Asp Ser Ser Asp Ser Tyr Thr Asn Tyr
65                  70                  75                  80

Asn Gln Lys Phe Lys Gly Met Ala Thr Leu Thr Val Asp Arg Ser Ser
                85                  90                  95

Ser Thr Ala Tyr Met Gln Leu Ser Ser Leu Thr Ser Glu Asp Ser Ala
                100                 105                 110

Val Tyr Tyr Cys Ala Arg Ser Arg Pro Tyr Asp Trp Phe Pro Tyr Trp
            115                 120                 125

Gly Gln Gly Thr Leu Val Thr Val Ser Thr Ala Lys Thr Thr Pro Pro
130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
                180                 185                 190

Ala Val Leu Gln Ser Asp Leu Tyr Thr Leu Ser Ser Ser Val Thr Val
            195                 200                 205

Pro Ser Ser Pro Arg Pro Ser Glu Thr Val Thr Cys Asn Val Ala His
        210                 215                 220

Pro Ala Ser Ser Thr Lys Val Asp Lys Lys Ile Val Pro Arg Asp Cys
225                 230                 235                 240
```

Gly Cys Lys Pro Cys Ile Cys Thr Val Pro Glu Val Ser Ser Val Phe
            245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
            275                 280                 285

Gln Phe Ser Trp Phe Val Asp Asp Val Glu Val His Thr Ala Gln Thr
            290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
            325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
            370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asn Thr Asn
            405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
    450                 455                 460

<210> SEQ ID NO 22
<211> LENGTH: 234
<212> TYPE: PRT
<213> ORGANISM: Artificial Sequence
<220> FEATURE:
<223> OTHER INFORMATION: amino acid sequence of the light chain of IgG1
      anti-CD33 antibody 11D11

<400> SEQUENCE: 22

Met Glu Thr Asp Thr Leu Leu Leu Trp Val Leu Leu Leu Trp Val Pro
1               5                   10                  15

Gly Ser Thr Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
            35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
            85                  90                  95

Asn Leu Glu Gln Glu Asp Ile Ala Thr Tyr Phe Cys Gln Gln Gly Ser
            100                 105                 110

Thr Leu Pro Pro Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
            130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 23
<211> LENGTH: 462
<212> TYPE: PRT
<213> ORGANISM: Artificial Sequence
<220> FEATURE:
<223> OTHER INFORMATION: amino acid sequence of the heavy chain of IgG1
      anti-CD33 antibody 11D11

<400> SEQUENCE: 23

Met Glu Thr Asp Thr Leu Leu Leu Trp Val Leu Leu Trp Val Pro
1               5                   10                  15

Gly Ser Thr Gly Glu Val Asn Leu Val Glu Ser Gly Gly Gly Leu Val
                20                  25                  30

Gln Ser Gly Arg Ser Leu Arg Leu Ser Cys Ala Thr Ser Gly Phe Thr
            35                  40                  45

Phe Ser Asp Phe Tyr Met Glu Trp Val Arg Gln Ala Pro Gly Lys Gly
        50                  55                  60

Leu Glu Trp Ile Ala Ala Ser Arg Asn Lys Ala Asn Asp Tyr Thr Thr
65                  70                  75                  80

Glu Tyr Lys Ala Ser Val Lys Gly Arg Phe Ile Val Ser Arg Asp Thr
                85                  90                  95

Ser Gln Ser Ile Leu Tyr Leu Gln Met Asn Ala Leu Arg Ala Glu Asp
            100                 105                 110

Thr Ala Ile Tyr Tyr Cys Thr Arg Asp Thr Gly Pro Met Asp Tyr Trp
        115                 120                 125

Gly Gln Gly Thr Ser Val Thr Val Ser Ser Ala Lys Thr Thr Pro Pro
130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Pro Arg Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro

```
                    260                 265                 270
Lys Val Thr Cys Val Val Asp Ile Ser Lys Asp Pro Glu Val
            275                 280                 285
Gln Phe Ser Trp Phe Val Asp Asp Val Glu Val His Thr Ala Gln Thr
290                 295                 300
Gln Pro Arg Glu Glu Gln Phe Asn Ser Thr Phe Arg Ser Val Ser Glu
305                 310                 315                 320
Leu Pro Ile Met His Gln Asp Trp Leu Asn Gly Lys Glu Phe Lys Cys
                325                 330                 335
Arg Val Asn Ser Ala Ala Phe Pro Ala Pro Ile Glu Lys Thr Ile Ser
            340                 345                 350
Lys Thr Lys Gly Arg Pro Lys Ala Pro Gln Val Tyr Thr Ile Pro Pro
            355                 360                 365
Pro Lys Glu Gln Met Ala Lys Asp Lys Val Ser Leu Thr Cys Met Ile
            370                 375                 380
Thr Asp Phe Phe Pro Glu Asp Ile Thr Val Glu Trp Gln Trp Asn Gly
385                 390                 395                 400
Gln Pro Ala Glu Asn Tyr Lys Asn Thr Gln Pro Ile Met Asn Thr Asn
                405                 410                 415
Gly Ser Tyr Phe Val Tyr Ser Lys Leu Asn Val Gln Lys Ser Asn Trp
            420                 425                 430
Glu Ala Gly Asn Thr Phe Thr Cys Ser Val Leu His Glu Gly Leu His
            435                 440                 445
Asn His His Thr Glu Lys Ser Leu Ser His Ser Pro Gly Lys
    450                 455                 460

<210> SEQ ID NO 24
<211> LENGTH: 239
<212> TYPE: PRT
<213> ORGANISM: Artificial Sequence
<220> FEATURE:
<223> OTHER INFORMATION: amino acid sequence of the light chain of IgG1
      anti-CD33 antibody 7E7

<400> SEQUENCE: 24

Met Glu Thr Asp Thr Leu Leu Leu Trp Val Leu Leu Leu Trp Val Pro
1               5                   10                  15
Gly Ser Thr Gly Asp Val Val Met Thr Gln Thr Pro Leu Ile Leu Ser
            20                  25                  30
Val Thr Ile Gly Gln Pro Ala Ser Ile Ser Cys Lys Ser Ser Gln Ser
        35                  40                  45
Leu Leu Asp Ser Asp Gly Lys Thr Tyr Leu Ser Trp Leu Leu Gln Arg
    50                  55                  60
Pro Gly Gln Ser Pro Lys Arg Leu Ile His Leu Val Ser Lys Leu Asp
65                  70                  75                  80
Ser Gly Val Pro Asp Arg Phe Thr Gly Ser Gly Ser Gly Thr Asp Phe
                85                  90                  95
Thr Leu Lys Ile Ser Arg Val Glu Ala Glu Asp Leu Gly Val Tyr Tyr
            100                 105                 110
Cys Trp Gln Gly Thr His Phe Pro Leu Thr Phe Gly Ala Gly Thr Lys
        115                 120                 125
Leu Glu Leu Lys Arg Ala Asp Ala Ala Pro Thr Val Ser Ile Phe Pro
    130                 135                 140
Pro Ser Ser Glu Gln Leu Thr Ser Gly Gly Ala Ser Val Val Cys Phe
145                 150                 155                 160
```

```
Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
        180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 25
<211> LENGTH: 463
<212> TYPE: PRT
<213> ORGANISM: Artificial Sequence
<220> FEATURE:
<223> OTHER INFORMATION: amino acid sequence of the heavy chain of IgG1
      anti-CD33 antibody 7E7

<400> SEQUENCE: 25

Met Glu Thr Asp Thr Leu Leu Leu Trp Val Leu Leu Leu Trp Val Pro
1               5                  10                  15

Gly Ser Thr Gly Gln Val Thr Leu Lys Glu Ser Gly Pro Gly Ile Leu
            20                  25                  30

Gln Pro Ser Gln Thr Leu Ser Leu Thr Cys Ser Phe Ser Gly Phe Ser
        35                  40                  45

Leu Asn Ser Tyr Gly Met Gly Ile Gly Trp Ile Arg Gln Pro Ser Gly
    50                  55                  60

Lys Gly Leu Glu Trp Leu Ala His Ile Trp Trp Asp Asp Asn Lys Tyr
65                  70                  75                  80

Tyr Lys Pro Asp Leu Lys Ser Arg Leu Thr Val Ser Lys Asp Thr Ser
                85                  90                  95

Lys Asn Gln Val Phe Leu Lys Ile Ala Asn Val Asp Thr Thr Asp Thr
            100                 105                 110

Ala Thr Tyr Phe Cys Ala Arg Asp Gly Gly Tyr Ser Leu Phe Ala Tyr
        115                 120                 125

Trp Gly Gln Gly Thr Leu Val Thr Val Ser Val Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Pro Ser Ser Pro Arg Pro Ser Glu Thr Val Thr Cys Asn Val Ala
    210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
        275                 280                 285
```

Val Gln Phe Ser Trp Phe Val Asp Asp Val Glu Val His Thr Ala Gln
    290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
                340                 345                 350

Ser Lys Thr Lys Gly Arg Pro Lys Ala Pro Gln Val Tyr Thr Ile Pro
                355                 360                 365

Pro Pro Lys Glu Gln Met Ala Lys Asp Lys Val Ser Leu Thr Cys Met
370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asn Thr
                405                 410                 415

Asn Gly Ser Tyr Phe Val Tyr Ser Lys Leu Asn Val Gln Lys Ser Asn
                420                 425                 430

Trp Glu Ala Gly Asn Thr Phe Thr Cys Ser Val Leu His Glu Gly Leu
                435                 440                 445

His Asn His His Thr Glu Lys Ser Leu Ser His Ser Pro Gly Lys
450                 455                 460

<210> SEQ ID NO 26
<211> LENGTH: 117
<212> TYPE: PRT
<213> ORGANISM: Artificial Sequence
<220> FEATURE:
<223> OTHER INFORMATION: amino acid sequence of human V-set Ig-like
      domain

<400> SEQUENCE: 26

Pro Asn Phe Trp Leu Gln Val Gln Glu Ser Val Thr Val Gln Glu Gly
1               5                   10                  15

Leu Cys Val Leu Val Pro Cys Thr Phe Phe His Pro Ile Pro Tyr Tyr
                20                  25                  30

Asp Lys Asn Ser Pro Val His Gly Tyr Trp Phe Arg Glu Gly Ala Ile
            35                  40                  45

Ile Ser Arg Asp Ser Pro Val Ala Thr Asn Lys Leu Asp Gln Glu Val
        50                  55                  60

Gln Glu Glu Thr Gln Gly Arg Phe Arg Leu Leu Gly Asp Pro Ser Arg
65                  70                  75                  80

Asn Asn Cys Ser Leu Ser Ile Val Asp Ala Arg Arg Arg Asp Asn Gly
                85                  90                  95

Ser Tyr Phe Phe Arg Met Glu Arg Gly Ser Thr Lys Tyr Ser Tyr Lys
                100                 105                 110

Ser Pro Gln Leu Ser
            115

<210> SEQ ID NO 27
<211> LENGTH: 84
<212> TYPE: PRT
<213> ORGANISM: Artificial Sequence
<220> FEATURE:
<223> OTHER INFORMATION: amino acid sequence of human C2-set Ig-like
      domain

<400> SEQUENCE: 27

```
Pro Lys Ile Leu Ile Pro Gly Thr Leu Glu Pro Gly His Ser Lys Asn
1               5                   10                  15

Leu Thr Cys Ser Val Ser Trp Ala Cys Glu Gln Gly Thr Pro Pro Ile
                20                  25                  30

Phe Ser Trp Leu Ser Ala Ala Pro Thr Ser Leu Gly Pro Arg Thr Thr
            35                  40                  45

His Ser Ser Val Leu Ile Ile Thr Pro Arg Pro Gln Asp His Gly Thr
        50                  55                  60

Asn Leu Thr Cys Gln Val Lys Phe Ala Gly Ala Gly Val Thr Thr Glu
65                  70                  75                  80

Arg Thr Ile Gln

<210> SEQ ID NO 28
<211> LENGTH: 19
<212> TYPE: PRT
<213> ORGANISM: Artificial Sequence
<220> FEATURE:
<223> OTHER INFORMATION: amino terminal peptide (neoepitope) in CD33
      confirmed by mass spectrophotometry (MS)

<400> SEQUENCE: 28

Met Pro Leu Leu Leu Leu Leu Pro Leu Leu Trp Ala Asp Leu Thr His
1               5                   10                  15

Arg Pro Lys

<210> SEQ ID NO 29
<211> LENGTH: 19
<212> TYPE: PRT
<213> ORGANISM: Artificial Sequence
<220> FEATURE:
<223> OTHER INFORMATION: amino terminal peptide (neoepitope) in CD33
      confirmed by mass spectrophotometry (MS)
<220> FEATURE:
<221> NAME/KEY: MOD_RES
<222> LOCATION: (1)..(1)
<223> OTHER INFORMATION: Met is oxidized

<400> SEQUENCE: 29

Met Pro Leu Leu Leu Leu Leu Pro Leu Leu Trp Ala Asp Leu Thr His
1               5                   10                  15

Arg Pro Lys

<210> SEQ ID NO 30
<211> LENGTH: 17
<212> TYPE: PRT
<213> ORGANISM: Artificial Sequence
<220> FEATURE:
<223> OTHER INFORMATION: amino terminal peptide (neoepitope) in CD33
      confirmed by mass spectrophotometry (MS)

<400> SEQUENCE: 30

Leu Leu Leu Leu Leu Pro Leu Leu Trp Ala Asp Leu Thr His Arg Pro
1               5                   10                  15

Lys

<210> SEQ ID NO 31
<211> LENGTH: 18
<212> TYPE: PRT
<213> ORGANISM: Artificial Sequence
<220> FEATURE:
<223> OTHER INFORMATION: amino terminal peptide (neoepitope) in CD33
      confirmed by mass spectrophotometry (MS)
```

```
<400> SEQUENCE: 31

Pro Leu Leu Leu Leu Pro Leu Leu Trp Ala Asp Leu Thr His Arg
1               5                   10                  15

Pro Lys

<210> SEQ ID NO 32
<211> LENGTH: 364
<212> TYPE: PRT
<213> ORGANISM: Artificial Sequence
<220> FEATURE:
<223> OTHER INFORMATION: amino acid sequence of human full-length CD33

<400> SEQUENCE: 32

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
                100                 105                 110

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
                180                 185                 190

His Ser Ser Val Leu Ile Ile Thr Pro Arg Pro Gln Asp His Gly Thr
            195                 200                 205

Asn Leu Thr Cys Gln Val Lys Phe Ala Gly Ala Gly Val Thr Thr Glu
        210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
                260                 265                 270

Leu Cys Leu Cys Leu Ile Phe Phe Ile Val Lys Thr His Arg Arg Lys
            275                 280                 285

Ala Ala Arg Thr Ala Val Gly Arg Asn Asp Thr His Pro Thr Thr Gly
        290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335
```

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 33
<211> LENGTH: 237
<212> TYPE: PRT
<213> ORGANISM: Artificial Sequence
<220> FEATURE:
<223> OTHER INFORMATION: amino acid sequence of the DeltaE2 version of
      CD33

<400> SEQUENCE: 33

Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235

<210> SEQ ID NO 34
<211> LENGTH: 310
<212> TYPE: PRT
<213> ORGANISM: Artificial Sequence
<220> FEATURE:
<223> OTHER INFORMATION: amino acid sequence of CD33E7a which lacks most
      of the intracellular domain of human CD33 (C-terminal truncation)

<400> SEQUENCE: 34

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

```
Glu Gly Leu Cys Val Leu Val Pro Cys Thr Phe Phe His Pro Ile Pro
         35                  40                  45

Tyr Tyr Asp Lys Asn Ser Pro Val His Gly Tyr Trp Phe Arg Glu Gly
     50                  55                  60

Ala Ile Ile Ser Arg Asp Ser Pro Val Ala Thr Asn Lys Leu Asp Gln
 65                  70                  75                  80

Glu Val Gln Glu Thr Gln Gly Arg Phe Arg Leu Leu Gly Asp Pro
             85                  90                  95

Ser Arg Asn Asn Cys Ser Leu Ser Ile Val Asp Ala Arg Arg Arg Asp
                100                 105                 110

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Val Arg
305                 310

<210> SEQ ID NO 35
<211> LENGTH: 282
<212> TYPE: PRT
<213> ORGANISM: Artificial Sequence
<220> FEATURE:
<223> OTHER INFORMATION: amino acid sequence of cynomolgus CD33

<400> SEQUENCE: 35

Met Pro Leu Leu Leu Leu Pro Leu Leu Trp Ala Gly Ala Leu Ala Met
 1               5                  10                  15

Asp Pro Arg Val Arg Leu Glu Val Gln Glu Ser Val Thr Val Gln Glu
            20                  25                  30

Gly Leu Cys Val Leu Val Pro Cys Thr Phe Phe His Pro Val Pro Tyr
         35                  40                  45

His Thr Arg Asn Ser Pro Val His Gly Tyr Trp Phe Arg Glu Gly Ala
     50                  55                  60

Ile Val Ser Leu Asp Ser Pro Val Ala Thr Asn Lys Leu Asp Gln Glu
 65                  70                  75                  80
```

Val Gln Glu Glu Thr Gln Gly Arg Phe Arg Leu Leu Gly Asp Pro Ser
                85                  90                  95

Arg Asn Asn Cys Ser Leu Ser Ile Val Asp Ala Arg Arg Asp Asn
            100                 105                 110

Gly Ser Tyr Phe Phe Arg Met Glu Lys Gly Ser Thr Lys Tyr Ser Tyr
            115                 120                 125

Lys Ser Thr Gln Leu Ser Val His Val Thr Asp Leu Thr His Arg Pro
            130                 135                 140

Gln Ile Leu Ile Pro Gly Ala Leu Asp Pro Asp His Ser Lys Asn Leu
145                 150                 155                 160

Thr Cys Ser Val Pro Trp Ala Cys Glu Gln Gly Thr Pro Pro Ile Phe
                165                 170                 175

Ser Trp Met Ser Ala Ala Pro Thr Ser Leu Gly Leu Arg Thr Thr His
                180                 185                 190

Ser Ser Val Leu Ile Ile Thr Pro Arg Pro Gln Asp His Gly Thr Asn
                195                 200                 205

Leu Thr Cys Gln Val Lys Phe Pro Gly Ala Gly Val Thr Thr Glu Arg
    210                 215                 220

Thr Ile Gln Leu Asn Val Ser Tyr Ala Ser Gln Asn Pro Arg Thr Asp
225                 230                 235                 240

Ile Phe Leu Gly Asp Gly Ser Arg Lys Ala Arg Lys Gln Gly Val
                245                 250                 255

Val Gln Gly Ala Ile Gly Gly Ala Gly Val Thr Val Leu Leu Ala Leu
                260                 265                 270

Cys Leu Cys Leu Ile Phe Phe Thr Val Gln
                275                 280

<210> SEQ ID NO 36
<211> LENGTH: 283
<212> TYPE: PRT
<213> ORGANISM: Artificial Sequence
<220> FEATURE:
<223> OTHER INFORMATION: amino acid sequence of human CD33
      (HsCD33_P20138) shown in the alignment in FIG. 2

<400> SEQUENCE: 36

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn

```
                145                 150                 155                 160
Leu Thr Cys Ser Val Ser Trp Ala Cys Glu Gln Gly Thr Pro Pro Ile
                    165                 170                 175

Phe Ser Trp Leu Ser Ala Ala Pro Thr Ser Leu Gly Pro Arg Thr Thr
                    180                 185                 190

His Ser Ser Val Leu Ile Ile Thr Pro Arg Pro Gln Asp His Gly Thr
                    195                 200                 205

Asn Leu Thr Cys Gln Val Lys Phe Ala Gly Ala Gly Val Thr Thr Glu
                    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                    245                 250                 255

Val Val His Gly Ala Ile Gly Gly Ala Gly Val Thr Ala Leu Leu Ala
                    260                 265                 270

Leu Cys Leu Cys Leu Ile Phe Phe Ile Val Gln
                    275                 280

<210> SEQ ID NO 37
<211> LENGTH: 267
<212> TYPE: PRT
<213> ORGANISM: Artificial Sequence
<220> FEATURE:
<223> OTHER INFORMATION: amino acid sequence of murine CD33
      (MmCD33_Q63994) shown in the alignment in FIG. 2

<400> SEQUENCE: 37

Met Leu Trp Pro Leu Pro Leu Phe Leu Leu Cys Ala Gly Ser Leu Ala
1               5                   10                  15

Gln Asp Leu Glu Phe Gln Leu Val Ala Pro Glu Ser Val Thr Val Glu
                    20                  25                  30

Glu Gly Leu Cys Val His Val Pro Cys Ser Val Phe Tyr Pro Ser Ile
                    35                  40                  45

Lys Leu Thr Leu Gly Pro Val Thr Gly Ser Trp Leu Arg Lys Gly Val
                    50                  55                  60

Ser Leu His Glu Asp Ser Pro Val Ala Thr Ser Asp Pro Arg Gln Leu
65                  70                  75                  80

Val Gln Lys Ala Thr Gln Gly Arg Phe Gln Leu Leu Gly Asp Pro Gln
                    85                  90                  95

Lys His Asp Cys Ser Leu Phe Ile Arg Asp Ala Gln Lys Asn Asp Thr
                    100                 105                 110

Gly Met Tyr Phe Phe Arg Val Val Arg Glu Pro Phe Val Arg Tyr Ser
                    115                 120                 125

Tyr Lys Lys Ser Gln Leu Ser Leu His Val Thr Ser Leu Ser Arg Thr
                    130                 135                 140

Pro Asp Ile Ile Ile Pro Gly Thr Leu Glu Ala Gly Tyr Pro Ser Asn
145                 150                 155                 160

Leu Thr Cys Ser Val Pro Trp Ala Cys Glu Gln Gly Thr Pro Pro Thr
                    165                 170                 175

Phe Ser Trp Met Ser Thr Ala Leu Thr Ser Leu Ser Arg Thr Thr
                    180                 185                 190

Asp Ser Ser Val Leu Thr Phe Thr Pro Gln Pro Gln Asp His Gly Thr
                    195                 200                 205

Lys Leu Thr Cys Leu Val Thr Phe Ser Gly Ala Gly Val Thr Val Glu
                    210                 215                 220
```

```
Arg Thr Ile Gln Leu Asn Val Thr Arg Lys Ser Gly Gln Met Arg Glu
225                 230                 235                 240

Leu Val Leu Val Ala Val Gly Glu Ala Thr Val Lys Leu Leu Ile Leu
                245                 250                 255

Gly Leu Cys Leu Val Phe Leu Ile Val Met Phe
            260                 265

<210> SEQ ID NO 38
<211> LENGTH: 10
<212> TYPE: PRT
<213> ORGANISM: Artificial Sequence
<220> FEATURE:
<223> OTHER INFORMATION: CDRL1 of anti-CD3 antibody OKT3

<400> SEQUENCE: 38

Ser Ala Ser Ser Ser Val Ser Tyr Met Asn
1               5                   10

<210> SEQ ID NO 39
<211> LENGTH: 11
<212> TYPE: PRT
<213> ORGANISM: Artificial Sequence
<220> FEATURE:
<223> OTHER INFORMATION: CDRL2 of anti-CD3 antibody OKT3

<400> SEQUENCE: 39

Arg Trp Ile Tyr Asp Thr Ser Lys Leu Ala Ser
1               5                   10

<210> SEQ ID NO 40
<211> LENGTH: 9
<212> TYPE: PRT
<213> ORGANISM: Artificial Sequence
<220> FEATURE:
<223> OTHER INFORMATION: CDRL3 of anti-CD3 antibody OKT3

<400> SEQUENCE: 40

Gln Gln Trp Ser Ser Asn Pro Phe Thr
1               5

<210> SEQ ID NO 41
<211> LENGTH: 13
<212> TYPE: PRT
<213> ORGANISM: Artificial Sequence
<220> FEATURE:
<223> OTHER INFORMATION: CDRH1 of anti-CD3 antibody OKT3

<400> SEQUENCE: 41

Lys Ala Ser Gly Tyr Thr Phe Thr Arg Tyr Thr Met His
1               5                   10

<210> SEQ ID NO 42
<211> LENGTH: 16
<212> TYPE: PRT
<213> ORGANISM: Artificial Sequence
<220> FEATURE:
<223> OTHER INFORMATION: CDRH2 of anti-CD3 antibody OKT3

<400> SEQUENCE: 42

Ile Asn Pro Ser Arg Gly Tyr Thr Asn Tyr Asn Gln Lys Phe Lys Asp
1               5                   10                  15

<210> SEQ ID NO 43
<211> LENGTH: 10
<212> TYPE: PRT
<213> ORGANISM: Artificial Sequence
```

```
<220> FEATURE:
<223> OTHER INFORMATION: CDRH3 of anti-CD3 antibody OKT3

<400> SEQUENCE: 43

Tyr Tyr Asp Asp His Tyr Cys Leu Asp Tyr
1               5                   10

<210> SEQ ID NO 44
<211> LENGTH: 242
<212> TYPE: PRT
<213> ORGANISM: Artificial Sequence
<220> FEATURE:
<223> OTHER INFORMATION: amino acid sequence of a scFv derived from OKT3
      which retains the capacity to bind CD3

<400> SEQUENCE: 44

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly
        115                 120                 125

Gly Ser Gly Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met Asn Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Ala His Phe Arg Gly Ser Gly Ser Gly Thr Ser Tyr Ser Leu Thr
        195                 200                 205

Ile Ser Gly Met Glu Ala Glu Asp Ala Ala Thr Tyr Tyr Cys Gln Gln
    210                 215                 220

Trp Ser Ser Asn Pro Phe Thr Phe Gly Ser Gly Thr Lys Leu Glu Ile
225                 230                 235                 240

Asn Arg

<210> SEQ ID NO 45
<211> LENGTH: 11
<212> TYPE: PRT
<213> ORGANISM: Artificial Sequence
<220> FEATURE:
<223> OTHER INFORMATION: CDRL1 of anti-CD3 antibody 20G6-F3

<400> SEQUENCE: 45

Gln Ser Leu Val His Asn Asn Gly Asn Thr Tyr
1               5                   10
```

<210> SEQ ID NO 46

<400> SEQUENCE: 46

000

<210> SEQ ID NO 47
<211> LENGTH: 9
<212> TYPE: PRT
<213> ORGANISM: Artificial Sequence
<220> FEATURE:
<223> OTHER INFORMATION: CDRL3 of anti-CD3 antibody 20G6-F3

<400> SEQUENCE: 47

Gly Gln Gly Thr Gln Tyr Pro Phe Thr
1               5

<210> SEQ ID NO 48
<211> LENGTH: 8
<212> TYPE: PRT
<213> ORGANISM: Artificial Sequence
<220> FEATURE:
<223> OTHER INFORMATION: CDRH1 of anti-CD3 antibody 20G6-F3

<400> SEQUENCE: 48

Gly Phe Thr Phe Thr Lys Ala Trp
1               5

<210> SEQ ID NO 49
<211> LENGTH: 10
<212> TYPE: PRT
<213> ORGANISM: Artificial Sequence
<220> FEATURE:
<223> OTHER INFORMATION: CDRH2 of anti-CD3 antibody 20G6-F3

<400> SEQUENCE: 49

Ile Lys Asp Lys Ser Asn Ser Tyr Ala Thr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: CDRH3 of anti-CD3 antibody 20G6-F3

<400> SEQUENCE: 50

Arg Gly Val Tyr Tyr Ala Leu Ser Pro Phe Asp Tyr
1               5                   10

<210> SEQ ID NO 51
<211> LENGTH: 11
<212> TYPE: PRT
<213> ORGANISM: Artificial Sequence
<220> FEATURE:
<223> OTHER INFORMATION: CDRL1 of anti-CD3 antibody 4B4-D7

<400> SEQUENCE: 51

Gln Ser Leu Val His Asp Asn Gly Asn Thr Tyr
1               5                   10

<210> SEQ ID NO 52

<400> SEQUENCE: 52

000

```
<210> SEQ ID NO 53
<211> LENGTH: 9
<212> TYPE: PRT
<213> ORGANISM: Artificial Sequence
<220> FEATURE:
<223> OTHER INFORMATION: CDRL3 of anti-CD3 antibody 4B4-D7

<400> SEQUENCE: 53

Gly Gln Gly Thr Gln Tyr Pro Phe Thr
1               5

<210> SEQ ID NO 54
<211> LENGTH: 8
<212> TYPE: PRT
<213> ORGANISM: Artificial Sequence
<220> FEATURE:
<223> OTHER INFORMATION: CDRH1 of anti-CD3 antibody 4B4-D7

<400> SEQUENCE: 54

Gly Phe Thr Phe Ser Asn Ala Trp
1               5

<210> SEQ ID NO 55
<211> LENGTH: 10
<212> TYPE: PRT
<213> ORGANISM: Artificial Sequence
<220> FEATURE:
<223> OTHER INFORMATION: CDRH2 of anti-CD3 antibody 4B4-D7

<400> SEQUENCE: 55

Ile Lys Ala Arg Ser Asn Asn Tyr Ala Thr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: CDRH3 of anti-CD3 antibody 4B4-D7

<400> SEQUENCE: 56

Arg Gly Thr Tyr Tyr Ala Ser Lys Pro Phe Asp Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: CDRL1 of anti-CD3 antibody 4E7-C9

<400> SEQUENCE: 57

Gln Ser Leu Glu His Asn Asn Gly Asn Thr Tyr
1               5                   10

<210> SEQ ID NO 58

<400> SEQUENCE: 58

000

<210> SEQ ID NO 59
<211> LENGTH: 9
<212> TYPE: PRT
<213> ORGANISM: Artificial Sequence
<220> FEATURE:
<223> OTHER INFORMATION: CDRL3 of anti-CD3 antibody 4E7-C9
```

<400> SEQUENCE: 59

Gly Gln Gly Thr Gln Tyr Pro Phe Thr
1               5

<210> SEQ ID NO 60
<211> LENGTH: 8
<212> TYPE: PRT
<213> ORGANISM: Artificial Sequence
<220> FEATURE:
<223> OTHER INFORMATION: CDRH1 of anti-CD3 antibody 4E7-C9

<400> SEQUENCE: 60

Gly Phe Thr Phe Ser Asn Ala Trp
1               5

<210> SEQ ID NO 61
<211> LENGTH: 10
<212> TYPE: PRT
<213> ORGANISM: Artificial Sequence
<220> FEATURE:
<223> OTHER INFORMATION: CDRH2 of anti-CD3 antibody 4E7-C9

<400> SEQUENCE: 61

Ile Lys Asp Lys Ser Asn Asn Tyr Ala Thr
1               5                   10

<210> SEQ ID NO 62
<211> LENGTH: 13
<212> TYPE: PRT
<213> ORGANISM: Artificial Sequence
<220> FEATURE:
<223> OTHER INFORMATION: CDRH3 of anti-CD3 antibody 4E7-C9

<400> SEQUENCE: 62

Arg Tyr Val His Tyr Gly Ile Gly Tyr Ala Met Asp Ala
1               5                   10

<210> SEQ ID NO 63
<211> LENGTH: 11
<212> TYPE: PRT
<213> ORGANISM: Artificial Sequence
<220> FEATURE:
<223> OTHER INFORMATION: CDRL1 of anti-CD3 antibody 18F5-H10

<400> SEQUENCE: 63

Gln Ser Leu Val His Thr Asn Gly Asn Thr Tyr
1               5                   10

<210> SEQ ID NO 64

<400> SEQUENCE: 64

000

<210> SEQ ID NO 65
<211> LENGTH: 9
<212> TYPE: PRT
<213> ORGANISM: Artificial Sequence
<220> FEATURE:
<223> OTHER INFORMATION: CDRL3 of anti-CD3 antibody 18F5-H10

<400> SEQUENCE: 65

Gly Gln Gly Thr His Tyr Pro Phe Thr
1               5

```
<210> SEQ ID NO 66
<211> LENGTH: 8
<212> TYPE: PRT
<213> ORGANISM: Artificial Sequence
<220> FEATURE:
<223> OTHER INFORMATION: CDRH1 of anti-CD3 antibody 18F5-H10

<400> SEQUENCE: 66

Gly Phe Thr Phe Thr Asn Ala Trp
1               5

<210> SEQ ID NO 67
<211> LENGTH: 9
<212> TYPE: PRT
<213> ORGANISM: Artificial Sequence
<220> FEATURE:
<223> OTHER INFORMATION: CDRH2 of anti-CD3 antibody 18F5-H10

<400> SEQUENCE: 67

Lys Asp Lys Ser Asn Asn Tyr Ala Thr
1               5

<210> SEQ ID NO 68
<211> LENGTH: 13
<212> TYPE: PRT
<213> ORGANISM: Artificial Sequence
<220> FEATURE:
<223> OTHER INFORMATION: CDRH3 of anti-CD3 antibody 18F5-H10

<400> SEQUENCE: 68

Arg Tyr Val His Tyr Arg Phe Ala Tyr Ala Leu Asp Ala
1               5                   10

<210> SEQ ID NO 69
<211> LENGTH: 11
<212> TYPE: PRT
<213> ORGANISM: Artificial Sequence
<220> FEATURE:
<223> OTHER INFORMATION: CDRL1 of anti-CD8 antibody OKT8

<400> SEQUENCE: 69

Arg Thr Ser Arg Ser Ile Ser Gln Tyr Leu Ala
1               5                   10

<210> SEQ ID NO 70
<211> LENGTH: 7
<212> TYPE: PRT
<213> ORGANISM: Artificial Sequence
<220> FEATURE:
<223> OTHER INFORMATION: CDRL2 of anti-CD8 antibody OKT8

<400> SEQUENCE: 70

Ser Gly Ser Thr Leu Gln Ser
1               5

<210> SEQ ID NO 71
<211> LENGTH: 9
<212> TYPE: PRT
<213> ORGANISM: Artificial Sequence
<220> FEATURE:
<223> OTHER INFORMATION: CDRL3 of anti-CD8 antibody OKT8

<400> SEQUENCE: 71

Gln Gln His Asn Glu Asn Pro Leu Thr
1               5

<210> SEQ ID NO 72
```

```
<211> LENGTH: 6
<212> TYPE: PRT
<213> ORGANISM: Artificial Sequence
<220> FEATURE:
<223> OTHER INFORMATION: CDRH1 of anti-CD8 antibody OKT8

<400> SEQUENCE: 72

Gly Phe Asn Ile Lys Asp
1               5

<210> SEQ ID NO 73
<211> LENGTH: 9
<212> TYPE: PRT
<213> ORGANISM: Artificial Sequence
<220> FEATURE:
<223> OTHER INFORMATION: CDRH2 of anti-CD8 antibody OKT8

<400> SEQUENCE: 73

Arg Ile Asp Pro Ala Asn Asp Asn Thr
1               5

<210> SEQ ID NO 74
<211> LENGTH: 9
<212> TYPE: PRT
<213> ORGANISM: Artificial Sequence
<220> FEATURE:
<223> OTHER INFORMATION: CDRH3 of anti-CD8 antibody OKT8

<400> SEQUENCE: 74

Gly Tyr Gly Tyr Tyr Val Phe Asp His
1               5

<210> SEQ ID NO 75
<211> LENGTH: 109
<212> TYPE: PRT
<213> ORGANISM: Artificial Sequence
<220> FEATURE:
<223> OTHER INFORMATION: amino acid sequence of a variable light chain
      region of the sequence of a binding domain that binds and blocks
      the NK cell inhibitory receptors KIR2DL1 and KIR2DL2/3

<400> SEQUENCE: 75

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
            100                 105

<210> SEQ ID NO 76
<211> LENGTH: 123
<212> TYPE: PRT
<213> ORGANISM: Artificial Sequence
<220> FEATURE:
<223> OTHER INFORMATION: amino acid sequence of a variable heavy chain
      region of the sequence of a binding domain that binds and blocks
      the NK cell inhibitory receptors KIR2DL1 and KIR2DL2/3
```

<400> SEQUENCE: 76

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120

<210> SEQ ID NO 77
<211> LENGTH: 11
<212> TYPE: PRT
<213> ORGANISM: Artificial Sequence
<220> FEATURE:
<223> OTHER INFORMATION: linker

<400> SEQUENCE: 77

Gly Gly Ser Gly Gly Gly Ser Gly Gly Ser Gly
1               5                   10

<210> SEQ ID NO 78
<211> LENGTH: 10
<212> TYPE: PRT
<213> ORGANISM: Artificial Sequence
<220> FEATURE:
<223> OTHER INFORMATION: linker

<400> SEQUENCE: 78

Gly Gly Ser Gly Gly Gly Ser Gly Ser Gly
1               5                   10

<210> SEQ ID NO 79
<211> LENGTH: 8
<212> TYPE: PRT
<213> ORGANISM: Artificial Sequence
<220> FEATURE:
<223> OTHER INFORMATION: linker

<400> SEQUENCE: 79

Gly Gly Ser Gly Gly Gly Ser Gly
1               5

<210> SEQ ID NO 80
<211> LENGTH: 10
<212> TYPE: PRT
<213> ORGANISM: Artificial Sequence
<220> FEATURE:
<223> OTHER INFORMATION: linker

<400> SEQUENCE: 80

Gly Gly Gly Gly Ser Gly Gly Gly Gly Ser
1               5                   10

<210> SEQ ID NO 81
<211> LENGTH: 8
<212> TYPE: PRT
<213> ORGANISM: Artificial Sequence
<220> FEATURE:
<223> OTHER INFORMATION: linker

<400> SEQUENCE: 81

Gly Gly Gly Ser Gly Gly Gly Ser
1               5

<210> SEQ ID NO 82
<211> LENGTH: 6
<212> TYPE: PRT
<213> ORGANISM: Artificial Sequence
<220> FEATURE:
<223> OTHER INFORMATION: linker

<400> SEQUENCE: 82

Gly Gly Ser Gly Gly Ser
1               5

<210> SEQ ID NO 83
<211> LENGTH: 467
<212> TYPE: PRT
<213> ORGANISM: Artificial Sequence
<220> FEATURE:
<223> OTHER INFORMATION: amino acid sequence of the heavy chain of
      anti-CD33 antibody 1H7

<400> SEQUENCE: 83

Met Glu Thr Asp Thr Leu Leu Leu Trp Val Leu Leu Trp Val Pro
1               5                   10                  15

Gly Ser Thr Gly Gln Val Gln Leu Gln Gln Ser Gly Ala Glu Leu Val
            20                  25                  30

Lys Pro Gly Ala Ser Val Lys Ile Ser Cys Lys Ala Ser Gly Tyr Ala
        35                  40                  45

Phe Ser Asn Tyr Trp Met Asn Trp Val Lys Gln Arg Pro Gly Lys Gly
    50                  55                  60

Leu Glu Trp Ile Gly Gln Ile Asn Pro Gly Asp Gly Asp Thr Asn Tyr
65                  70                  75                  80

Asn Gly Lys Phe Lys Gly Lys Ala Thr Leu Thr Ala Asp Lys Ser Ser
                85                  90                  95

Ser Thr Ala Tyr Met Gln Leu Ser Ser Leu Thr Ser Glu Asp Ser Ala
            100                 105                 110

Val Tyr Phe Cys Ala Arg Glu Asp Arg Asp Tyr Phe Asp Tyr Trp Gly
        115                 120                 125

Gln Gly Thr Thr Leu Thr Val Ser Ser Ala Lys Thr Thr Ala Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Thr
        195                 200                 205

Ser Ser Thr Trp Pro Ser Gln Ser Ile Thr Cys Asn Val Ala His Pro
    210                 215                 220

```
Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
            260                 265                 270

Ile Ser Leu Ser Pro Ile Val Thr Cys Val Val Asp Val Ser Glu
        275                 280                 285

Asp Asp Pro Asp Val Gln Ile Ser Trp Phe Val Asn Asn Val Glu Val
    290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Asp Leu Pro Ala Pro Ile
            340                 345                 350

Glu Arg Thr Ile Ser Lys Pro Lys Gly Ser Val Arg Ala Pro Gln Val
        355                 360                 365

Tyr Val Leu Pro Pro Pro Glu Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
            420                 425                 430

Glu Lys Lys Asn Trp Val Glu Arg Asn Ser Tyr Ser Cys Ser Val Val
        435                 440                 445

His Glu Gly Leu His Asn His His Thr Thr Lys Ser Phe Ser Arg Thr
    450                 455                 460

Pro Gly Lys
465

<210> SEQ ID NO 84
<211> LENGTH: 234
<212> TYPE: PRT
<213> ORGANISM: Artificial Sequence
<220> FEATURE:
<223> OTHER INFORMATION: amino acid sequence of the light chain of
      anti-CD33 antibody 1H7

<400> SEQUENCE: 84

Met Glu Thr Asp Thr Leu Leu Leu Trp Val Leu Leu Leu Trp Val Pro
1               5                   10                  15

Gly Ser Thr Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Asn Tyr Tyr Leu Asn Trp Tyr Gln Gln Lys Pro Asp Gly Thr Val
    50                  55                  60

Lys Leu Leu Ile Tyr Tyr Ser Arg Leu His Ser Gly Val Pro Ser
65                  70                  75                  80

Arg Phe Ser Gly Ser Gly Ser Gly Thr Asp Phe Ser Leu Thr Ile Ser
                85                  90                  95

Asn Leu Glu Gln Glu Asp Ile Ala Thr Tyr Phe Cys Gln Gln Asp Asp
            100                 105                 110
```

Ala Leu Pro Tyr Thr Phe Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
            165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
            210                 215                 220

Ile Val Lys Ser Phe Asn Arg Asn Glu Cys
225                 230

<210> SEQ ID NO 85
<211> LENGTH: 11
<212> TYPE: PRT
<213> ORGANISM: Artificial Sequence
<220> FEATURE:
<223> OTHER INFORMATION: CDRL1 of anti-CD33 antibody 1H7

<400> SEQUENCE: 85

Arg Ala Ser Gln Asp Ile Asn Tyr Tyr Leu Asn
1               5                   10

<210> SEQ ID NO 86
<211> LENGTH: 8
<212> TYPE: PRT
<213> ORGANISM: Artificial Sequence
<220> FEATURE:
<223> OTHER INFORMATION: CDRL2 of anti-CD33 antibody 1H7

<400> SEQUENCE: 86

Tyr Ser Ser Arg Leu His Ser Gly
1               5

<210> SEQ ID NO 87
<211> LENGTH: 9
<212> TYPE: PRT
<213> ORGANISM: Artificial Sequence
<220> FEATURE:
<223> OTHER INFORMATION: CDRL3 of anti-CD33 antibody 1H7

<400> SEQUENCE: 87

Gln Gln Asp Asp Ala Leu Pro Tyr Thr
1               5

<210> SEQ ID NO 88
<211> LENGTH: 10
<212> TYPE: PRT
<213> ORGANISM: Artificial Sequence
<220> FEATURE:
<223> OTHER INFORMATION: CDRH1 of anti-CD33 antibody 1H7

<400> SEQUENCE: 88

Gly Tyr Ala Phe Ser Asn Tyr Trp Met Asn
1               5                   10

<210> SEQ ID NO 89

```
<211> LENGTH: 13
<212> TYPE: PRT
<213> ORGANISM: Artificial Sequence
<220> FEATURE:
<223> OTHER INFORMATION: CDRH2 of anti-CD33 antibody 1H7

<400> SEQUENCE: 89

Gln Ile Asn Pro Gly Asp Gly Asp Thr Asn Tyr Asn Gly
1               5                   10

<210> SEQ ID NO 90
<211> LENGTH: 8
<212> TYPE: PRT
<213> ORGANISM: Artificial Sequence
<220> FEATURE:
<223> OTHER INFORMATION: CDRH3 of anti-CD33 antibody 1H7

<400> SEQUENCE: 90

Glu Asp Arg Asp Tyr Phe Asp Tyr
1               5

<210> SEQ ID NO 91
<211> LENGTH: 519
<212> TYPE: PRT
<213> ORGANISM: Artificial Sequence
<220> FEATURE:
<223> OTHER INFORMATION: amino acid sequence of a 1H7-CD3 BiTE (based on
      SEQ ID 83/84)

<400> SEQUENCE: 91

Met Glu Thr Asp Thr Leu Leu Leu Trp Val Leu Leu Leu Trp Val Pro
1               5                   10                  15

Gly Ser Thr Gly Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Ile Asn Tyr Tyr Leu Asn Trp Tyr Gln Gln Lys Pro Asp Gly Thr Val
        50                  55                  60

Lys Leu Leu Ile Tyr Tyr Ser Ser Arg Leu His Ser Gly Val Pro Ser
65                  70                  75                  80

Arg Phe Ser Gly Ser Gly Ser Gly Thr Asp Phe Ser Leu Thr Ile Ser
                85                  90                  95

Asn Leu Glu Gln Glu Asp Ile Ala Thr Tyr Phe Cys Gln Gln Asp Asp
            100                 105                 110

Ala Leu Pro Tyr Thr Phe Gly Gly Thr Lys Leu Glu Ile Lys Gly
        115                 120                 125

Gly Gly Gly Ser Gly Gly Gly Gly Ser Gly Gly Gly Gly Ser Gln Val
    130                 135                 140

Gln Leu Gln Gln Ser Gly Ala Glu Leu Val Lys Pro Gly Ala Ser Val
145                 150                 155                 160

Lys Ile Ser Cys Lys Ala Ser Gly Tyr Ala Phe Ser Asn Tyr Trp Met
                165                 170                 175

Asn Trp Val Lys Gln Arg Pro Gly Lys Gly Leu Glu Trp Ile Gly Gln
            180                 185                 190

Ile Asn Pro Gly Asp Gly Asp Thr Asn Tyr Asn Gly Lys Phe Lys Gly
        195                 200                 205

Lys Ala Thr Leu Thr Ala Asp Lys Ser Ser Thr Ala Tyr Met Gln
    210                 215                 220

Leu Ser Ser Leu Thr Ser Glu Asp Ser Ala Val Tyr Phe Cys Ala Arg
225                 230                 235                 240
```

Glu Asp Arg Asp Tyr Phe Asp Tyr Trp Gly Gln Gly Thr Thr Leu Thr
                245                 250                 255

Val Ser Ser Gly Gly Gly Ser Glu Val Gln Leu Val Glu Ser Gly
            260                 265                 270

Gly Gly Leu Val Gln Pro Gly Gly Ser Leu Lys Leu Ser Cys Ala Ala
            275                 280                 285

Ser Gly Phe Thr Phe Asn Lys Tyr Ala Met Asn Trp Val Arg Gln Ala
        290                 295                 300

Pro Gly Lys Gly Leu Glu Trp Val Ala Arg Ile Arg Ser Lys Tyr Asn
305                 310                 315                 320

Asn Tyr Ala Thr Tyr Tyr Ala Asp Ser Val Lys Asp Arg Phe Thr Ile
                325                 330                 335

Ser Arg Asp Asp Ser Lys Asn Thr Ala Tyr Leu Gln Met Asn Asn Leu
            340                 345                 350

Lys Thr Glu Asp Thr Ala Val Tyr Tyr Cys Val Arg His Gly Asn Phe
        355                 360                 365

Gly Asn Ser Tyr Ile Ser Tyr Trp Ala Tyr Trp Gly Gln Gly Thr Leu
    370                 375                 380

Val Thr Val Ser Ser Gly Gly Gly Gly Ser Gly Gly Gly Gly Ser Gly
385                 390                 395                 400

Gly Gly Ser Gln Thr Val Val Thr Gln Glu Pro Ser Leu Thr Val
            405                 410                 415

Ser Pro Gly Gly Thr Val Thr Leu Thr Cys Gly Ser Ser Thr Gly Ala
        420                 425                 430

Val Thr Ser Gly Asn Tyr Pro Asn Trp Val Gln Gln Lys Pro Gly Gln
            435                 440                 445

Ala Pro Arg Gly Leu Ile Gly Gly Thr Lys Phe Leu Ala Pro Gly Thr
        450                 455                 460

Pro Ala Arg Phe Ser Gly Ser Leu Leu Gly Gly Lys Ala Ala Leu Thr
465                 470                 475                 480

Leu Ser Gly Val Gln Pro Glu Asp Glu Ala Glu Tyr Tyr Cys Val Leu
                485                 490                 495

Trp Tyr Ser Asn Arg Trp Val Phe Gly Gly Gly Thr Lys Leu Thr Val
            500                 505                 510

Leu His His His His His His
        515

<210> SEQ ID NO 92
<211> LENGTH: 504
<212> TYPE: PRT
<213> ORGANISM: Artificial Sequence
<220> FEATURE:
<223> OTHER INFORMATION: amino acid sequence of a light chain 1H7-CD3
      engager (based on SEQ ID 84)

<400> SEQUENCE: 92

Met Glu Thr Asp Thr Leu Leu Leu Trp Val Leu Leu Leu Trp Val Pro
1               5                   10                  15

Gly Ser Thr Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Asn Tyr Tyr Leu Asn Trp Tyr Gln Gln Lys Pro Asp Gly Thr Val
    50                  55                  60

Lys Leu Leu Ile Tyr Tyr Ser Ser Arg Leu His Ser Gly Val Pro Ser

```
                65                  70                  75                  80
Arg Phe Ser Gly Ser Gly Ser Gly Thr Asp Phe Ser Leu Thr Ile Ser
                    85                  90                  95

Asn Leu Glu Gln Glu Asp Ile Ala Thr Tyr Phe Cys Gln Gln Asp Asp
            100                 105                 110

Ala Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                    165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
        210                 215                 220

Ile Val Lys Ser Phe Asn Arg Asn Glu Cys Gly Gly Gly Ser Gly
225                 230                 235                 240

Gly Gly Gly Ser Gly Gly Gly Ser Glu Val Gln Leu Val Glu Ser
                    245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                    325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
        370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                    405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                    485                 490                 495
```

-continued

```
Val Leu His His His His His His
        500

<210> SEQ ID NO 93
<211> LENGTH: 467
<212> TYPE: PRT
<213> ORGANISM: Artificial Sequence
<220> FEATURE:
<223> OTHER INFORMATION: amino acid sequence of a heavy chain 1H7-CD3
      engager (based on SEQ ID 83)

<400> SEQUENCE: 93

Met Glu Thr Asp Thr Leu Leu Leu Trp Val Leu Leu Trp Val Pro
1               5                   10                  15

Gly Ser Thr Gly Gln Val Gln Leu Gln Gln Ser Gly Ala Glu Leu Val
            20                  25                  30

Lys Pro Gly Ala Ser Val Lys Ile Ser Cys Lys Ala Ser Gly Tyr Ala
        35                  40                  45

Phe Ser Asn Tyr Trp Met Asn Trp Val Lys Gln Arg Pro Gly Lys Gly
    50                  55                  60

Leu Glu Trp Ile Gly Gln Ile Asn Pro Gly Asp Gly Asp Thr Asn Tyr
65                  70                  75                  80

Asn Gly Lys Phe Lys Gly Lys Ala Thr Leu Thr Ala Asp Lys Ser Ser
                85                  90                  95

Ser Thr Ala Tyr Met Gln Leu Ser Ser Leu Thr Ser Glu Asp Ser Ala
            100                 105                 110

Val Tyr Phe Cys Ala Arg Glu Asp Arg Asp Tyr Phe Asp Tyr Trp Gly
        115                 120                 125

Gln Gly Thr Thr Leu Thr Val Ser Ser Ala Lys Thr Thr Ala Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Thr
        195                 200                 205

Ser Ser Thr Trp Pro Ser Gln Ser Ile Thr Cys Asn Val Ala His Pro
    210                 215                 220

Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
            260                 265                 270

Ile Ser Leu Ser Pro Ile Val Thr Cys Val Val Asp Val Ser Glu
        275                 280                 285

Asp Asp Pro Asp Val Gln Ile Ser Trp Phe Val Asn Asn Val Glu Val
    290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Asp Leu Pro Ala Pro Ile
```

```
                    340                 345                 350
Glu Arg Thr Ile Ser Lys Pro Lys Gly Ser Val Arg Ala Pro Gln Val
                355                 360                 365

Tyr Val Leu Pro Pro Glu Glu Met Thr Lys Lys Gln Val Thr
        370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
                420                 425                 430

Glu Lys Lys Asn Trp Val Glu Arg Asn Ser Tyr Ser Cys Ser Val Val
                435                 440                 445

His Glu Gly Leu His Asn His Thr Thr Lys Ser Phe Ser Arg Thr
            450                 455                 460

Pro Gly Lys
465

<210> SEQ ID NO 94
<211> LENGTH: 10
<212> TYPE: PRT
<213> ORGANISM: Artificial Sequence
<220> FEATURE:
<223> OTHER INFORMATION: CDRH1 of anti-CD33 antibody 5D12

<400> SEQUENCE: 94

Gly Tyr Ala Phe Ser Asn Tyr Trp Met Asn
1               5                   10

<210> SEQ ID NO 95
<211> LENGTH: 17
<212> TYPE: PRT
<213> ORGANISM: Artificial Sequence
<220> FEATURE:
<223> OTHER INFORMATION: CDRH2 of anti-CD33 antibody 5D12

<400> SEQUENCE: 95

Gln Ile Tyr Pro Gly Asn Phe Asn Thr Asp Tyr Asn Gly Gln Phe Lys
1               5                   10                  15
Gly

<210> SEQ ID NO 96
<211> LENGTH: 12
<212> TYPE: PRT
<213> ORGANISM: Artificial Sequence
<220> FEATURE:
<223> OTHER INFORMATION: CDRH3 of anti-CD33 antibody 5D12

<400> SEQUENCE: 96

Phe Phe Asp Phe Gly Ala Tyr Phe Thr Leu Asp Tyr
1               5                   10

<210> SEQ ID NO 97
<211> LENGTH: 11
<212> TYPE: PRT
<213> ORGANISM: Artificial Sequence
<220> FEATURE:
<223> OTHER INFORMATION: CDRL1 of anti-CD33 antibody 5D12

<400> SEQUENCE: 97

Lys Ala Ser Gln Asp Ile Lys Ser Tyr Leu Ser
1               5                   10
```

<210> SEQ ID NO 98
<211> LENGTH: 7
<212> TYPE: PRT
<213> ORGANISM: Artificial Sequence
<220> FEATURE:
<223> OTHER INFORMATION: CDRL2 of anti-CD33 antibody 5D12

<400> SEQUENCE: 98

Tyr Ala Thr Thr Leu Ala Asp
1               5

<210> SEQ ID NO 99
<211> LENGTH: 9
<212> TYPE: PRT
<213> ORGANISM: Artificial Sequence
<220> FEATURE:
<223> OTHER INFORMATION: CDRL3 of anti-CD33 antibody 5D12

<400> SEQUENCE: 99

Leu His His Gly Glu Ser Pro Trp Thr
1               5

<210> SEQ ID NO 100
<211> LENGTH: 11
<212> TYPE: PRT
<213> ORGANISM: Artificial Sequence
<220> FEATURE:
<223> OTHER INFORMATION: CDRH1 of anti-CD33 antibody 8F5

<400> SEQUENCE: 100

Ser Gly Phe Thr Phe Ser Asp Phe Tyr Met Tyr
1               5                   10

<210> SEQ ID NO 101
<211> LENGTH: 17
<212> TYPE: PRT
<213> ORGANISM: Artificial Sequence
<220> FEATURE:
<223> OTHER INFORMATION: CDRH2 of anti-CD33 antibody 8F5

<400> SEQUENCE: 101

Phe Ile Ser Asn Ala Gly Val Thr Thr Tyr Tyr Pro Asp Thr Val Glu
1               5                   10                  15

Gly

<210> SEQ ID NO 102
<211> LENGTH: 10
<212> TYPE: PRT
<213> ORGANISM: Artificial Sequence
<220> FEATURE:
<223> OTHER INFORMATION: CDRH3 of anti-CD33 antibody 8F5

<400> SEQUENCE: 102

Ser Asp Tyr Asp Gly Ala Trp Phe Pro Tyr
1               5                   10

<210> SEQ ID NO 103
<211> LENGTH: 17
<212> TYPE: PRT
<213> ORGANISM: Artificial Sequence
<220> FEATURE:
<223> OTHER INFORMATION: CDRL1 of anti-CD33 antibody 8F5

<400> SEQUENCE: 103

Lys Ser Ser Gln Ser Leu Leu Tyr Ser Arg Asn Gln Tyr Asn Phe Leu

```
1               5               10              15
Ala

<210> SEQ ID NO 104
<211> LENGTH: 7
<212> TYPE: PRT
<213> ORGANISM: Artificial Sequence
<220> FEATURE:
<223> OTHER INFORMATION: CDRL2 of anti-CD33 antibody 8F5

<400> SEQUENCE: 104

Trp Ala Ser Thr Arg Glu Ser
1               5

<210> SEQ ID NO 105
<211> LENGTH: 9
<212> TYPE: PRT
<213> ORGANISM: Artificial Sequence
<220> FEATURE:
<223> OTHER INFORMATION: CDRL3 of anti-CD33 antibody 8F5

<400> SEQUENCE: 105

Gln Gln Tyr Tyr Ser Tyr Pro Tyr Thr
1               5

<210> SEQ ID NO 106
<211> LENGTH: 10
<212> TYPE: PRT
<213> ORGANISM: Artificial Sequence
<220> FEATURE:
<223> OTHER INFORMATION: CDRH1 of anti-CD33 antibody 12B12

<400> SEQUENCE: 106

Gly Tyr Thr Phe Thr Thr Tyr Trp Met His
1               5                   10

<210> SEQ ID NO 107
<211> LENGTH: 13
<212> TYPE: PRT
<213> ORGANISM: Artificial Sequence
<220> FEATURE:
<223> OTHER INFORMATION: CDRH2 of anti-CD33 antibody 12B12

<400> SEQUENCE: 107

Ala Ile Tyr Pro Gly Asn Ser Asp Thr Ser Tyr Asn Gln
1               5                   10

<210> SEQ ID NO 108
<211> LENGTH: 7
<212> TYPE: PRT
<213> ORGANISM: Artificial Sequence
<220> FEATURE:
<223> OTHER INFORMATION: CDRH3 of anti-CD33 antibody 12B12

<400> SEQUENCE: 108

Tyr Asp Gly Tyr His Phe Ile
1               5

<210> SEQ ID NO 109
<211> LENGTH: 16
<212> TYPE: PRT
<213> ORGANISM: Artificial Sequence
<220> FEATURE:
<223> OTHER INFORMATION: CDRL1 of anti-CD33 antibody 12B12

<400> SEQUENCE: 109
```

Arg Ser Ser Gln Ser Leu Leu His Ser Asn Gly Ile Thr Tyr Leu Tyr
1               5                   10                  15

<210> SEQ ID NO 110
<211> LENGTH: 7
<212> TYPE: PRT
<213> ORGANISM: Artificial Sequence
<220> FEATURE:
<223> OTHER INFORMATION: CDRL2 of anti-CD33 antibody 12B12

<400> SEQUENCE: 110

Gln Met Ser Asn Leu Ala Ser
1               5

<210> SEQ ID NO 111
<211> LENGTH: 9
<212> TYPE: PRT
<213> ORGANISM: Artificial Sequence
<220> FEATURE:
<223> OTHER INFORMATION: CDRL3 of anti-CD33 antibody 12B12

<400> SEQUENCE: 111

Ala Gln Asn Leu Glu Leu Pro Pro Thr
1               5

<210> SEQ ID NO 112
<211> LENGTH: 10
<212> TYPE: PRT
<213> ORGANISM: Artificial Sequence
<220> FEATURE:
<223> OTHER INFORMATION: CDRH1 of anti-CD33 antibody 4H10

<400> SEQUENCE: 112

Gly Tyr Ala Phe Thr Asn Tyr Leu Ile Glu
1               5                   10

<210> SEQ ID NO 113
<211> LENGTH: 13
<212> TYPE: PRT
<213> ORGANISM: Artificial Sequence
<220> FEATURE:
<223> OTHER INFORMATION: CDRH2 of anti-CD33 antibody 4H10

<400> SEQUENCE: 113

Val Ile His Pro Gly Asn Asn Ser Thr Ser Tyr Asn Ala
1               5                   10

<210> SEQ ID NO 114
<211> LENGTH: 11
<212> TYPE: PRT
<213> ORGANISM: Artificial Sequence
<220> FEATURE:
<223> OTHER INFORMATION: CDRH3 of anti-CD33 antibody 4H10

<400> SEQUENCE: 114

Tyr Gly Tyr Asp Glu Arg Asn Ala Met Asp Tyr
1               5                   10

<210> SEQ ID NO 115
<211> LENGTH: 13
<212> TYPE: PRT
<213> ORGANISM: Artificial Sequence
<220> FEATURE:
<223> OTHER INFORMATION: CDRL1 of anti-CD33 antibody 4H10

<400> SEQUENCE: 115

Gln Ser Leu Leu Tyr Ser Asn Gly Lys Thr Tyr Leu His

```
<210> SEQ ID NO 116
<211> LENGTH: 16
<212> TYPE: PRT
<213> ORGANISM: Artificial Sequence
<220> FEATURE:
<223> OTHER INFORMATION: CDRL2 of anti-CD33 antibody 4H10

<400> SEQUENCE: 116

Val Pro Asp Arg Phe Thr Gly Ser Gly Ser Gly Thr Asp Phe Thr Leu
1               5                   10                  15

<210> SEQ ID NO 117
<211> LENGTH: 9
<212> TYPE: PRT
<213> ORGANISM: Artificial Sequence
<220> FEATURE:
<223> OTHER INFORMATION: CDRL3 of anti-CD33 antibody 4H10

<400> SEQUENCE: 117

Gly Thr His Phe Pro Arg Thr Phe Gly
1               5

<210> SEQ ID NO 118
<211> LENGTH: 10
<212> TYPE: PRT
<213> ORGANISM: Artificial Sequence
<220> FEATURE:
<223> OTHER INFORMATION: CDRH1 of anti-CD33 antibody 11D5

<400> SEQUENCE: 118

Gly Tyr Thr Phe Thr Ser Tyr Trp Met His
1               5                   10

<210> SEQ ID NO 119
<211> LENGTH: 13
<212> TYPE: PRT
<213> ORGANISM: Artificial Sequence
<220> FEATURE:
<223> OTHER INFORMATION: CDRH2 of anti-CD33 antibody 11D5

<400> SEQUENCE: 119

Ala Ile Tyr Cys Gly Asn Ser Asp Thr Ser Tyr Asn Gln
1               5                   10

<210> SEQ ID NO 120
<211> LENGTH: 8
<212> TYPE: PRT
<213> ORGANISM: Artificial Sequence
<220> FEATURE:
<223> OTHER INFORMATION: CDRH3 of anti-CD33 antibody 11D5

<400> SEQUENCE: 120

Tyr Asp Gly Tyr His Phe Asp Tyr
1               5

<210> SEQ ID NO 121
<211> LENGTH: 16
<212> TYPE: PRT
<213> ORGANISM: Artificial Sequence
<220> FEATURE:
<223> OTHER INFORMATION: CDRL1 of anti-CD33 antibody 11D5

<400> SEQUENCE: 121

Arg Ser Asn Lys Ser Leu Leu His Ser Asn Gly Ile Thr Tyr Leu Tyr
1               5                   10                  15
```

<210> SEQ ID NO 122
<211> LENGTH: 7
<212> TYPE: PRT
<213> ORGANISM: Artificial Sequence
<220> FEATURE:
<223> OTHER INFORMATION: CDRL2 of anti-CD33 antibody 11D5

<400> SEQUENCE: 122

Gln Met Ser Asn Leu Ala Ser
1               5

<210> SEQ ID NO 123
<211> LENGTH: 9
<212> TYPE: PRT
<213> ORGANISM: Artificial Sequence
<220> FEATURE:
<223> OTHER INFORMATION: CDRL3 of anti-CD33 antibody 11D5

<400> SEQUENCE: 123

Ala Gln Asn Leu Glu Leu Pro Pro Thr
1               5

<210> SEQ ID NO 124
<211> LENGTH: 10
<212> TYPE: PRT
<213> ORGANISM: Artificial Sequence
<220> FEATURE:
<223> OTHER INFORMATION: CDRH1 of anti-CD33 antibody 13E11

<400> SEQUENCE: 124

Gly Tyr Thr Phe Thr Asp Tyr Thr Leu His
1               5                   10

<210> SEQ ID NO 125
<211> LENGTH: 13
<212> TYPE: PRT
<213> ORGANISM: Artificial Sequence
<220> FEATURE:
<223> OTHER INFORMATION: CDRH2 of anti-CD33 antibody 13E11

<400> SEQUENCE: 125

Trp Phe Tyr Pro Thr Ser Gly Ser Ile Asn Tyr Asn Glu
1               5                   10

<210> SEQ ID NO 126
<211> LENGTH: 7
<212> TYPE: PRT
<213> ORGANISM: Artificial Sequence
<220> FEATURE:
<223> OTHER INFORMATION: CDRH3 of anti-CD33 antibody 13E11

<400> SEQUENCE: 126

His Lys Phe Gly Phe Asp Tyr
1               5

<210> SEQ ID NO 127
<211> LENGTH: 15
<212> TYPE: PRT
<213> ORGANISM: Artificial Sequence
<220> FEATURE:
<223> OTHER INFORMATION: CDRL1 of anti-CD33 antibody 13E11

<400> SEQUENCE: 127

Lys Ala Ser His Gly Val Glu Tyr Ala Gly Ala His Tyr Met Asn
1               5                   10                  15

<210> SEQ ID NO 128
<211> LENGTH: 7
<212> TYPE: PRT
<213> ORGANISM: Artificial Sequence
<220> FEATURE:
<223> OTHER INFORMATION: CDRL2 of anti-CD33 antibody 13E11

<400> SEQUENCE: 128

Ala Ala Ser Asn Leu Gly Ser
1               5

<210> SEQ ID NO 129
<211> LENGTH: 9
<212> TYPE: PRT
<213> ORGANISM: Artificial Sequence
<220> FEATURE:
<223> OTHER INFORMATION: CDRL3 of anti-CD33 antibody 13E11

<400> SEQUENCE: 129

Gln Gln Ser Asn Glu Asp Pro Arg Thr
1               5

<210> SEQ ID NO 130
<211> LENGTH: 10
<212> TYPE: PRT
<213> ORGANISM: Artificial Sequence
<220> FEATURE:
<223> OTHER INFORMATION: CDRH1 of anti-CD33 antibody 5E10.7

<400> SEQUENCE: 130

Gly Tyr Thr Phe Thr Ser Tyr Trp Met Gln
1               5                   10

<210> SEQ ID NO 131
<211> LENGTH: 13
<212> TYPE: PRT
<213> ORGANISM: Artificial Sequence
<220> FEATURE:
<223> OTHER INFORMATION: CDRH2 of anti-CD33 antibody 5E10.7

<400> SEQUENCE: 131

Glu Ile Asp Ser Ser Asp Ser Tyr Thr Asn Tyr Asn Gln
1               5                   10

<210> SEQ ID NO 132
<211> LENGTH: 9
<212> TYPE: PRT
<213> ORGANISM: Artificial Sequence
<220> FEATURE:
<223> OTHER INFORMATION: CDRH3 of anti-CD33 antibody 5E10.7

<400> SEQUENCE: 132

Ser Arg Pro Tyr Asp Trp Phe Pro Tyr
1               5

<210> SEQ ID NO 133
<211> LENGTH: 11
<212> TYPE: PRT
<213> ORGANISM: Artificial Sequence
<220> FEATURE:
<223> OTHER INFORMATION: CDRL1 of anti-CD33 antibody 5E10.7

<400> SEQUENCE: 133

Lys Ala Ser Gln Asp Ile Lys Ser Tyr Leu Ser
1               5                   10

```
<210> SEQ ID NO 134
<211> LENGTH: 7
<212> TYPE: PRT
<213> ORGANISM: Artificial Sequence
<220> FEATURE:
<223> OTHER INFORMATION: CDRL2 of anti-CD33 antibody 5E10.7

<400> SEQUENCE: 134

Tyr Ala Thr Thr Leu Ala Asp
1               5

<210> SEQ ID NO 135
<211> LENGTH: 9
<212> TYPE: PRT
<213> ORGANISM: Artificial Sequence
<220> FEATURE:
<223> OTHER INFORMATION: CDRL3 of anti-CD33 antibody 5E10.7

<400> SEQUENCE: 135

Leu His His Ser Glu Ser Pro Trp Thr
1               5

<210> SEQ ID NO 136
<211> LENGTH: 11
<212> TYPE: PRT
<213> ORGANISM: Artificial Sequence
<220> FEATURE:
<223> OTHER INFORMATION: CDRH1 of anti-CD33 antibody 11D11

<400> SEQUENCE: 136

Ser Gly Phe Thr Phe Ser Asp Phe Tyr Met Glu
1               5                   10

<210> SEQ ID NO 137
<211> LENGTH: 13
<212> TYPE: PRT
<213> ORGANISM: Artificial Sequence
<220> FEATURE:
<223> OTHER INFORMATION: CDRH2 of anti-CD33 antibody 11D11

<400> SEQUENCE: 137

Ala Ser Arg Asn Lys Ala Asn Asp Tyr Thr Thr Glu Tyr
1               5                   10

<210> SEQ ID NO 138
<211> LENGTH: 7
<212> TYPE: PRT
<213> ORGANISM: Artificial Sequence
<220> FEATURE:
<223> OTHER INFORMATION: CDRH3 of anti-CD33 antibody 11D11

<400> SEQUENCE: 138

Asp Thr Gly Pro Met Asp Tyr
1               5

<210> SEQ ID NO 139
<211> LENGTH: 11
<212> TYPE: PRT
<213> ORGANISM: Artificial Sequence
<220> FEATURE:
<223> OTHER INFORMATION: CDRHL1 of anti-CD33 antibody 11D11

<400> SEQUENCE: 139

Arg Ala Ser Gln Asp Ile Ser Asn Tyr Leu Asn
1               5                   10

<210> SEQ ID NO 140
```

```
<211> LENGTH: 7
<212> TYPE: PRT
<213> ORGANISM: Artificial Sequence
<220> FEATURE:
<223> OTHER INFORMATION: CDRHL2 of anti-CD33 antibody 11D11

<400> SEQUENCE: 140

Tyr Thr Ser Arg Leu His Ser
1               5

<210> SEQ ID NO 141
<211> LENGTH: 9
<212> TYPE: PRT
<213> ORGANISM: Artificial Sequence
<220> FEATURE:
<223> OTHER INFORMATION: CDRHL3 of anti-CD33 antibody 11D11

<400> SEQUENCE: 141

Gln Gln Gly Ser Thr Leu Pro Pro Thr
1               5

<210> SEQ ID NO 142
<211> LENGTH: 12
<212> TYPE: PRT
<213> ORGANISM: Artificial Sequence
<220> FEATURE:
<223> OTHER INFORMATION: CDRH1 of anti-CD33 antibody 7E7

<400> SEQUENCE: 142

Gly Phe Ser Leu Asn Ser Tyr Gly Met Gly Ile Gly
1               5                   10

<210> SEQ ID NO 143
<211> LENGTH: 16
<212> TYPE: PRT
<213> ORGANISM: Artificial Sequence
<220> FEATURE:
<223> OTHER INFORMATION: CDRH2 of anti-CD33 antibody 7E7

<400> SEQUENCE: 143

His Ile Trp Trp Asp Asp Asn Lys Tyr Tyr Lys Pro Asp Leu Lys Ser
1               5                   10                  15

<210> SEQ ID NO 144
<211> LENGTH: 9
<212> TYPE: PRT
<213> ORGANISM: Artificial Sequence
<220> FEATURE:
<223> OTHER INFORMATION: CDRH3 of anti-CD33 antibody 7E7

<400> SEQUENCE: 144

Asp Gly Gly Tyr Ser Leu Phe Ala Tyr
1               5

<210> SEQ ID NO 145
<211> LENGTH: 16
<212> TYPE: PRT
<213> ORGANISM: Artificial Sequence
<220> FEATURE:
<223> OTHER INFORMATION: CDRL1 of anti-CD33 antibody 7E7

<400> SEQUENCE: 145

Lys Ser Ser Gln Ser Leu Leu Asp Ser Asp Gly Lys Thr Tyr Leu Ser
1               5                   10                  15

<210> SEQ ID NO 146
<211> LENGTH: 7
```

```
<212> TYPE: PRT
<213> ORGANISM: Artificial Sequence
<220> FEATURE:
<223> OTHER INFORMATION: CDRL2 of anti-CD33 antibody 7E7

<400> SEQUENCE: 146

Val Ser Lys Leu Asp Ser Gly
1               5

<210> SEQ ID NO 147
<211> LENGTH: 9
<212> TYPE: PRT
<213> ORGANISM: Artificial Sequence
<220> FEATURE:
<223> OTHER INFORMATION: CDRL3 of anti-CD33 antibody 7E7

<400> SEQUENCE: 147

Trp Gln Gly Thr His Phe Pro Leu Thr
1               5

<210> SEQ ID NO 148
<211> LENGTH: 10
<212> TYPE: PRT
<213> ORGANISM: Mus musculus

<400> SEQUENCE: 148

Gly Tyr Thr Phe Thr Asp Tyr Asp Met His
1               5                   10

<210> SEQ ID NO 149
<211> LENGTH: 15
<212> TYPE: PRT
<213> ORGANISM: Mus musculus

<400> SEQUENCE: 149

Ala Ile Asp Pro Glu Thr Gly Gly Thr Ala Tyr Asn Gln Asn Phe
1               5                   10                  15

<210> SEQ ID NO 150
<211> LENGTH: 7
<212> TYPE: PRT
<213> ORGANISM: Mus musculus

<400> SEQUENCE: 150

Asp Tyr Asp Tyr Phe Gly Val
1               5

<210> SEQ ID NO 151
<211> LENGTH: 11
<212> TYPE: PRT
<213> ORGANISM: Mus musculus

<400> SEQUENCE: 151

Lys Ala Ser Gln Asn Val Gly Thr Asn Val Val
1               5                   10

<210> SEQ ID NO 152
<211> LENGTH: 7
<212> TYPE: PRT
<213> ORGANISM: Mus musculus

<400> SEQUENCE: 152

Ser Ala Ser Asp Arg Tyr Ser
1               5
```

```
<210> SEQ ID NO 153
<211> LENGTH: 9
<212> TYPE: PRT
<213> ORGANISM: Mus musculus

<400> SEQUENCE: 153

Gln Gln Tyr Asn Ile Tyr Pro Tyr Thr
1               5

<210> SEQ ID NO 154
<211> LENGTH: 128
<212> TYPE: PRT
<213> ORGANISM: Mus musculus

<400> SEQUENCE: 154

Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Gly Thr Asn Val Val Trp Tyr His Lys Lys Pro Gly Gln Ser Pro
    50                  55                  60

Lys Gly Leu Ile Tyr Ser Ala Ser Asp Arg Tyr Ser Gly Val Pro Asp
65                  70                  75                  80

Arg Phe Thr Gly Ser Gly Ser Gly Thr Asp Phe Thr Leu Thr Ile Asn
                85                  90                  95

Asn Val Gln Ser Glu Asp Leu Ala Glu Tyr Phe Cys Gln Gln Tyr Asn
            100                 105                 110

Ile Tyr Pro Tyr Thr Phe Gly Gly Gly Thr Lys Leu Glu Ile Lys Arg
        115                 120                 125

<210> SEQ ID NO 155
<211> LENGTH: 135
<212> TYPE: PRT
<213> ORGANISM: Mus musculus

<400> SEQUENCE: 155

Met Glu Trp Ser Trp Val Cys Leu Phe Leu Leu Ser Val Ile Ala Gly
1               5                   10                  15

Val Gln Ser Gln Val Gln Leu Gln Gln Ser Gly Ala Glu Leu Val Arg
            20                  25                  30

Pro Gly Ala Ser Val Thr Leu Ser Cys Lys Ala Ser Gly Tyr Thr Phe
        35                  40                  45

Thr Asp Tyr Asp Met His Trp Val Lys Gln Thr Pro Val His Gly Leu
    50                  55                  60

Glu Trp Ile Gly Ala Ile Asp Pro Glu Thr Gly Thr Ala Tyr Asn
65                  70                  75                  80

Gln Asn Phe Lys Gly Lys Ala Ile Leu Thr Val Asp Lys Ser Ser Arg
                85                  90                  95

Ile Ala Tyr Met Glu Leu Arg Ser Leu Thr Ser Glu Asp Ser Ala Val
            100                 105                 110

Phe Tyr Cys Thr Ser Asp Tyr Asp Tyr Phe Gly Val Trp Gly Thr Gly
        115                 120                 125

Thr Thr Val Thr Val Ser Ser
    130                 135

<210> SEQ ID NO 156
```

```
<211> LENGTH: 44
<212> TYPE: PRT
<213> ORGANISM: Artificial sequence
<220> FEATURE:
<223> OTHER INFORMATION: engingeered protein containing signal peptide
      from full length CD33 fused to c-terminal end of CD33deltaE2

<400> SEQUENCE: 156

Met Pro Leu Leu Leu Leu Leu Pro Leu Leu Trp Ala Gly Ala Leu Ala
1               5                   10                  15

Met Asp Leu Thr His Arg Pro Lys Ile Leu Ile Pro Gly Thr Leu Glu
                20                  25                  30

Pro Gly His Ser Lys Asn Leu Thr Cys Ser Val Ser
            35                  40

<210> SEQ ID NO 157
<211> LENGTH: 48
<212> TYPE: PRT
<213> ORGANISM: Artificial sequence
<220> FEATURE:
<223> OTHER INFORMATION: engingeered protein containing signal peptide
      from CD33deltaE2 fused to c-terminal end of full length CD33

<400> SEQUENCE: 157

Met Pro Leu Leu Leu Leu Leu Pro Leu Leu Trp Ala Asp Leu Thr His
1               5                   10                  15

Arg Pro Lys Ile Leu Ile Pro Asn Phe Trp Leu Gln Val Gln Glu Ser
                20                  25                  30

Val Thr Val Gln Glu Gly Leu Cys Val Leu Val Pro Cys Thr Phe Phe
            35                  40                  45

<210> SEQ ID NO 158
<211> LENGTH: 15
<212> TYPE: PRT
<213> ORGANISM: Artificial sequence
<220> FEATURE:
<223> OTHER INFORMATION: glycine-serine linker

<400> SEQUENCE: 158

Gly Gly Gly Gly Ser Gly Gly Gly Gly Ser Gly Gly Gly Gly Ser
1               5                   10                  15

<210> SEQ ID NO 159
<211> LENGTH: 5
<212> TYPE: PRT
<213> ORGANISM: Artificial sequence
<220> FEATURE:
<223> OTHER INFORMATION: glycine-serine linker

<400> SEQUENCE: 159

Gly Gly Gly Gly Ser
1               5
```

What is claimed is:

1. A CD33-binding isolated monoclonal antibody or CD33-binding fragment thereof comprising
a variable light chain comprising
a complementarity determining region light (CDRL)1 having the sequence as set forth in SEQ ID NO: 133,
a CDRL2 having the sequence as set forth in SEQ ID NO: 134, and
a CDRL3 having the sequence as set forth in SEQ ID NO: 135, and
a variable heavy chain comprising
a CDR heavy (H)1 having the sequence as set forth in SEQ ID NO: 130,
a CDRH2 having the sequence as set forth in SEQ ID NO: 131, and
a CDRH3 having the sequence as set forth in SEQ ID NO: 132.

2. The CD33-binding isolated monoclonal antibody or CD33-binding fragment thereof of claim 1, wherein
the variable light chain has the sequence as set forth in SEQ ID NO: 20 or a sequence having at least 90% sequence identity thereto and
the variable heavy chain has the sequence as set forth in SEQ ID NO: 21 or a sequence having at least 90% sequence identity thereto.

3. The CD33-binding isolated monoclonal antibody or CD33-binding fragment thereof of claim 1, in the form of a whole antibody, a single chain variable fragment (scFv), or an immunoconjugate.

4. A bispecific antibody molecule or bispecific antigen binding fragment thereof comprising the variable light chain and the variable heavy chain of the CD33-binding monoclonal antibody or antigen binding fragment thereof of claim 1.

5. The bispecific antibody molecule or bispecific antigen binding fragment thereof of claim 4, wherein the bispecific antibody molecule or bispecific antigen binding fragment thereof further comprises a CD3 binding domain or a CD8 binding domain.

6. The bispecific antibody molecule or bispecific antigen binding fragment thereof of claim 5, wherein the CD3 binding domain comprises
a variable light chain comprising
a CDRL1 having the sequence as set forth in SEQ ID NO: 38,
a CDRL2 having the sequence as set forth in SEQ ID NO: 39, and
B a CDRL3 having the sequence as set forth in SEQ ID NO: 40, and
a variable heavy chain comprising
a CDRH1 having the sequence as set forth in SEQ ID NO: 41,
a CDRH2 having the sequence as set forth in SEQ ID NO: 42, and
a CDRH3 having the sequence as set forth in SEQ ID NO: 43.

7. The bispecific antibody molecule or bispecific antigen binding fragment thereof of claim 5, wherein the CD8 binding domain comprises
a variable light chain comprising
a CDRL1 having the sequence as set forth in SEQ ID NO: 69,
a CDRL2 having the sequence as set forth in SEQ ID NO: 70, and
B a CDRL3 having the sequence as set forth in SEQ ID NO: 71, and
a variable heavy chain comprising
a CDRH1 having the sequence as set forth in SEQ ID NO: 72,
a CDRH2 having the sequence as set forth in SEQ ID NO: 73, and
a CDRH3 having the sequence as set forth in SEQ ID NO: 74.

8. A chimeric antigen receptor (CAR) comprising
an extracellular component comprising a CD33-binding isolated monoclonal antibody or 1 CD33-binding fragment thereof of claim 1,
a transmembrane domain, and
an effector domain,
wherein the transmembrane domain links the extracellular component to the effector domain.

9. The CD33-binding isolated monoclonal antibody or CD33-binding fragment thereof of claim 1, wherein the CD33-binding isolated monoclonal antibody or CD33-fragment thereof is covalently conjugated to polyethylene glycol (PEG).

10. The CD33-binding isolated monoclonal antibody or CD33-binding 1 fragment thereof of claim 1, wherein the CD33-binding isolated monoclonal antibody or CD33-binding fragment thereof is part of an antibody-drug conjugate comprising maytansinoid, dolastatin, auristatin, calicheamicin, pyrrolobenzodiazepine (PBD), nemorubicin, anthracycline, duocarmycin, *vinca* alkaloid, taxane, trichothecene, camptothecin, or elinafide.

11. A composition comprising the CD33-binding isolated monoclonal 1 antibody or CD33-binding fragment thereof of claim 1 and a pharmaceutically acceptable carrier.

* * * * *